US007135187B2

(12) United States Patent
Graham et al.

(10) Patent No.: US 7,135,187 B2
(45) Date of Patent: Nov. 14, 2006

(54) SYSTEM FOR PRODUCTION OF HELPER DEPENDENT ADENOVIRUS VECTORS BASED ON USE OF ENDONUCLEASES

(75) Inventors: Frank L. Graham, Rome (IT); Philip Ng, Pearland, TX (US); Robin Parks, Ottawa (CA)

(73) Assignee: AdVec, Inc., Ancaster (CA)

( * ) Notice: Subject to any disclaimer, the term of this patent is extended or adjusted under 35 U.S.C. 154(b) by 625 days.

(21) Appl. No.: 10/355,330

(22) Filed: Jan. 31, 2003

(65) Prior Publication Data

US 2003/0228280 A1   Dec. 11, 2003

Related U.S. Application Data

(63) Continuation of application No. 09/883,649, filed on Jun. 19, 2001, now abandoned, which is a continuation of application No. 09/475,813, filed on Dec. 30, 1999, now abandoned, which is a continuation-in-part of application No. 09/250,929, filed on Feb. 18, 1999, now abandoned, which is a continuation-in-part of application No. 08/473,168, filed on Jun. 7, 1995, now Pat. No. 5,919,676, which is a continuation-in-part of application No. 08/250,885, filed on May 31, 1994, now Pat. No. 6,140,087, which is a continuation-in-part of application No. 08/080,727, filed on Jun. 24, 1993, now abandoned.

(51) Int. Cl.
*A61K 39/23* (2006.01)
*C07H 21/04* (2006.01)
*C12N 7/00* (2006.01)
*C12N 15/00* (2006.01)

(52) U.S. Cl. .............................. 424/233.1; 536/23.72; 435/235.1; 435/320.1

(58) Field of Classification Search .................. None
See application file for complete search history.

(56) References Cited

U.S. PATENT DOCUMENTS

| | | | |
|---|---|---|---|
| 4,510,245 A | 4/1985 | Cousens et al. |
| 4,797,368 A | 1/1989 | Carter et al. |
| 4,920,209 A | 4/1990 | Davis et al. |
| 4,920,211 A | 4/1990 | Tibbetts et al. |
| 5,474,896 A | 12/1995 | Dujon et al. |
| 5,670,488 A | 9/1997 | Gregory et al. |
| 5,849,553 A | 12/1998 | Anderson et al. |
| 5,882,877 A | 3/1999 | Gregory et al. |
| 5,919,676 A | 7/1999 | Graham et al. |
| 5,998,205 A | 12/1999 | Hallenbeck et al. |
| 6,001,557 A | 12/1999 | Wilson et al. |
| 6,080,569 A | 6/2000 | Graham et al. |
| 6,261,807 B1 | 7/2001 | Crouzet et al. |

FOREIGN PATENT DOCUMENTS

| | | |
|---|---|---|
| EP | 0 919 624 | 6/1999 |
| WO | WO 93/06223 | 4/1993 |
| WO | WO 93/19092 | 9/1993 |
| WO | WO 93/19191 | 9/1993 |
| WO | WO 94/08026 | 4/1994 |
| WO | WO94/12649 | 6/1994 |
| WO | WO95/27071 | 12/1995 |
| WO | WO 96/13597 | 5/1996 |
| WO | WO 96/13598 | * 5/1996 |
| WO | WO 96/14408 | 5/1996 |
| WO | WO 96/40955 | 12/1996 |
| WO | WO 97/05255 | 2/1997 |
| WO | WO 97/32481 | 9/1997 |
| WO | WO 98/13510 | 4/1998 |
| WO | WO 99/02647 | 2/1999 |
| WO | WO 99/41400 | 8/1999 |
| WO | WO 99/53085 | 10/1999 |
| WO | WO 99/61638 | 12/1999 |

OTHER PUBLICATIONS

Anglana, Mauro and Silvia Bacciietti, "Construction of a Recombinant Adenovirus for Efficient Delivery of the I-Seel Yeast Endonuclease to Human Cells and it's Application in the *In Vivo* Cleavage of Chromosomes to Expose New Potential Telomeres," Nucleic Acids Research (1999) 27 (21) 4276-4181.
Anton, M., and F. L. Graham, 1995, Site-specific recombination mediated by an adenovirus vector expressing the Cre recombinase protein: a molecular switch for control of gene expression, J. Virol. 69: 4600-4606.
Araki, K., J. Araki, J. I. Miyazaki, and P. Vassali, 1995, Site-specific recombination of a transgene in fertilized eggs by transient expression of Cre recombinase. Proc. Nat'l. Acad. Sci. USA 92: 160-164.
Bett, A. J., L. Prevec, and F. L. Graham, 1993, Packaging capacity and stability of human adenovirus type 5 vectors. J. Virol. 67: 5911-5921.
Bett, A. J., W. Haddara, L. Prev, and F. L. Graham, 1994, An efficient and flexible system for construction of adenivorus vectors with insertions or deletions in early region 1 and 3. Proc. Nat'l. Acad. Sci. USA 91:8802-8806.
D'Halluin et al., "Restriction maps of human adenovirus types 2, 5 and 3 for Bell, Clal. Pvul and Sphl", Gene, 21(1-2):165-169, 1983.

(Continued)

*Primary Examiner*—Richard Schnizer
(74) *Attorney, Agent, or Firm*—Joseph Fischer; Beusse, Wolter, Sanks, Mora & Maire, P.A.

(57) ABSTRACT

The present invention relates to methods for efficient and reliable construction of adenovirus vectors which contain and express foreign DNA and are useful for gene transfer into mammalian cells, for vaccines and for gene therapy. The invention provides for the growth and purification of adenovirus vectors (helper dependent vectors or HDVs) from which all or most of the viral genes have been removed. The vector system described herein is a new method designed to eliminate helper viruses from the final HDV preparation by cleavage of the helper virus DNA with an endonuclease, alone or in combination with other methods known to limit the level of helper virus contamination of helper dependent vector preparations. The disclosed methods and compositions also provide for regulated control of gene expression.

22 Claims, 39 Drawing Sheets

OTHER PUBLICATIONS

DiSanto, J.P., W. Mueller, D. Guy-Grand, A. Fischer, and K. Rajewsky, 1995, Lymphoid development in mice with a targeted deletion of the interleukin 2 receptor chain, Proc. Nat'l. Acad. Sci. USA 92: 377-381.

Gage, P.J., B. Sauer, M. Levin and J. C. Glorioso. 1992. A cell-free recombination system for site-specific integration of multigenic shuttle plasmids into the herpes simplex virus type 1 genome. J. Virol. 66: 5509-5515.

Genbank Accession No. M73260, 1996.

Graham, F. L. and L. Prevec. 1991. Manipulation of adenovirus vectors. In Murray E.J. (ed.), Methods in Molecular Biology. The Humana Press Inc. Clifton, N.J. vol. 7 (Gene Transfer Expression Protocols): 109-128.

Graham F. L. and L. Prevec. 1992. Adenovirus-based expression vectors and recombinant vaccines. in: Vaccines; New Approaches in Immunological Problems., ed. Ellis, R.W. Butterworth-Heinemann, Boston, MA: 363-390.

Graham F. L., J. Smiley, W. C. Russel and R. Naim. 1977. Characteristics of a human cell line transformed by DNA from human adenovirus type 5., J. Gen. Virol. 36: 59-72.

Gu, H., J. D. Marth, P.C. Orban, H. Mossmann and K. Rajewsky. 1994. Deletion of a DNA polymerase B gene segment in T cells using cell type-specific gene targeting. Science 265: 103-106.

Haj-Ahmad and Graham, "Characterization of an adenovirus type 5 mutant carrying embedded inverted terminal repeats," Virology, 153:22-34, 1986.

Kangegae Y., et al., "Efficient Gene Activation in Mammalian Cells by Using Recombinant Adenovirus Expressing Site-Specific CRE Recombinase," Nucleic Acids Research (1995) 23 (19) 3816-3821.

Kilby, N. J., M. R. Snaith, and J. A. H. Murray. 1993. Site-specific recombinases: tools for genome engineering. Trends Genet. 9: 413-421.

Metzger, D., J. Clifford, H. Chiba and P. Chambon. 1995. Conditional site-specific recombination in mammalian cells using a ligand-dependent chimeric Cre protein. Proc. Nat'l. Acad. Sci. USA 92: 6991-6995.

Pichel, J.G., Lakso, and H. Westphal. 1993. Timing of SV40 oncogene activation by site-specific recombination determines subsequent tumor progression during murine lens development. Oncogene 8: 3333-3342.

Sauer, B. 1994. Site-specific recombination: developments and applications. Cur. Opin. Biotech. 5: 521-527.

Sauer, Brian and Nancy Henderson. 1988. Site-specific DNA recombination in mammalian cells by the Cre recombinase of bacteriophage P1. Proc. Nat'l. Acad. Sci. USA 85: 5166-5170nn.

Sauer, B., and N. Henderson. 1990. Targeted insertion of exogenous DNA into the eukaryotic genome by the Cre recombinase. The New Biologist 2: 441-449.

Sauer, B., M. Whealy, A. Robbins and L. Enquist. 1987. Site-specific insertion of DNA into a pseudorabies virus vector. Nat'l. Adac. Sci. USA 84: 9108-9112.

Smith A. J. H., M. A. DeSousa, B. Kwabi-Addo, A. Heppel-Parton, H. Impey, and P. Rabbits. 1995. A site-directed chromosomal translocation induced in embryonic stem cells by Cre-loxP recombination. Nature Genetics 9: 376-385.

Sternberg, N., B. Sauer, R. Hoess, and K. Abremski. 1986. Bacteriophase P1 cre gene and its regulatory region; Evidence for multiple promotors and for regulation by DNA methylation., J. Mol. Biol. 187: 197-212.

Van Deursen, J., M. Fornerod, B. Van Rees, and G. Grosveld. 1995. Cre-mediated site specific translocation between non-homologous mouse chromosomes. Proc. Nat'l. Acad. Sci. USA 92: 7376-7380.

Mittal, S.K., McDermott, M.R., Johnson, D.C., Prevec, L. and F. L. Graham. 1993. Monitoring foreign gene expression by a human adenovirus-based vector using the firefly luciferase gene as a reporter, Virus Research, 28: 67-90.

Hanke, T., Frank L. Graham, Kenneth L. Rosenthal and David C. Johnson. 1991. Identification of an immunodominant cytotoxic t-lymphocyte recognition site in glycoprotein B of herpes simplex virus by using recombinant adenovirus vectors and synthetic peptides. 1991. J. of Virology, 65: 1177-1186.

Hearing, Patrick and Shenk, Thomas, 1983, "The Adenovirus Type 5 B1A Transcriptional Control Region Contains A Duplicated Enhancer Element." Cell:33 695-703.

Graham, F.L., 1987. Growth of 293 cells in suspension culture. J. Gen. Virol. 68: 937-940.

Meganuclease 1-Sec I (Omega-Nuclease) Boehringer Mannheim Catalog (2 pages).

Nicolas, Andrea et al., "Creation and Repair of Specific DNA Double-Strand Breaks In Vivo Following Infection with Adenovirus Vectors Expressing Saccharomyces Cerevisiae HO Endonuclease," Virology (2000) 266 (1): 211-224.

Quantin, B., Leslie D. Pericaudet, Shahragim Tajbakhsh and Jean-Louis Mandel. 1992. Adenovirus as an expression vector in muscle cells in vivo. Proc. Nat'l. Acad. Scie. 89: 2581-2584.

Rosenfeld, M.A. et al., 1992. In vivo transfer of the human cystic fibrosis transmembrane conductance regulator gene to the airway epithelium, Cell. 68: 143-155.

W. J. McGrory, D. S. Baulista and F. L. Graham. 1998. A simple technique for the resue of early region 1 mutations into infectious human adenovirus type 5, Virology 163: 614-617.

Wang, P., Anton, F. L. Graham and S. Bacchetti. High Frequency recombination between loxP sites in human chromosomes mediated by an adeniovorus vector expressing Cre recombinase. Somat Cell Mol Genet. Nov. 1995; 21(6):429-41.

Russ, Andreas P., et al., 1996,. Self-deleting Retrovirus Vectors for Gene Terapy, J. of Virology, pp. 4927-4932.

Xiao, Weidong et al., A Novel system to generate helper free gutless vectors. Abstract No. 133, p. 44, 1999 Keystone Symposium on Molecular and Cellular Biology of Gene Therapy.

Gudrun Schiedner, et al., 1998. Genomic DNA transfer with a high-capacity adenovirus vector results in improved in vivo gene expression and decreased toxicity. Nature Genetics 18: 180-183.

Manal A. Morsy, et al., 1998. An adenoviral vector deleted for all viral coding sequences results in enhanced safety and extended expression of a leptin transgene. Proc. Nat'l. Acad. Sci. USA 95: 7866-7871.

Stephen Hardy, et al., 1997. Construction of Adenovirus Vectors through Cre-lox Recombination. Jour. Virol. 71: 3 1842-1849.

Parks, et al., 1996. A helper-dependent adenovirus vector system: removal of helper virus by Cre-mediated excision of the viral packaging signal. Pro. Nat'l. Acad. Sci. USA 93: 13565-13470.

* cited by examiner

Construction of shuttle plasmids containing an SceI site
and internal ITR for the generation of new helper viruses

SEQUENCE OF SYNTHETIC OLIGONUCLEOTIDES USED IN VARIOUS CLONING PROCEDURES.

SceI site:

AB14265  5'- ACT TAA GCT AGG GAT AAC AGG GTA ATA TAG -3'  SEQ ID NO.: 1
AB14270  3'- TGA ATT CGA TCC CTA TTG TCC CAT TAT ATC -5'  SEQ ID NO: 2

Primers:

AB15136  5'- CGG ATC CAA GCT TGC GAG ATC GAA TTC-3'  SEQ ID NO.: 3

AB15137  5'- GCC TAG GTC GAC ACT CCG CCC TAA AAC-3'.  SEQ ID NO.: 4

AB15051  5'- GGA TAT CTG CAG ATC TAC TCC GCC CTA AAA C-3'  SEQ. ID NO.: 5

AB15052  5'- CCT CGA GTC GAC GCG AGA TCG AAT TC-3'  SEQ ID NO.: 6

AB14905  5'- GGG GGG TCA TGA AAA AGC CTG AAC TC-3'  SEQ ID NO.: 7

AB14906  5'- GGG GGG GTC GAC CAG ACC CCA CGC AAC G -3'  SEQ ID NO.: 8

Figure 4A

PCR Amplifications of Adenovirus Inverted Terminal Repeats

Construction of shuttle plasmids containing a floxed packaging signal, an SceI site, and internal ITR for the generation of new helper viruses

A

B

Construction of shuttle plasmids for helper virus rescue (cont'd)

Ad vectors expressing genes controlled by SceI-mediated excision and double strand break repair AdSceI/LacZ: defective viral vector expressing LacZ under control of a molecular switch

SceI cleavage and double strand break repair

βgal expression

SYSTEM FOR PRODUCTION OF HELPER DEPENDENT ADENOVIRUS VECTORS BASED ON USE OF ENDONUCLEASES

CROSS REFERENCES TO RELATED APPLICATIONS

This application is a continuation of application Ser. No. 09/883,649, filed on Jun. 19, 2001, now abandoned, which is a continuation of application Ser. No. 09/475,813, filed on Dec. 30, 1999, abandoned, which is a continuation-in-part of application Ser. No. 09/250,929, filed on Feb. 18, 1999, abandoned, which was a continuation-in-part of application Ser. No. 08/473,168, filed Jun. 7, 1995, now U.S. Pat. No. 5,919,676, which was a continuation-in-part of application Ser. No. 08/250,885(now U.S. Pat. No. 6,140,187), filed on May 31, 1994, which was a continuation-in-part of application Ser. No. 08/080,727, filed on Jun. 24, 1993, abandoned. Priority of each of these applications is claimed herein, and the disclosure of each of these applications is hereby incorporated by reference.

FIELD OF THE INVENTION

The invention is a new method of producing helper adenoviruses and helper-dependent adenovirus vectors (HDVs) in which helper virus is eliminated from HDV preparations by cleavage of the helper virus DNA with an endonuclease. The invention can be used independently of Cre/lox, or other helper virus containment systems, or in combination with Cre/lox, or other helper virus containment systems, to minimize the level of helper virus contamination of HDV preparations.

BACKGROUND OF THE INVENTION

In U.S. patent application Ser. No. 08/473,168, (the '168 application), published as WO96/40955, now U.S. Pat. No. 5,919,676, hereby incorporated by reference, a system for making helper-dependent adenovirus vectors and helper andenoviruses was disclosed. That system employed a recombinase, such as Cre, expressed by a cell into which a helper virus, comprising loxP sites flanking the adenovirus packaging signal, was introduced, (i.e. the packaging sequence was "floxed"). By virtue of the recombinase expressed by the host cell, the helper adenovirus packaging signal was excised, thereby restricting the packaging of the helper virus. Co-introduction of a helper-dependent, recombinant adenovirus vector (HDV) containing a packaging signal permitted isolation of efficiently packaged helper-dependent virus. However, as may be appreciated by those skilled in the art, any "leakage" of that system results in the contamination of helper-dependent adenovirus vector preparations with helper virus. The present invention is directed to methods and helper virus constructs, which result in production of HDV preparations wherein the level of packaged helper virus contamination is reduced by an endonuclease. The constructs and techniques taught herein may be employed independently from the Cre-loxP system described according to the WO96/40955 publication, or the techniques taught herein may be used to augment the effectiveness of that system.

Furthermore, those skilled in the art will appreciate, based on the disclosure provided herein, that a system such as that disclosed in parent application Ser. No. 08/719,217 (now U.S. Pat. No. 6,080,569), a foreign equivalent of which published as WO98/13510, hereby incorporated by reference, maybe augmented by the system disclosed and claimed herein. In the WO98/13510 system, a helper adenovirus was described wherein the pIX gene was deleted or disabled. In such a modified adenovirus, a genome greater than about 35 kb is not efficiently packaged, irrespective of the presence or absence of a functional packaging signal, $\psi$, unless the helper virus is propagated in a cell which complements the pIX deficiency. In combination with the present invention, a doubly or triply disabled helper virus is produced, if the Cre/loxP recombination system is also used, which is still capable of providing, in trans, all of the functions necessary to support replication of a helper-dependent adenovirus vector (HDV).

Those skilled in the art are familiar with endonucleases and the use of such compositions, whether expressed endogenously or introduced from an external source, in the cleavage of specific target sequences in a segment of nucleic acid.

Those skilled in the art will also appreciate that adenoviruses contain inverted terminal repeats (ITRs) at each end of the genome, which are essential to replication of adenoviruses. The ITRs (representing the most terminal approximately 100–200 bp of the viral genome) are the only Ad DNA sequences needed in cis for viral DNA replication, and the packaging signal ($\psi$), which is needed for packaging of viral DNA into virion capsids, is the only additional cis acting sequence needed for production of virions. Thus, appropriate helper viruses may be used to provide, in trans, all other factors required for replication of the HDV. Furthermore, it is known that adenoviruses containing an ITR embedded within the genome are capable of replicating, through a repair process, even though an external ITR is eliminated (see, for example, Haj-Ahmad and Graham, Virology 153:22–34, 1986). What has not been previously demonstrated, however, is the application of this observation in the production of helper viruses and helper dependent virus preparations substantially free of helper virus contamination.

SUMMARY OF THE INVENTION

The present invention relates to methods for efficient and reliable construction of adenovirus vectors that contain and express foreign DNA and are useful for gene transfer into mammalian cells, for vaccines and for gene therapy. The invention provides for the growth and purification of adenovirus vectors (helper dependent vectors or HDVs) from which all or most of the viral genes have been removed. The vector system described herein is a new method designed to eliminate helper viruses from the final HDV preparation by cleavage of the helper virus DNA with an endonuclease.

Accordingly, it is one object of this invention to provide a simple and useful system whereby helper dependent adenovirus vectors may be propagated and purified and wherein contamination with helper virus is significantly reduced or eliminated.

Another object of this invention is to provide a method whereby reduction of helper adenovirus contamination of helper-dependent adenovirus vector preparations is achieved or augmented.

Another object of this invention is to provide a preparation of helper-dependent adenovirus vector substantially free of helper virus, such that the helper-dependent vector preparation is substantially free of virus capable of replicating in host cells into which the vector is introduced.

Another object of this invention is to provide methods and compositions of enhanced utility for vaccine and gene therapeutic applications.

Other objects of this invention will be apparent from a review of the complete disclosure and from the appended claims.

BRIEF DESCRIPTION OF THE DRAWINGS

FIG. 4a illustrates the sequences of oligonucleotides used in various cloning procedures.

Figure 22A:
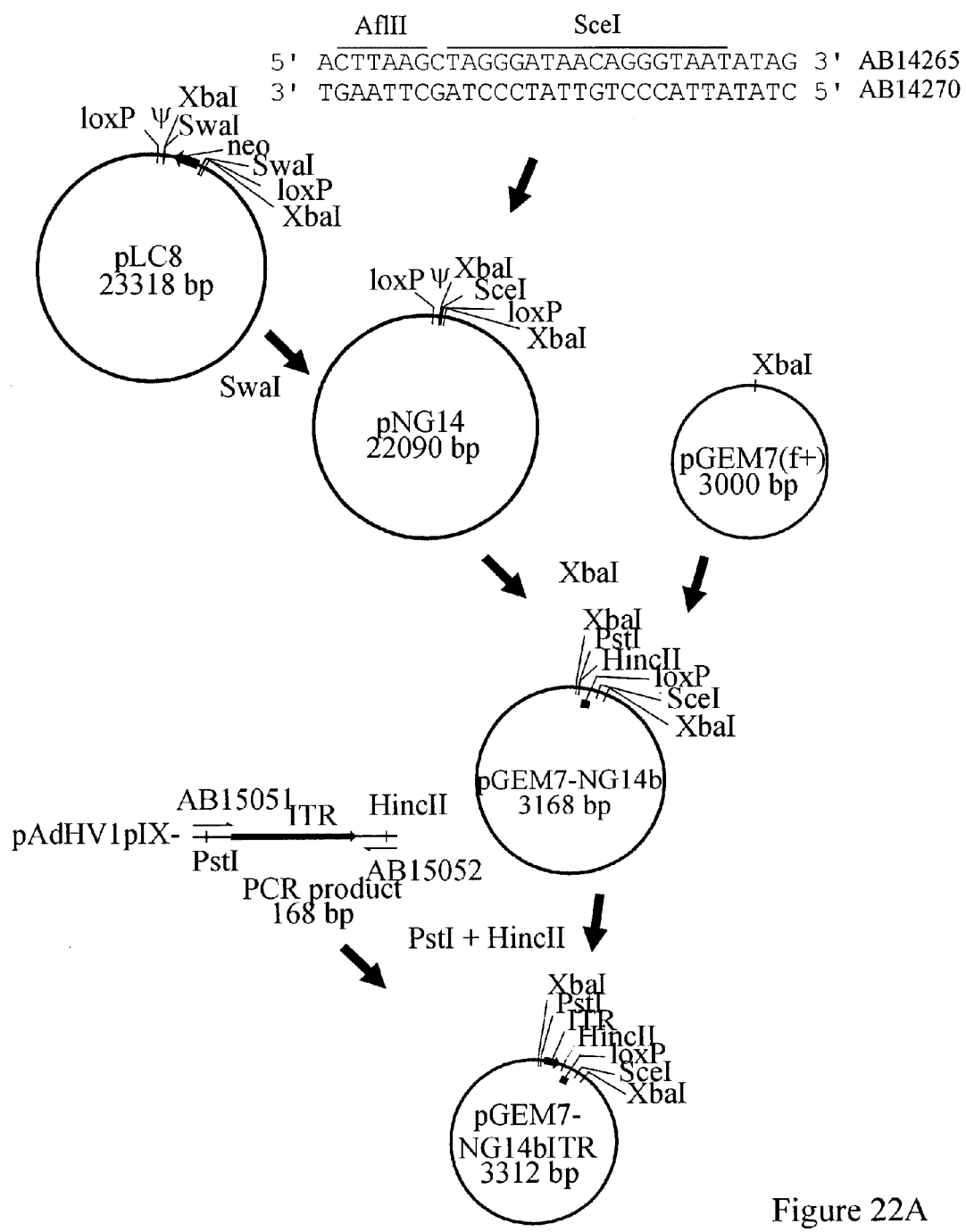
FIG. 22. Construction of shuttle plasmids for rescue of helper viruses bearing sites. (A) An oligonucleotide bearing the I-SceI recognition sequence (SEQ. ID. NO.:1, AB14265+SEQ. ID. NO.:2, AB14270, SEQ ID NO: 19 and SEQ ID NO: 20) was inserted into the SwaI sites of pLC8 (Parks et al., 1996) replacing the neomycin phosphotransferase gene to generate pNG14. The 168 bp XbaI fragment bearing the SceI and loxP sites from pNG14 was cloned into the XbaI site of pGEM7(f+) (Promega) to generate pGEM7-NG14b. An ITR was PCR amplified from pAdHV1pIX-(gift from Andy Bett) with primers AB15051 (5' GGATATCTG-CAGATCTACTCCGCCCTAAAAC 3', SEQ ID NO: 5) and AB15052 (5'CCTCGAGTCGACGCGAGATCGAATTC 3', SEQ ID NO: 6). The PCR product was disgested with PstI and HincII and the 168 bp fragment was cloned into the PstI and HincII sites of pGEM7-NG14b to generate pGEM7-
Figure 22B:
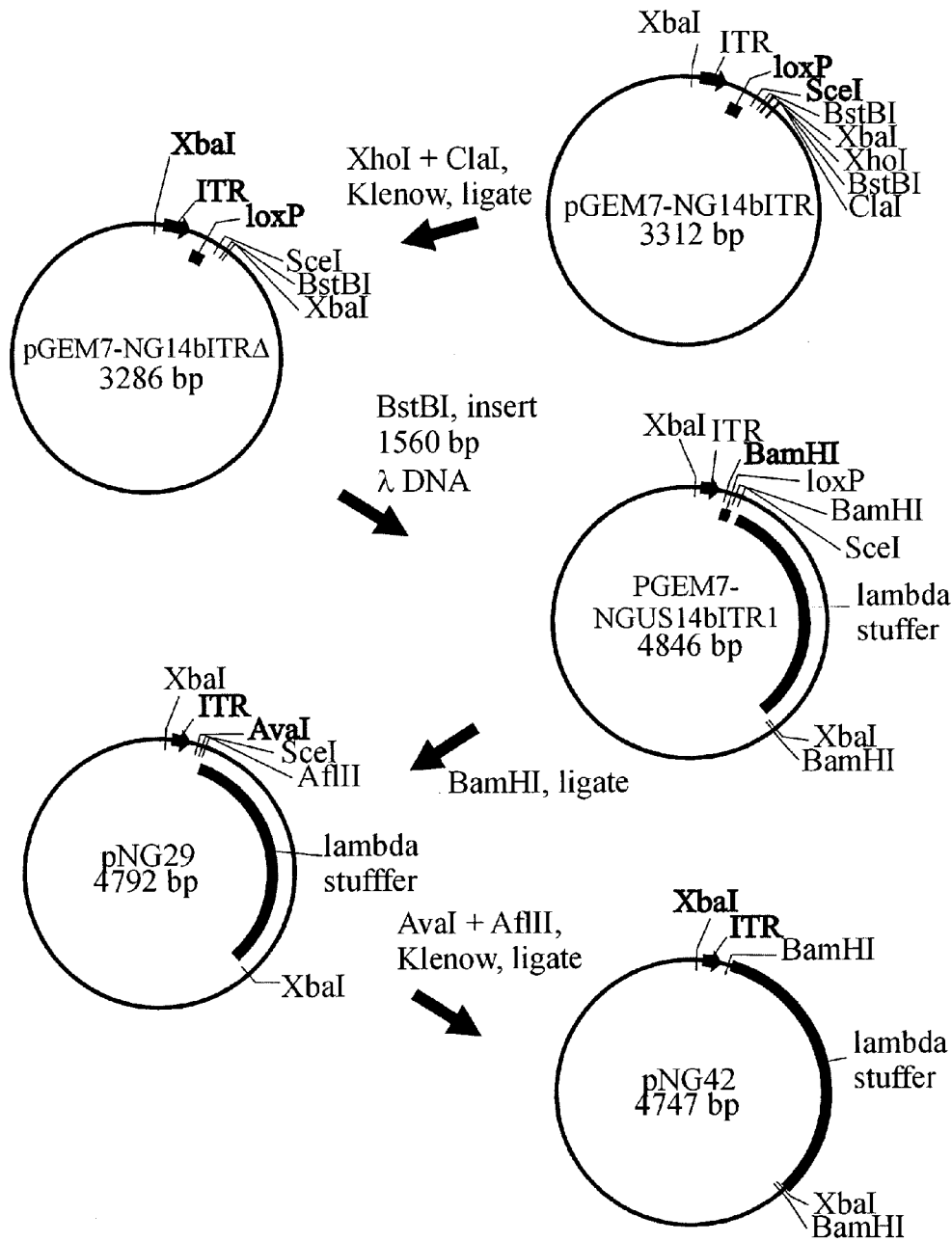
Figure 22C:
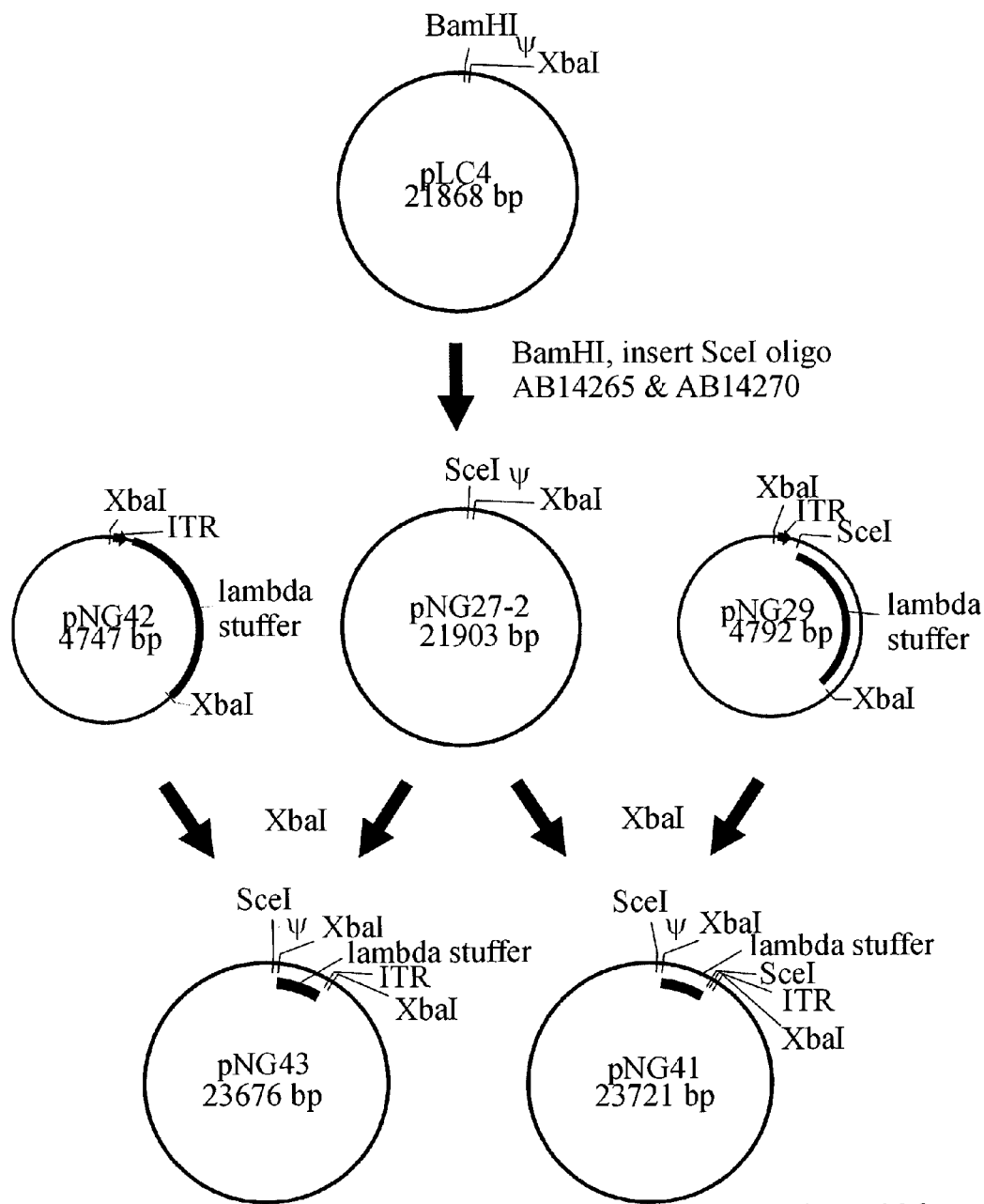
Figure 22D:
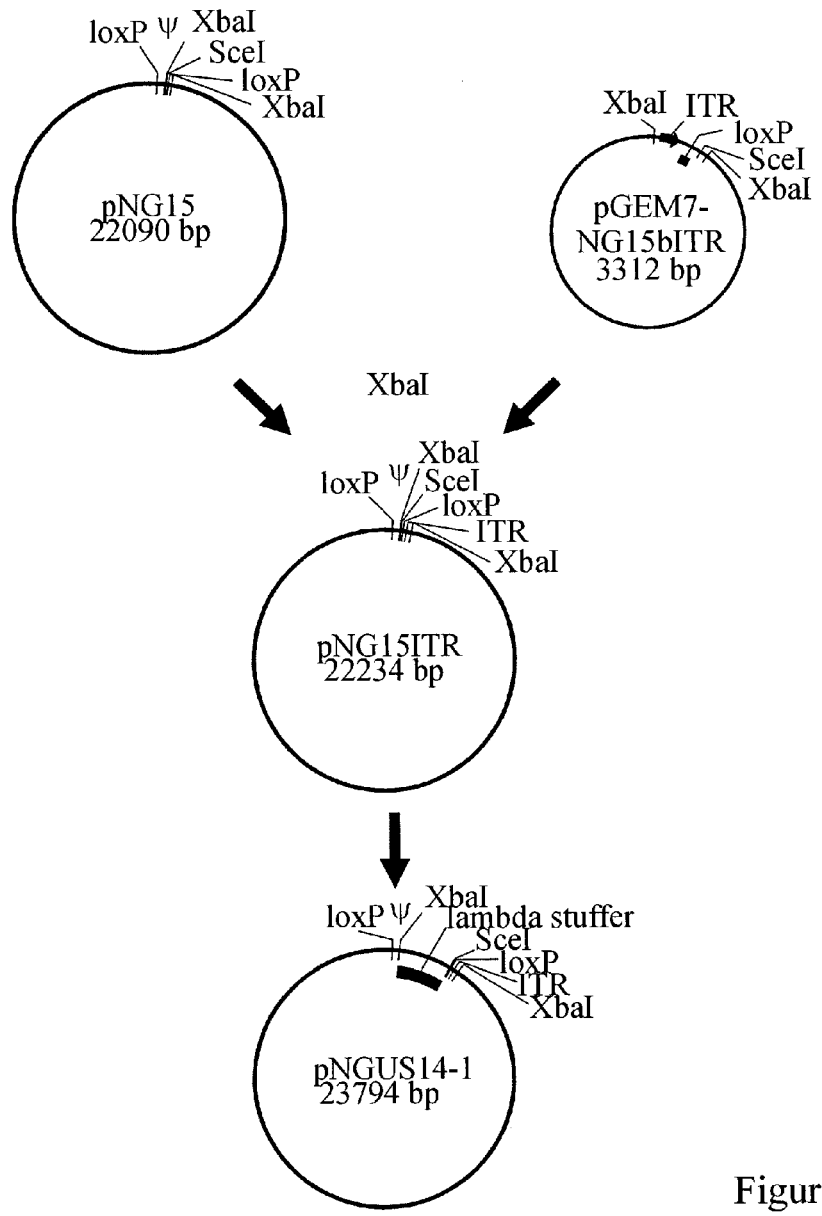

NG14bITR. (B) The plasmid pGEM7-NG14bITR was digested with XhoI and ClaI, Klenow end modified and self ligated to generate pGEM7-NG14bITRΔ which bears a unique BstBI site. The 1560 bp BsaHI fragment from lambda DNA was inserted into the BstBI site of pGEM7-NG14bITRΔ to generate pGEM7-NGUS14bITR1. The loxP site was removed from pGEM7-NGUS14bITR1 by BamHI digestion followed by ligation to generate pNG29. The SceI site was removed from pNG29 by AvaI and AflII digestion, Klenow end modification, followed by self ligation to generate pNG42. (C) The plasmid pNG27-2 was generated by inserting an oligonucleotide bearing the SceI site (SEQ. ID. NO.:1, AB14265+SEQ. ID. NO.:2, AB14270) into the BamHI site of pLC4. The plasmid pNG41 was generated by inserting the 1818 bp XbaI fragment from pNG29 into the XbaI site of pNG27-2. pNG41 was used to generate the helper virus AdNGUS41 by in vivo homologous recombination following cotransfection into 293 cells with pUMA71 (Parks et al., 1996). The plasmid pNG43 was generated by inserting the 1773 bp XbaI fragment from pNG42 into the XbaI site of pNG27-2. pNG43 was used to generate the helper virus AdNGUS43 by in vivo homologous recombination following cotransfection into 293 cells with pUMA71. (D) The plasmid pNG15ITR was constructed by replacing the 168 bp XbaI fragment in pNG15 with the 312 bp XbaI fragment from pGEM7-NG15bITR. The plasmid pNG15 was constructed in the same way as pNG14 (see FIG. 22A) and differs from pNG14 only in the orientation of the SceI oligo. The plasmid pGEM7-NG15bITR was constructed in the same way as pGEM7-NG14bITR (see FIG. 22A) and differs from pGEM7-NG14bITR only in the orientation of the SceI oligo. The helper virus AdNG15ITR (FIG. 19) was generated by in vivo homologous recombination between pNG15ITR and pUMA71 following their cotransfection into 293 cells. The plasmid pNGUS 14-1 was constructed by replacing the 312 bp XbaI fragment in pNG15ITR with the 1872 bp XbaI fragment from pGEM7-NGUS14bITR1 (FIG. 22B). The helper virus AdNGUS14-1 (FIG. 19) was generated by in vivo homologous recombination between pNGUS14-1 and pUMA71 following their cotransfection into 293 cells.

Figure 23:
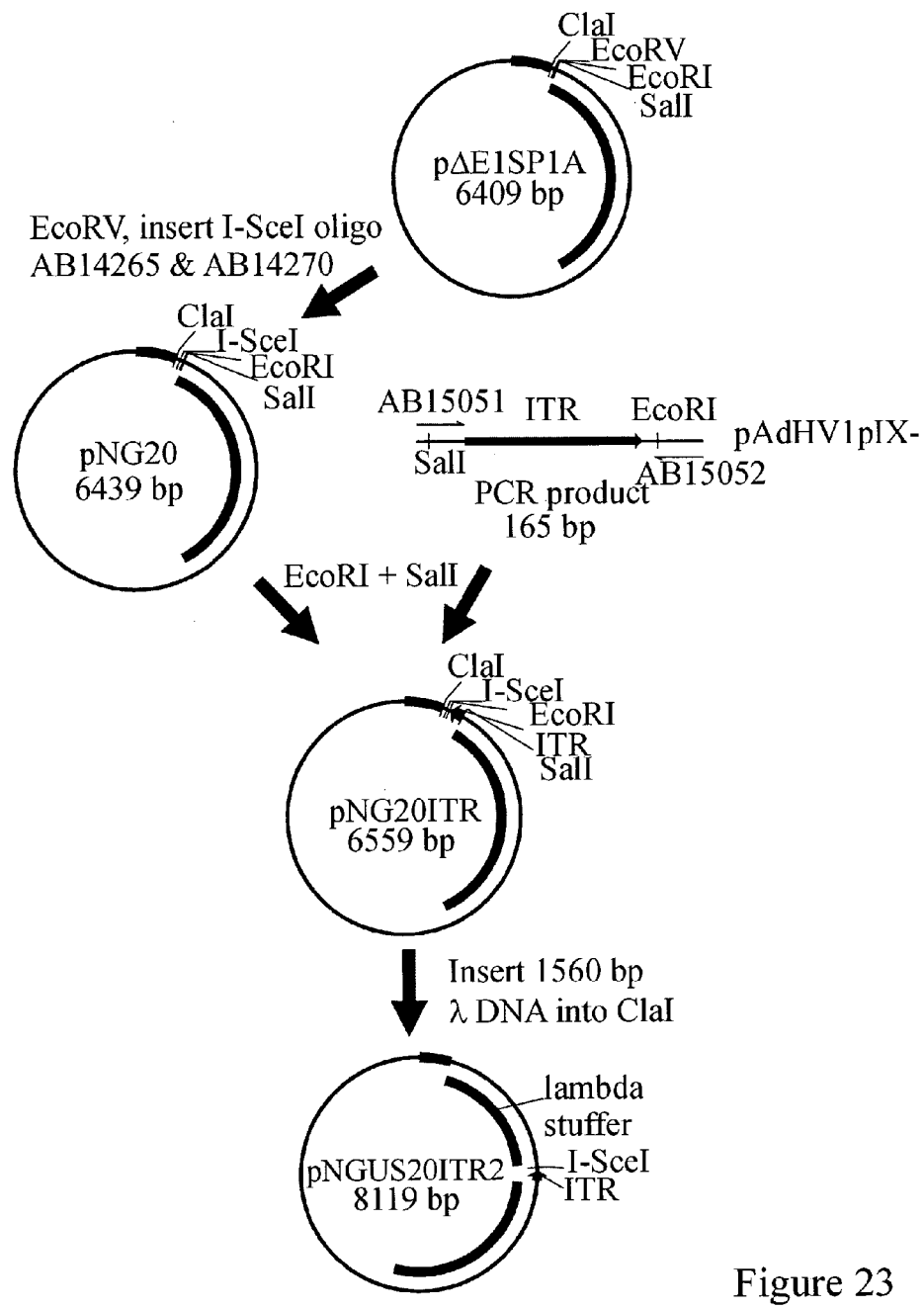

FIG. 23. Construction of the shuttle plasmid for rescue of helper viruses bearing an I-SceI site. An oligonucleotide bearing the SceI site (SEQ. ID. NO.:1, AB14265+SEQ. ID. NO.:2, AB14270) was inserted into the EcoRV site of pΔE1SP1A to generate pNG20. An ITR was PCR amplified from pAdHV1pIX—with primers AB15051 and AB15052. The PCR product was digested with SalI and EcoRI and the 165 bp fragment was cloned into the SalI and EcoRI sites of pNG20 to generate pNG20ITR. The 1560 bp BsaHI fragment from lambda DNA was inserted into the ClaI site of pNG20ITR to generate pNGUS20ITR2. The helper virus AdNGUS20ITR2 was generated by in vivo homologous recombination between pNGUS20ITR2 and pUMA71 following their cotransfection into 293 cells.

Figure 21:
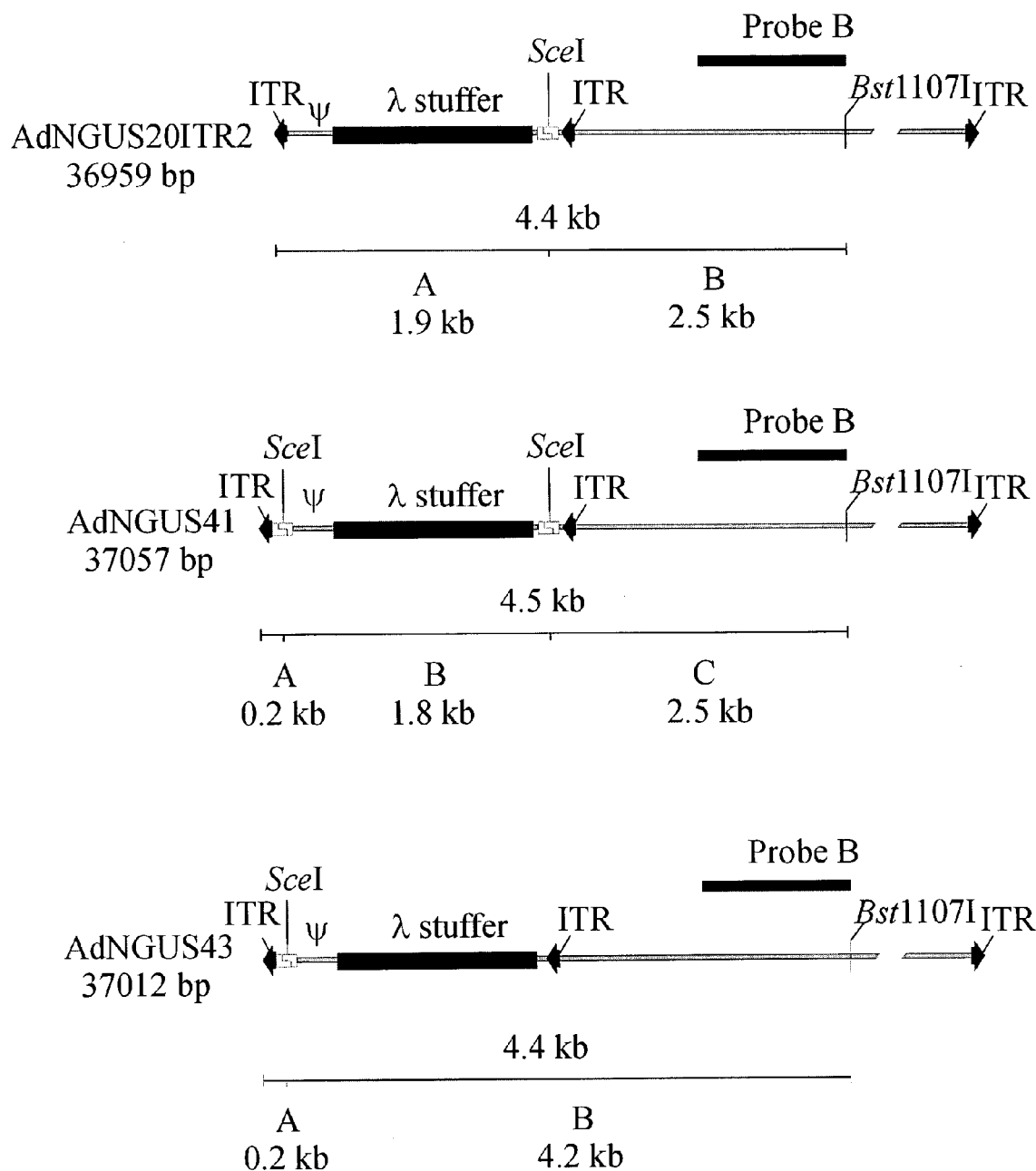
FIG. 21. Helper viruses with one or two SceI recognition sites. The helper viruses AdNGUS20ITR2, AdNGUS41 and AdNGUS43 are identical except for the number and position of the I-SceI recognition site(s). Essential features common to these viruses include an internal ITR to permit viral DNA replication of I-SceI cleaved helper genome DNA and a 1560 bp fragment of bacteriophage λ DNA inserted between the two left end ITRs to prevent packaging of rearranged viral genomes that are generated by panhandle formation using the internal ITR during DNA replication. AdNGUS20ITR2 contains a single SceI site located between the λ DNA stuffer and the packaging signal (ψ). AdNGUS41 contains two SceI sites flanking ψ and the λ DNA. AdNGUS43 contains a single SceI site located between the leftmost ITR and the λ DNA stuffer.
Figure 24:
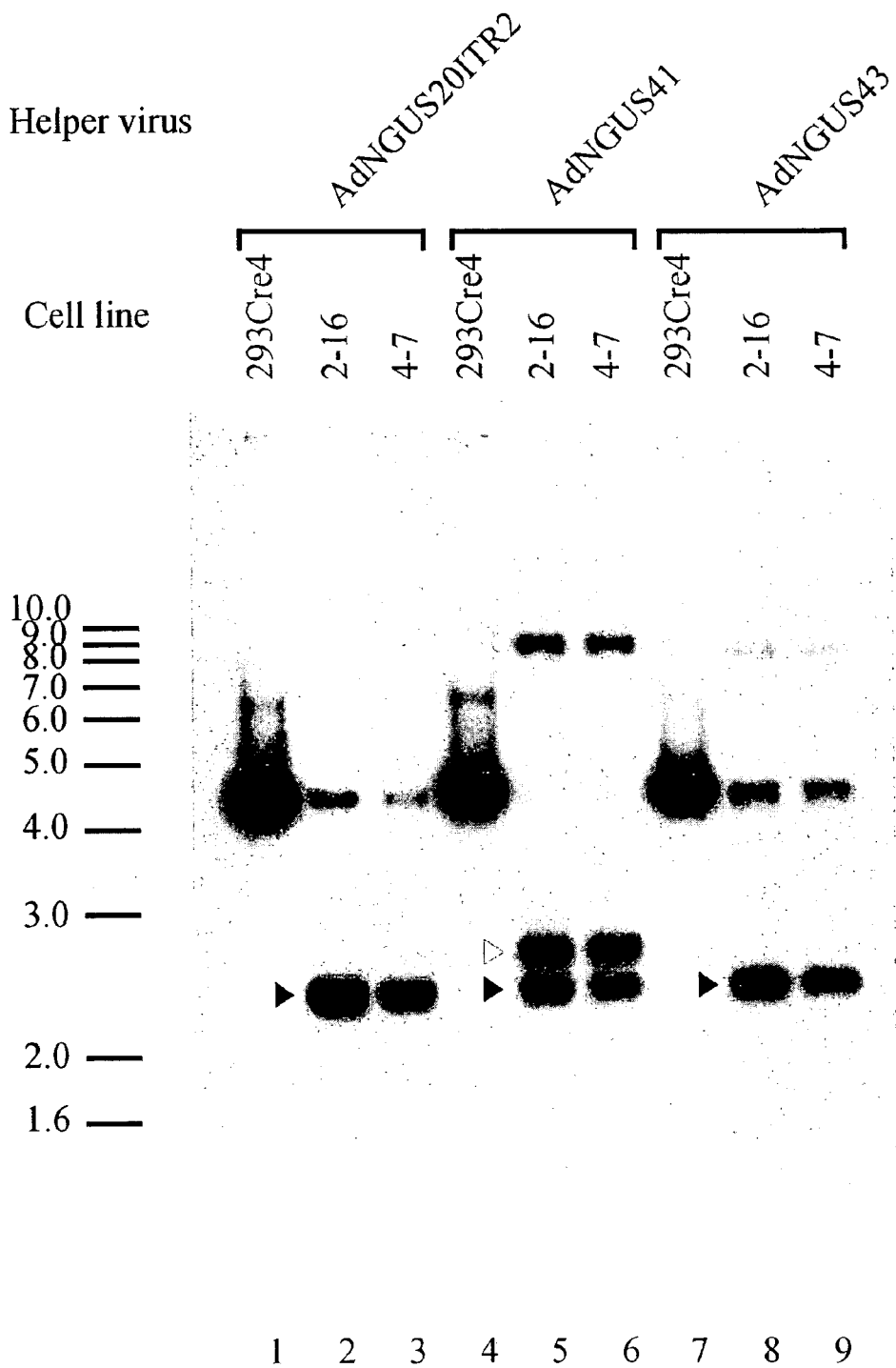
Figure 26:
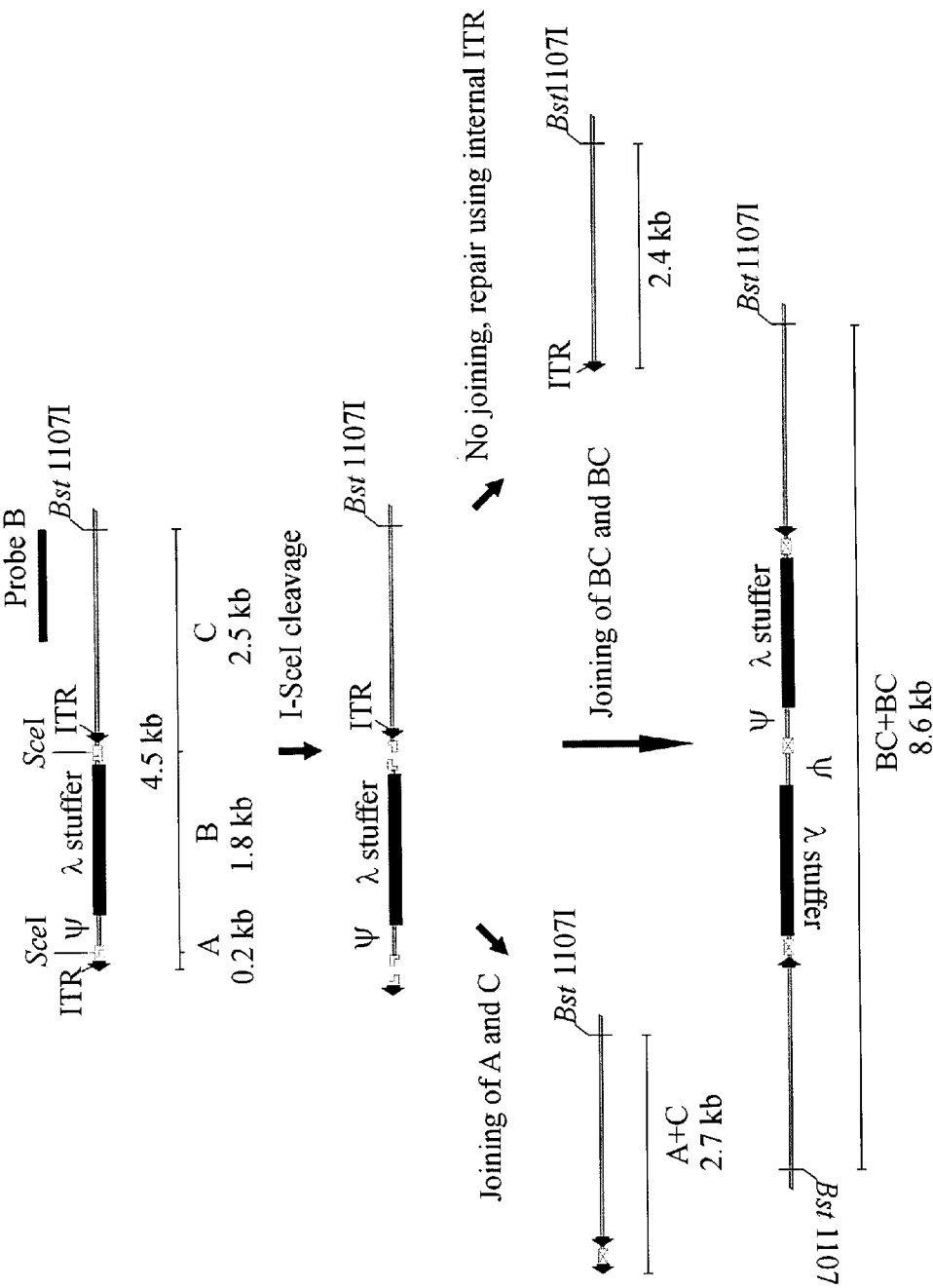
Figure 27:
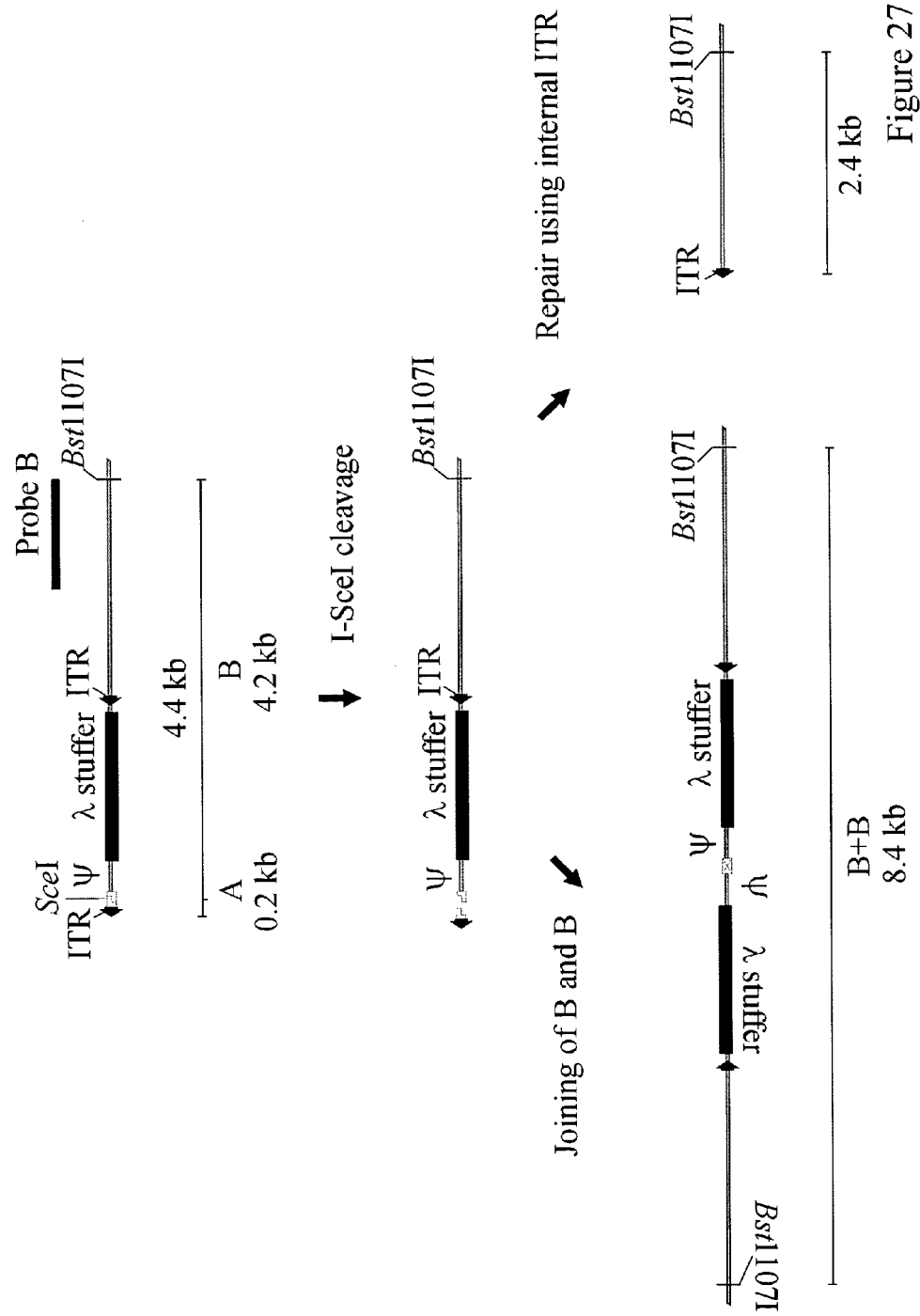

FIG. 24. Southern analysis of viral DNA extracted from 293SceI cells infected with various helper viruses illustrating the efficiency of I-SceI cleavage in vivo and generation of variant viral DNA molecules. Cultures of the indicated cell lines (the parental 293Cre4 cell line and the I-SceI expressing 293Cre4 derivatives, 2–16 and 4–7) in 35 mm dishes were infected with the various helper viruses bearing SceI recognition sites as illustrated in FIG. 21 at an moi of 1. At 48 hrs post-infection, viral DNA was extracted and analyzed by Southern blot hybridization with probe fragment B (see FIG. 21) following digestion with Bst1107I. For the viruses AdNGUS20ITR2, AdNGUS41 and AdNGUS43, Bst1107I cleavage is expected to generate fragments with molecular weights 4.4 kb, 4.5 kb and 4.4 kb, respectively, in the absence of I-SceI cleavage (FIG. 21). Following I-SceI cleavage, these fragments are all expected to be converted to a 2.4 kb Bst1107I fragment (indicated by the black triangles) as a result of panhandle repair using the internal ITR during DNA replication. However, in the case of AdNGUS41 and AdNGUS43, but not AdNGUS20ITR2, an unexpected band of ~8.4 to 8.6 kb (indicated by the white circles) is present following infection of I-SceI expressing cells. One feature common to both AdNGUS41 and AdNGUS43, but not AdNGUS20ITR2, is the presence of an SceI site to the left of ψ. As illustrated in FIGS. 26 and 27, this feature may account for the presence of the novel ~8.4 to 8.6 kb band. Furthermore, in the case of AdNGUS41, an unexpected band of ~2.7 kb is also present (indicated by the white triangle). A possible mechanism responsible for the presence of this band is presented in FIG. 26.

Figure 12A:
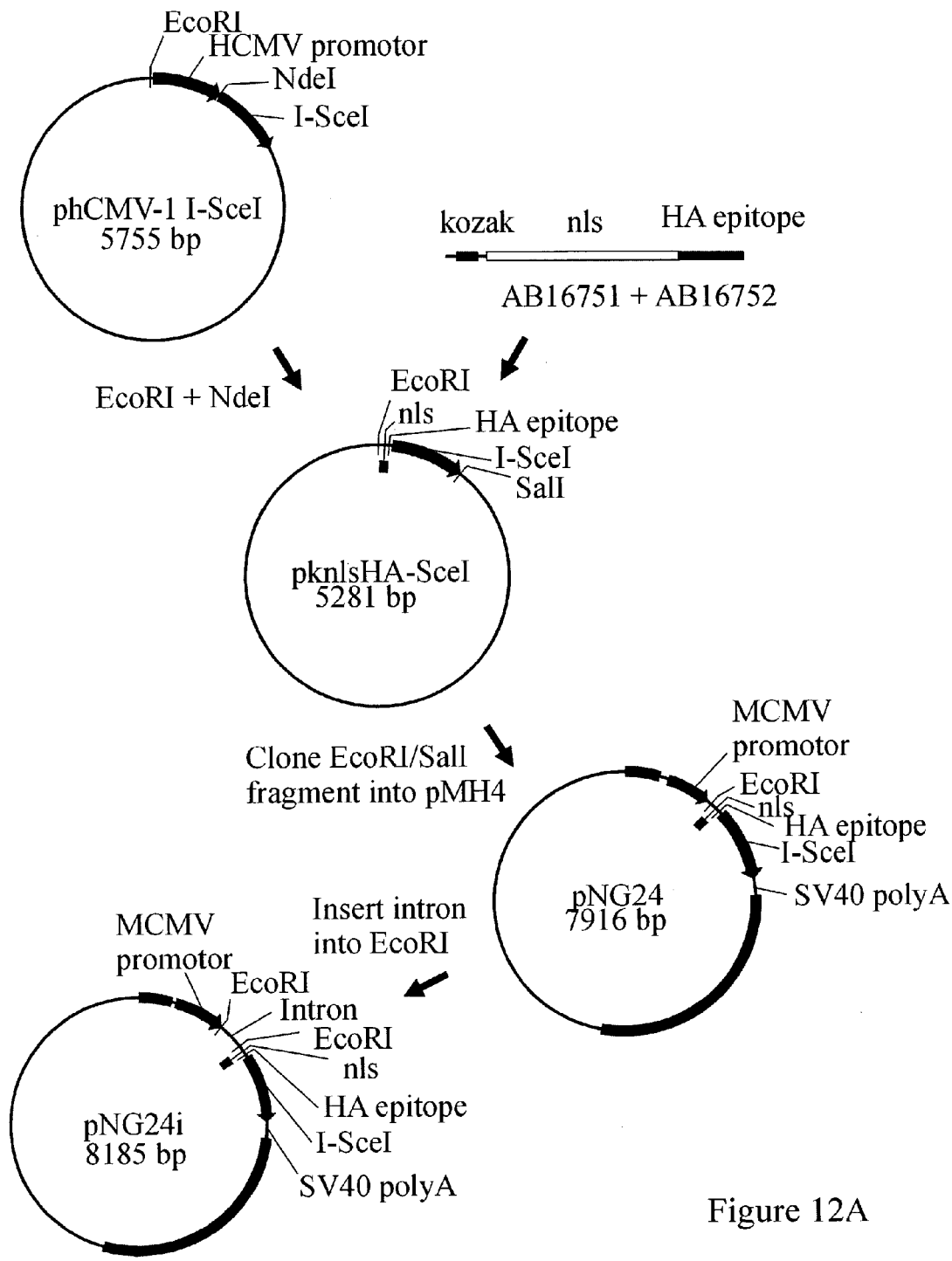
FIG. 12. Construction of a plasmid for generation of cell lines stably expressing I-SceI. (A) An oligonucleotide (AB16751: 5' AATTCGCCGCCGCCATGGGATCATCAT-CAGACG ACGAAGCAACAGCAGACGCACAACACG-CAGCACCACCAAAAAAAAAAACGAAAAGTAG AAGACCCACGATTTATGTACCCATAC-GATGTTCCTGACTATGCGGG 3' (SEQ ID NO:17)+ AB1675:5'TACCCGCCATAGTCAGGAACATCG-TATGGGTACATAAATCGTGGGTCTTCTACT TTTCGTTTTTTTTTGGTGGTGCTGCGT-GTTGTGCGTCTGCTGTTGCTTCGTCGTCTGATG ATGATCCCATGGCGGCGGCG 3' (SEQ ID NO:18) bearing a Kozak consensus sequence, a nuclear localization signal (nls) and an influenza hemagglutinin (HA) epitope was inserted into the EcoRI and NdeI sites of phCMV-1 I-SceI (Choulika et al., 1995 MCB 15:1968) replacing the hCMV promotor to generate pknlsHA-SceI. The 849 bp EcoRI/SalI fragment from pknlsHA-SceI was inserted into the EcoRI/SalI sites of pMH4 (Addison et al., 1997) to generatepNG24. The 269 bp EcoRI fragment from pMH4(I), bearing an intron (Mathews et al., 1999), was inserted into the EcoRI site of pNG24 to generate pNG24i. The virus AdNGUS24i was generated by in vivo homologous recombination between pNG24i and pJM17 following their cotransfection into 293 cells. (B) The 980 bp PacI/BstEII fragment from pNG24i was cloned into the PacI and BstEII sites of pNG19 to generate pNG26i. Cell lines stably expressing I-SceI were generated by transfection of 293Cre4 cells with pNG26i.
Figure 12B:
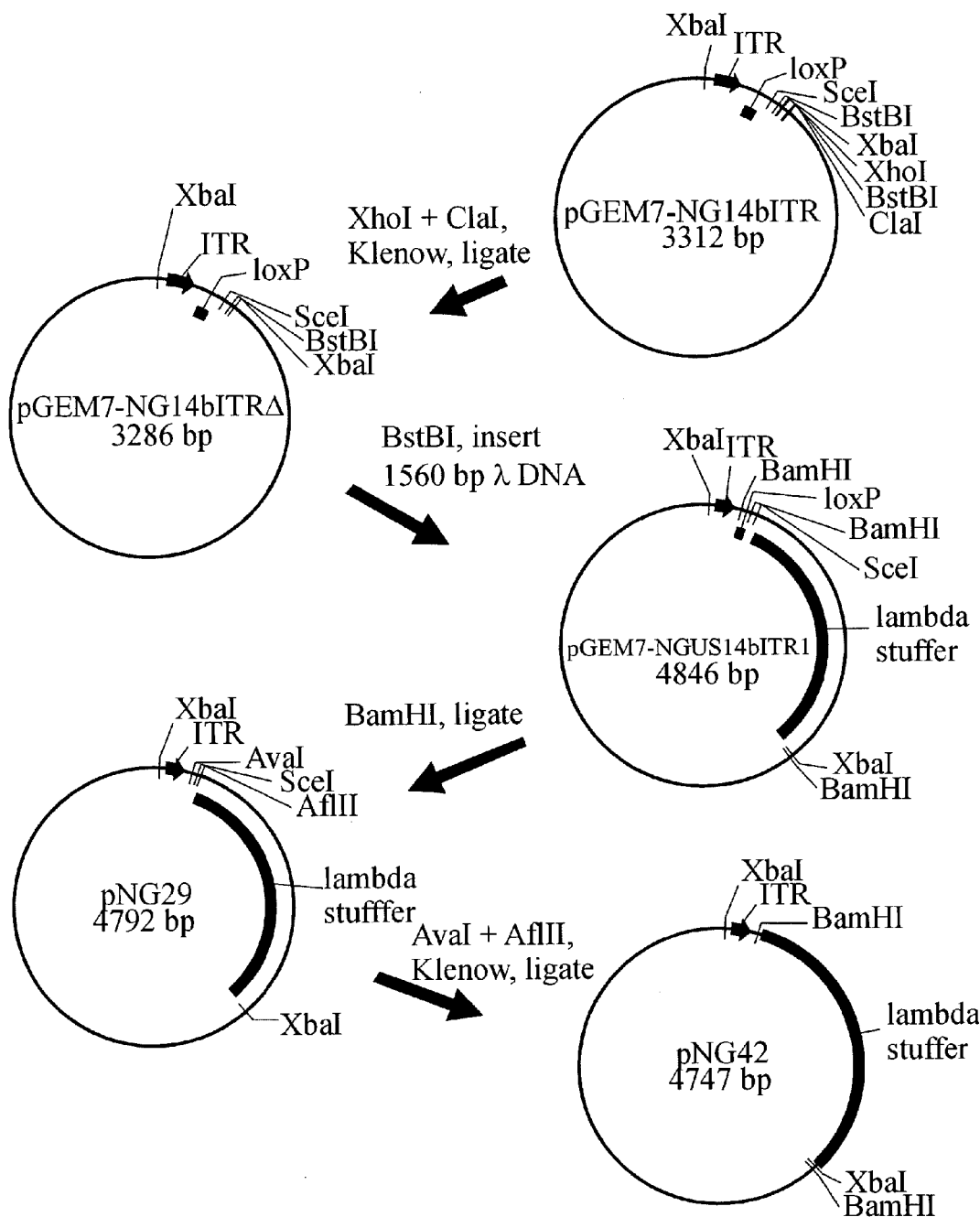
Figure 25:
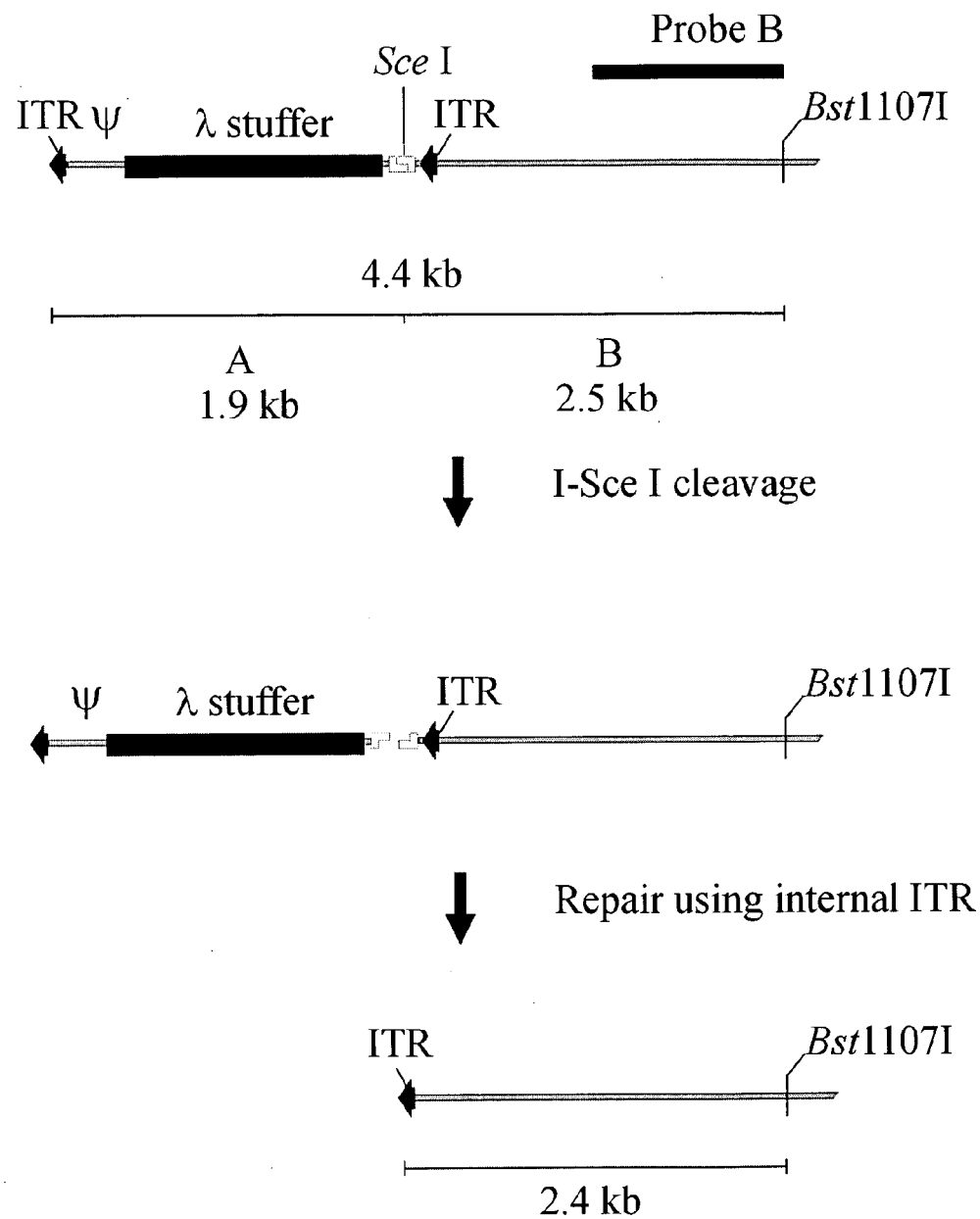

FIG. 25. Illustration of in vivo I-SceI cleavage and rearrangement of AdNGUS20ITR helper virus genome following infection of 293Cre cells expressing SceI. I-SceI cleavage of AdNGUS20ITR2 renders the genome unpackagable due to the removal of ψ. The resulting genome can still replicate, and hence provide helper functions, by panhandle formation using the internal ITR. This process results in a viral genome that, following Bst1107I digestion and Southern blot hybridization, produces the fragment indicated by the black triangle in FIG. 12. It can be seen that cleavage by I-SceI and use of an internal ITR to generate a replicating viral DNA is highly efficient as there is relatively little of the parental 4.4 kb band remaining.

FIG. 26. Illustration of in vivo I-SceI cleavage and rearrangement of AdNGUS41 helper virus genome following infection of 293Cre cells expressing I-SceI. I-SceI cleavage of AdNGUS41 results in three fragments. Panhandle repair using the internal ITR allows the genome to replicate and provide helper functions but the resulting genome is unable to be packaged due to the absence of ψ (right part of Figure). Bst1107I digestion results in a 2.4 kb fragment (black triangle in FIG. 24). The unexpected 2.7 kb band shown in lanes 5 and 6 of FIG. 24 (indicated by the white triangles) can arise as a consequence of the joining of fragments A and C following I-SceI cleavage. An SceI site is unlikely to be recreated by this joining due to the incompatibility of the two half-sites, rendering this species resistant to recleavage by I-SceI which may account for the relatively high intensity of the 2.7 kb band. The unexpected ~8.6 kb band seen in FIG. 24 (indicated by the white circles in lanes 5 and 6) can be generated by the joining of fragments B and C of one genome to the same fragments of another genome. The relatively high intensity of this band suggests that it does not contain any SceI sites. Because repair of double strand breaks, which this process exemplifies, frequently results in loss of a few nucleotides, loss of the SceI sites is not unexpected. The resulting DNA molecule indicated at the bottom of the Figure, can replicate and thus provide helper functions, but, while it retains ψ, it is not expected to be packageable due to the distance of ψ from the genome terminus. I-SceI cleavage and fragment rejoining is surprisingly efficient as can be seen from the intensities of the various bands on the Southern blot. It can be seen that there is almost no parental, unprocessed viral DNA in lanes 5 and 6 (no band at 4.4–4.5 kb), indicating that packageable parental viral genomes have been virtually 100% eliminated. Thus a helper virus with a packaging signal flanked by SceI sites and optionally with an internal ITR may be a preferred embodiment.

FIG. 27. Illustration of in vivo I-SceI cleavage and rearrangement of AdNGUS43 helper virus genome following infection of 293Cre cells expressing I-SceI. I-SceI cleavage of AdNGUS43 renders it noninfectious due to its inability to replicate in the absence of a terminal left end ITR. Viral DNA replication, but not packaging, can be restored following panhandle formation using the internal ITR. The unexpected band of ~8.4 kb shown in FIG. 24 (indicated by the white circles in lanes 8 and 9) can be generated by joining of fragment B of one cleaved genome with the same fragment from another cleaved genome. This species likely lacks an SceI site. The viral DNA molecule generated by head to head joining can replicate but, as with the similar species illustrated in FIG. 26, is unable to package because only packaging signals located near the ends of viral DNA molecules are functional.

Figure 28:
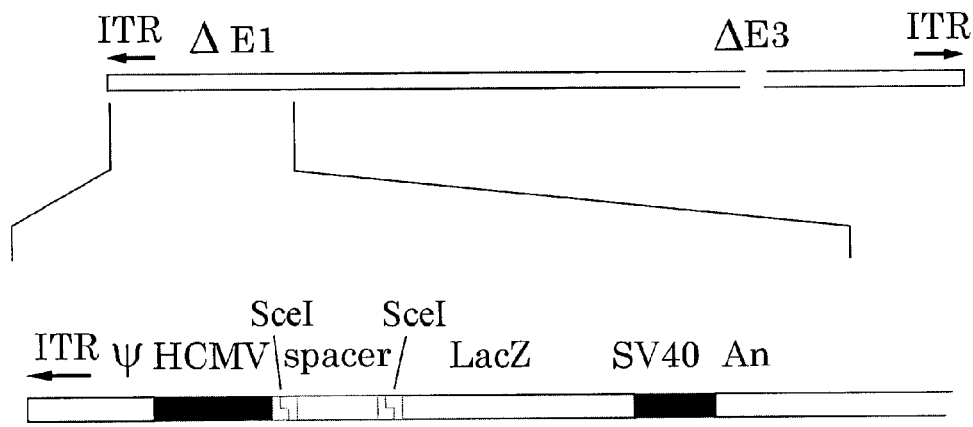
Figure 28:
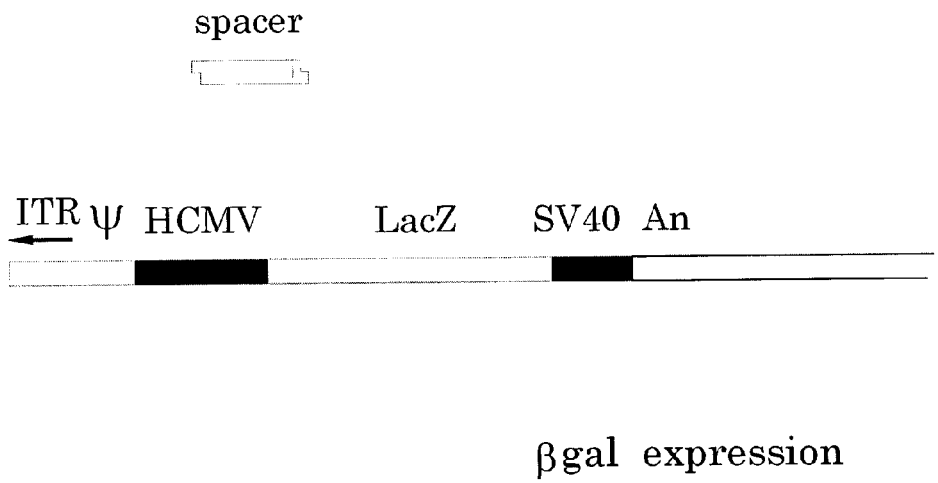

FIG. 28. Illustration of I-SceI cleavage and double strand break repair to regulate gene expression from a molecular switch in an Ad vector. An Ad vector can be readily constructed wherein a cDNA is separated from a promoter by a spacer DNA that blocks expression of the cassette and wherein the spacer DNA is flanked by SceI sites. I-SceI mediated cleavage and joining of the left and right fragments of the viral DNA as illustrated effectively results in excision of the spacer and a switch on of expression, of β-galactosidase in the example shown here.

Figure 29:
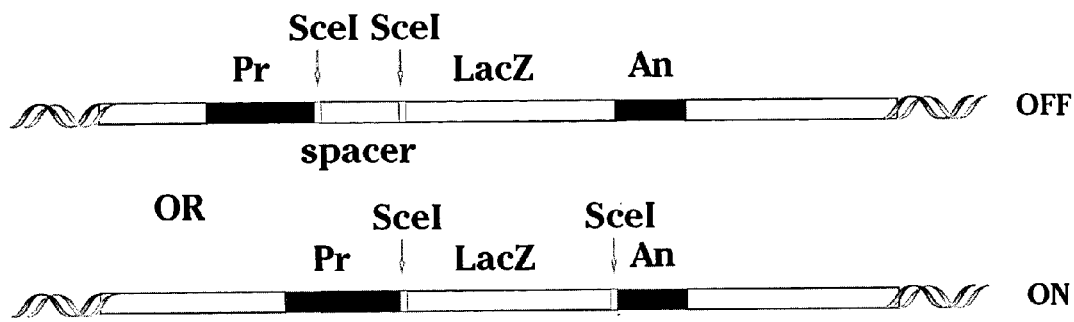
Figure 29:
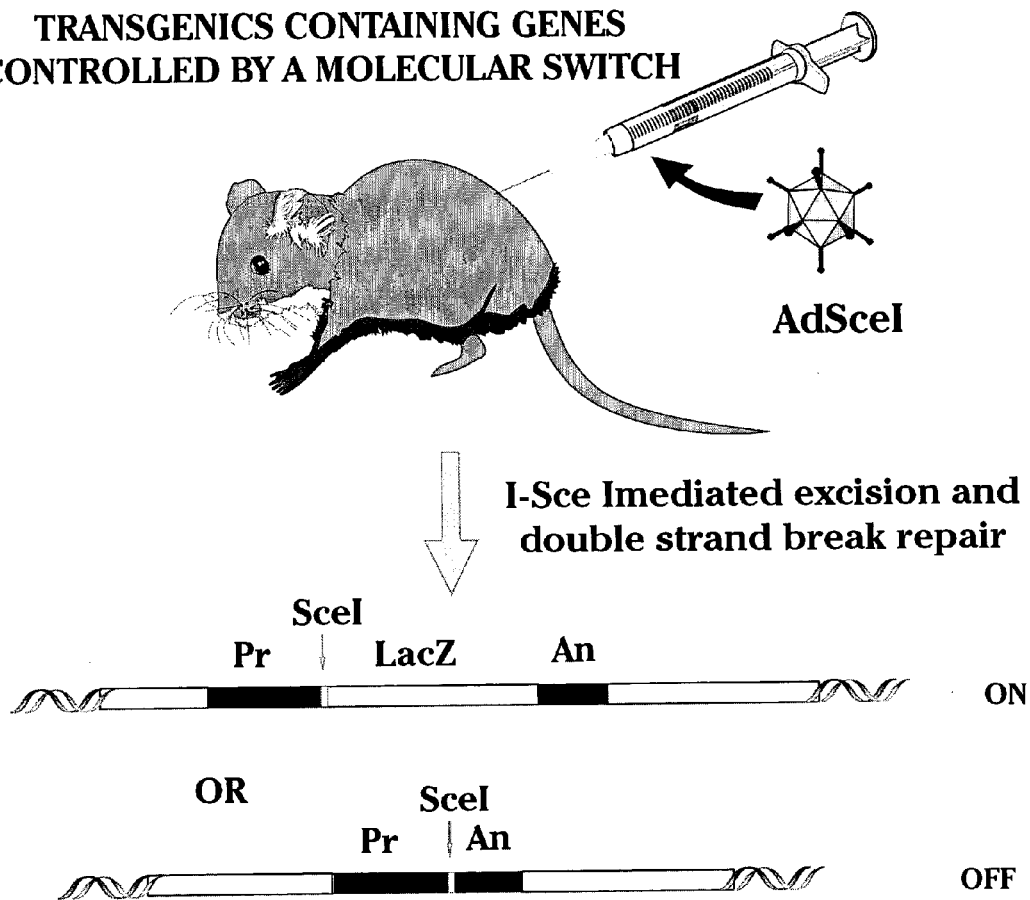

FIG. 29. Illustration of control of gene expression in cells of a transgenic animal by an I-SceI dependent molecular switch. Expression cassettes can be readily engineered in cells or in transgenic animals such that gene expression from said cassettes can be regulated by I-SceI mediate DNA cleavage and subsequent double strand break repair. Such "molecular switches" can be designed such that gene expression is switched on or switched off depending on the placement of the I-SceI recognition sites. For example an expression cassette can be introduced into cells or animals such that expression of a protein encoding, for example, β-galactosidase, is blocked by positioning a spacer DNA between a promoter and the coding sequences for said protein. I-SceI mediated excision and subsequent double strand break repair results in excision of the spacer and a switch on of expression. Alternatively, the cDNA encoding, for example β-galactosidase, could be flanked by SceI sites so that SceI mediated DNA cleavage and double strand break repair results in a switch off of expression. Not meant to be limiting as there are many ways to introduce SceI sites into cellular DNA such that SceI mediated cleavage and DNA fragment rejoining will result in rearrangements of DNA that regulate gene expression. For example endogenous genes such as those encoding oncogenes, tumor suppressor genes, genes encoding various proteins such as cytokines, enzymes and the like may be regulated by the methods described herein.

Figure 30:
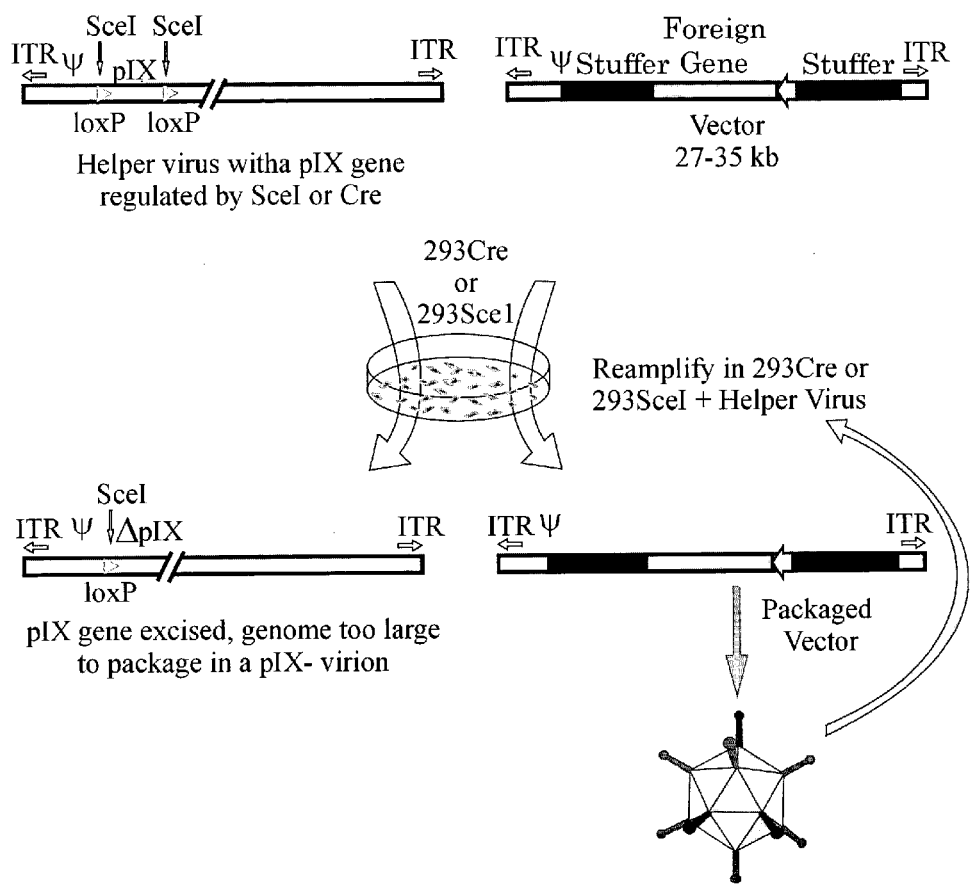

FIG. 30. Use of SceI cleavage and double strand break repair or Cre-lox mediated excision for production of helper dependent vectors in a pIX based system. In this example pIX coding sequences of a helper virus are flanked by either SceI sites or lox sites such that upon infection of cells expressing I-SceI or Cre recombinase, respectively, the pIX gene is excised resulting in abolition of pIX expression. A consequence is that the packaging capacity of the resulting virions (lacking pIX) is diminished so that the helper virus genome is unable to package into virions. In contrast, the helper dependent vector genome is designed to be sufficiently small that it is readily packaged in pIX-virions resulting in virus preparations enriched for the helper dependent vector.

Figure 31:
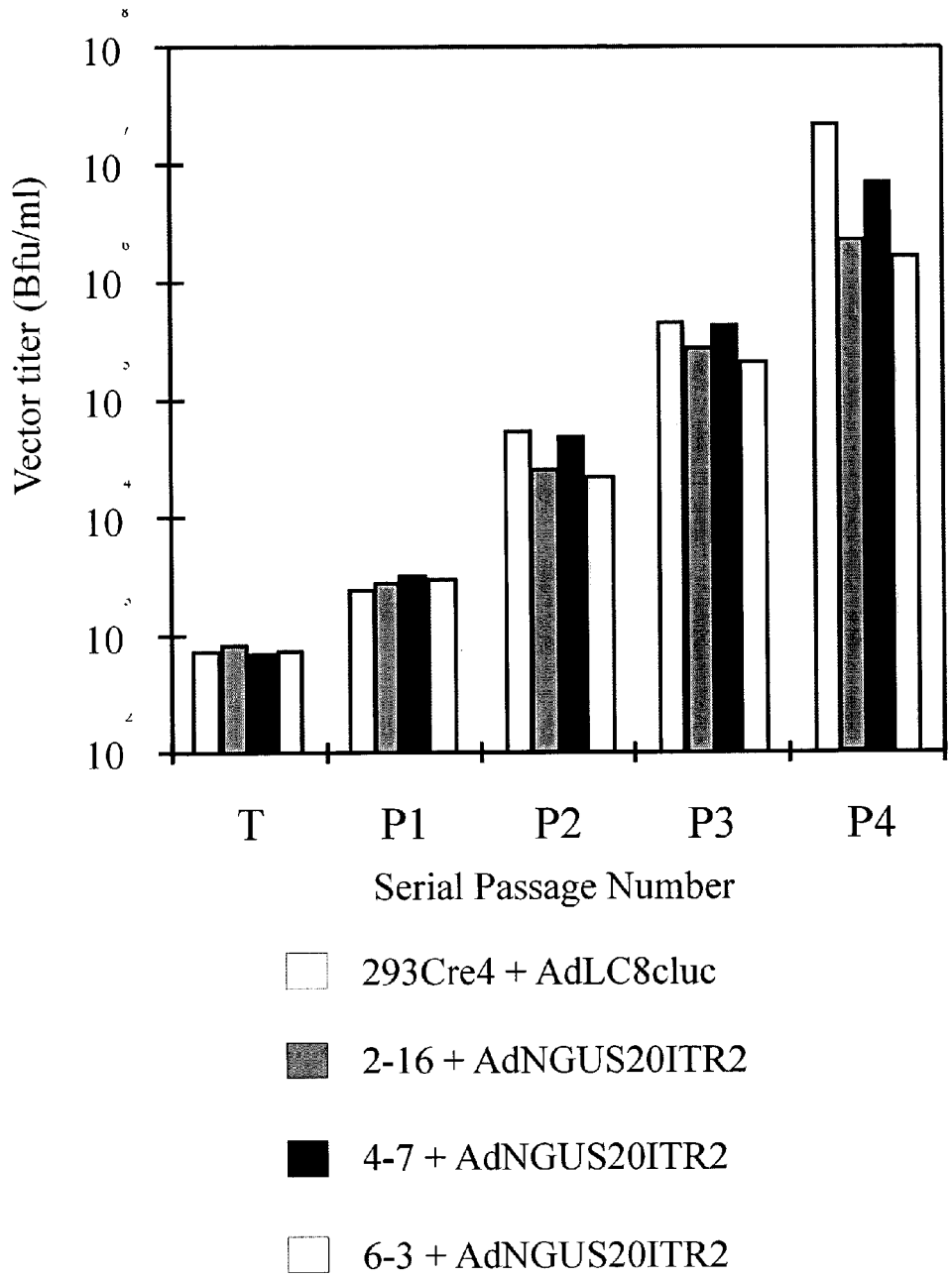

FIG. 31. Amplification kinetics of the helper dependent vector AdRP1050. Amplification of AdRP1050 using the indicated combination of cell line and helper virus was performed as described (Parks et al., 1996). Bfu, blue forming units; T, transfection; P1, passage 1; P2, passage 2; P3 passage 3; P4, passage 4.

Figure 32:
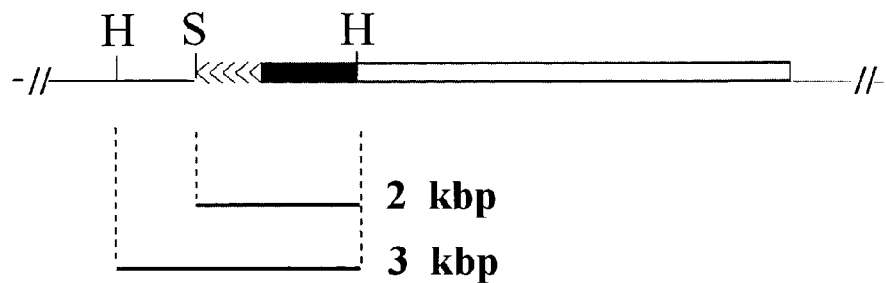
Figure 32:
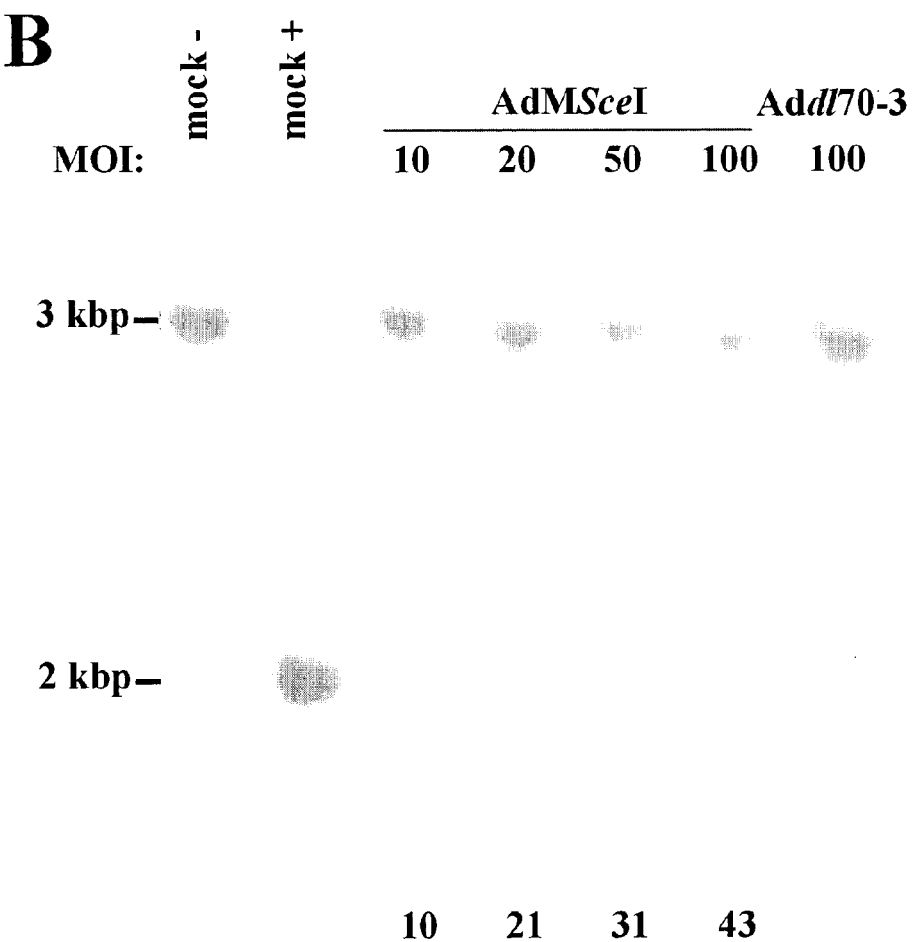

FIG. 32. AdMSceI-encoded I-SceI can efficiently cleave an intrachromosomal recognition site in vivo in replication-permissive cells. Genomic DNA, extracted from AdMSceI-infected 293.1 cells, Addl70-3-infected cells or mock-infected cells at 22 hours after infection were digested with HindIII and analysed by Southern hybridization with a neo probe. (A) Structure of integrated mMA2. Solid bars represent plasmid DNA with the region detected by the neo probe in black. Thin lines represent chromosomal sequences and arrows indicate the telomeric array in its orientation. The products of cleavage with HindIII (H) and I-SceI (S) (2 kb) or (H) alone (3 kb) are shown. (B) MOI and molecular weights (in kb) are indicated. The cleavage activity in percent cleaved molecules is shown below each lane. Mock– refers to DNA from mock-infected cells digested with (H), while mock+ refers to the same DNA digested with (H) and commercial I-SceI.

DETAILED DESCRIPTION OF THE PREFERRED EMBODIMENTS

Any publications referenced herein are hereby incorporated by reference in this application in order to more fully describe the state of the art to which the present invention pertains.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The terms used herein are not intended to be limiting of the invention. For example, the term "gene" includes cDNAs, RNA, or other polynucleotides that encode gene products. "Foreign gene" denotes a gene that has been obtained from an organism or cell type other than the organism or cell type in which it is expressed; it also refers to a gene from the same organism that has been translocated from its normal situs in the genome. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives are also within the scope of the present invention. "Expression" of a gene or nucleic acid encompasses not only cellular gene expression, but also the transcription and translation of nucleic acid(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. The term "gene product" refers primarily to proteins and polypeptides encoded by other nucleic acids (e.g., non-coding and regulatory RNAs such as tRNA, sRNPs). The term "regulation of expression" refers to events or molecules that increase or decrease the synthesis, degradation, availability or activity of a given gene product.

The present invention is also not limited to the use of the cell types and cell lines used herein. Cells from different tissues (breast epithelium, colon, lymphocytes, etc.) or different species (human, mouse, etc.) are also useful in the present invention.

It is important in this invention to detect the generation and expression of recombinant nucleic acids and their encoded gene products. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, *Genomics* 4: 560–569 (1989); Landren et al., *Proc. Natl. Acad. Sci.* 87: 8923–8927 (1990); Barany, F., *Proc. Natl. Acad. Sci.* 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permit the ligation reaction to be conducted with high stringency (Barany, F., *PCR Methods and Applications* 1: 5–16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

The detection oligonucleotide probes range in size between 10–1,000 bases. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formamide in the stringency washes.

The cloning and expression vectors described herein are introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by references, and in Ausubel et al., *Current Protocols in Molecular Biology*, John Wiley and Sons, Baltimore, Md. (1989), which is also hereby incorporated by reference. The methods include, for example, stable or transient transfection, lipofection, electroporation and infection with recombinant viral vectors.

The protein products of recombined and unrecombined coding sequences may be analyzed using immune techniques. For example, a protein, or a fragment thereof is injected into a host animal along with an adjuvant so as to generate an immune response. Immunoglobulins which bind the recombinant fragment are harvested as an antiserum, and are optionally further purified by affinity chromatography or other means. Additionally, spleen cells may be harvested from an immunized mouse host and fused to myeloma cells to produce a bank of antibody-secreting hybridoma cells. The bank of hybridomas is screened for clones that secrete immunoglobulins which bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic olignucleotides, etc.) as well as by a variety of different techniques.

The DNA sequences are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and optionally, sequences necessary for replication of a vector.

*E. Coli* is one prokaryotic host useful particularly for cloning DNA sequences of the present invention. Other microbial hosts suitable for use include bacilli, such as *Bacillus subtilus*, and other enterobacteriaceac, such as *Salmonella, Serratia*, and various *Pseudomonas* species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. *Saccharomyces* is a suitable host, with suitable vectors having expression control sequences, such a promoters, including 3-phosphoglycerate kinase or other glycolytic enzymes, and an origin of replication, termination sequences, etc. as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobin genes, SV40, Adenovirus, Bovine Papilloma Virus, Herpes Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is useful for other cellular hosts.

The method lends itself readily to the formulation of test kits for use in diagnosis. Such a kit comprises a carrier compartmentalized to receive in close confinement one or more containers wherein a first container contains reagents useful in the localization of the labeled probes, such as enzyme substrates. Still other containers contain restriction enzymes, buffers etc., together with instructions for use.

The recombinant Ad vectors described herein are significantly different from previously described constructs. They combine the use of vectors having deletions of all or most of the viral genes with helper viruses that are designed so that, when used in coinfections with vector viruses, said helper viruses are able to complement the growth of the vectors but are unable to package their viral DNA into infectious virions. Thus vector viruses can be prepared substantially free of helper virus.

For viral DNA replication and packaging of viral DNA into virion particles, only three regions of the viral DNA are known to be required in cis. These are the left inverted terminal repeat, or ITR, (bp 1 to approximately 103) the packaging signals (approximately 194 to 358 bp) (Hearing and Shenk, 1983, Cell 33: 695–703; Grable and Hearing 1992, J. Virol. 64: 2047–2056) and the right ITR. All other regions of the viral genome appear to be required only to produce viral products that act in trans to allow viral replication and production of infectious viruses. Thus if all essential viral proteins and RNA could be provided by a helper virus, a vector could be designed and constructed that could have most of the viral DNA deleted save for those sequences mentioned above that are required in cis for viral DNA replication and packaging.

It will be appreciated that the specific advancements provided by the present invention have significance in the limitation of the level helper adenovirus contamination of helper dependent adenovirus vector preparations. To this end, those skilled in the art will recognize that there exist endonucleases, such as the meganuclease I-SceI (Omega-nuclease, commercially available from BOEHRINGER MANNHEIM, catalog numbers 1497235 and 1362399), hereinafter referred to as SceI or I-SceI, which recognize and specifically cleave DNA sequences that are not represented in the Ad genome and which are sufficiently long that said sequences would not be predicted to exist in the human genome, or would appear infrequently in the human genome. Therefore said nuclease may be expressed constitutively in human cells without deleterious effects. Existence of a few sites in the human genome is non-lethal to cells expressing a nuclease such as SceI, because repair of double-strand breaks in mammalian cell DNA is very efficient. Therefore double strand breaks induced by SceI are "healed" and surviving cells that continue to express SceI endonuclease or like endonucleases may be isolated. Those skilled in the art will appreciate that SceI is merely an example not meant to be limiting. Other endonucleases exist which meet the criteria of having long and infrequently expressed recognition sites. Furthermore, new endonucleases continue to be discovered, and such endonucleases and their specific recognition sites could likewise be employed according to the present invention.

Figure 6:
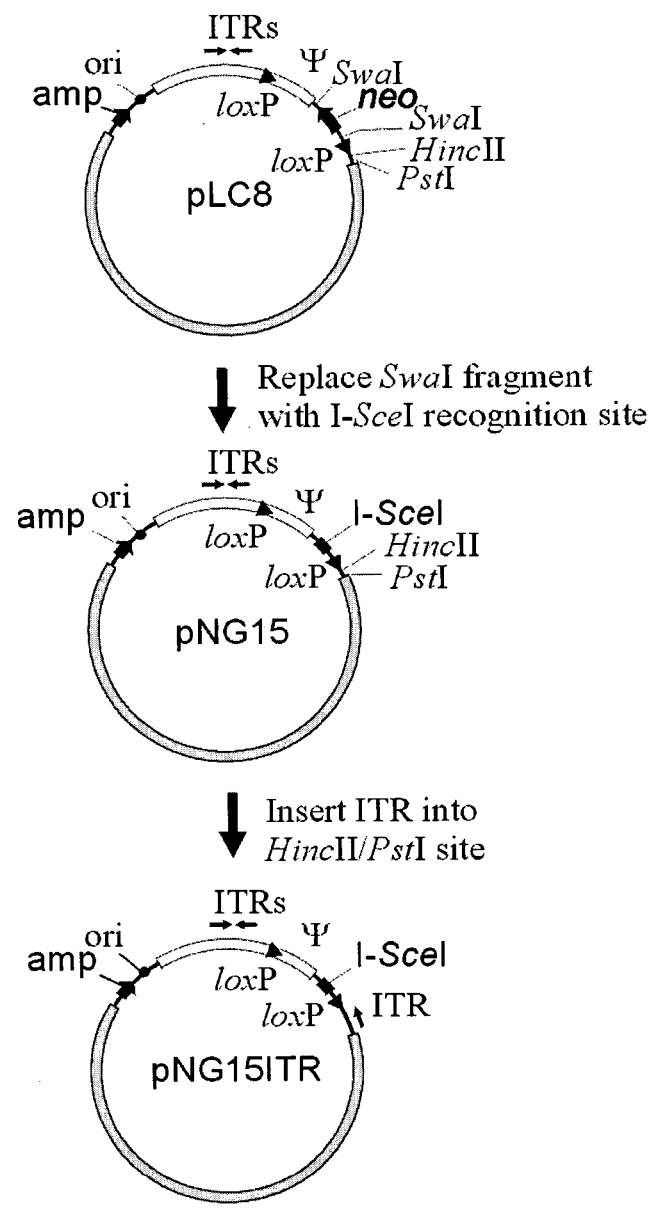
FIG. 6 illustrates the construction of a shuttle plasmid derived from pLC8 wherein an SceI recognition site is introduced adjacent to the floxed packaging signal followed by insertion of an ITR sequence to the right of the second lox site.

Because of the processes by which the adenovirus genome is replicated in mammalian cells, inverted terminal sequences, ITRs, can be inserted at internal sites within the Ad genome and such internal ITRs can be used in a "repair" process during Ad DNA replication such that the internal ITR becomes a true terminus or functional ITR used in initiation of Ad DNA replication, (see FIG. 6 of "Characterization of an adenovirus type 5 mutant carrying embedded inverted terminal repeats," Haj-Ahmad, Y. and Graham, F. L. Virology. 153, 22–34, 1986, hereby incorporated by reference for this purpose). The invention described herein combines the properties of rare cutting endonucleases, such as Sce I, and the above mentioned properties of the adenovirus to provide a novel system for production of HDV preparations substantially free of helper virus contamination.

Figure 1:
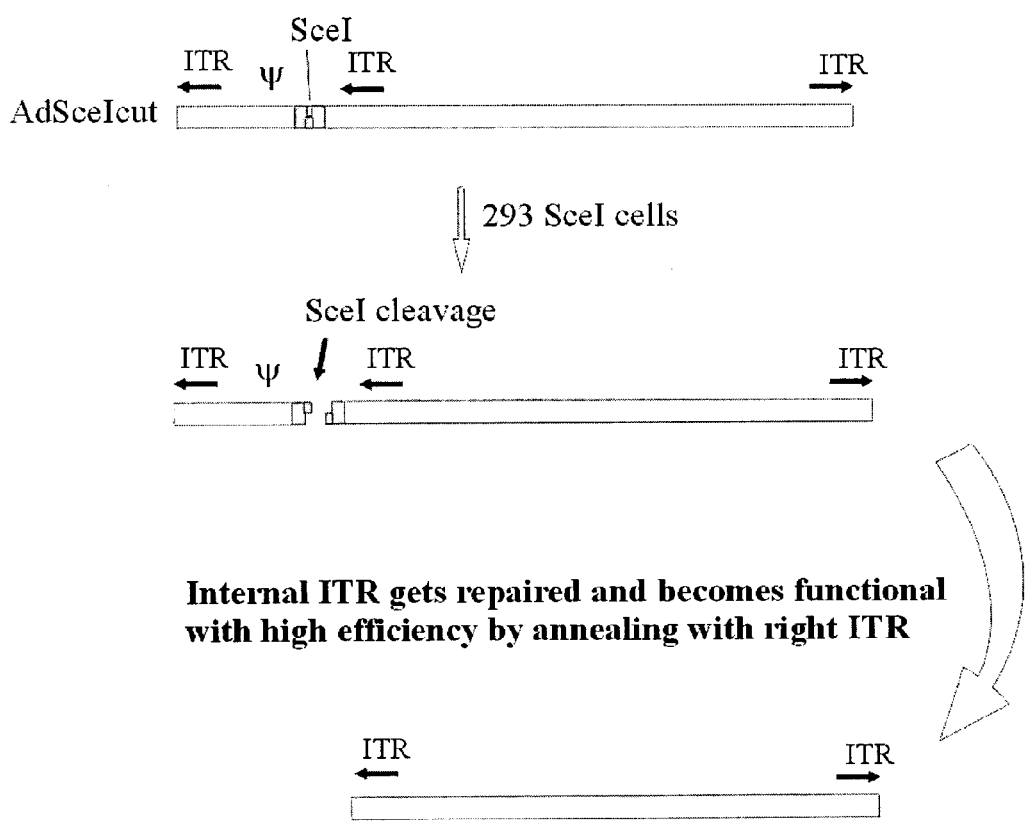
FIG. 1 is a diagrammatic representation of a helper adenovirus containing an endonuclease recognition cleavage site (SceI) near the left end of the viral genome and positioned to the right of the adenovirus packaging signal, ψ, illustrating the effects of endonuclease cleavage and ITR repair.
Figure 2:
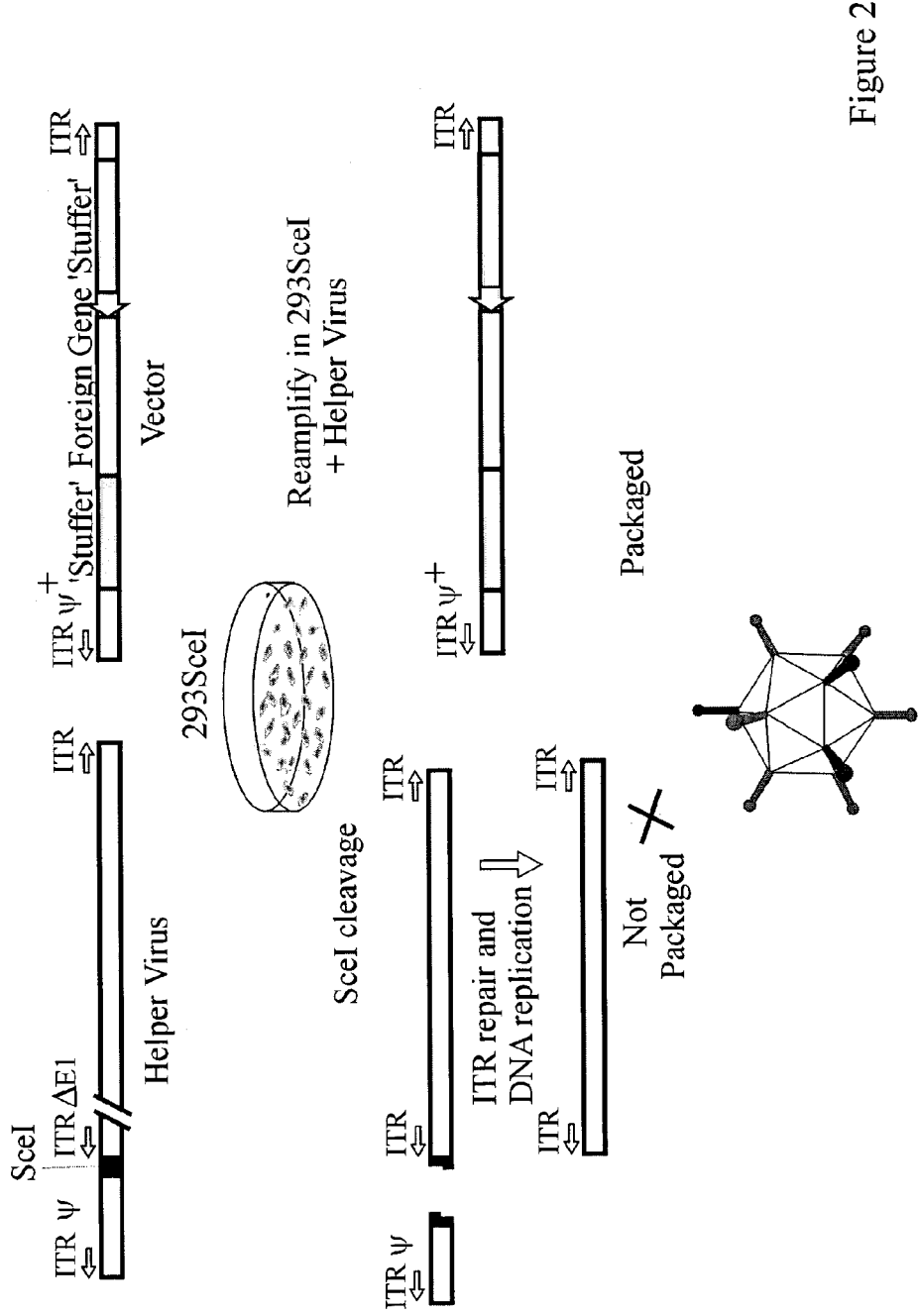
FIG. 2 is a diagrammatic representation showing a method for propagation of a helper dependent Ad vector (HDV) from which all or most of the viral genes have been deleted and substituted with foreign DNA.

The essential elements of this invention may be best understood with reference to FIGS. 1 and 2. A helper virus, referred to herein as AdSceIcut, is constructed such that an SceI or like endonuclease recognition site is disposed to the right of the helper virus packaging signal ($\psi$). An internal ITR sequence is inserted to the right of the endonuclease recognition site, as shown in FIG. 1. Preferably, the helper virus, AdSceIcut, includes a deletion of E1 sequences. This would facilitate helper virus propagation in 293 cells or any other host cells which support the replication of E1 deleted viruses. Optionally, the helper virus may retain E1 to the right of the SceI site and the internal ITR.

Infection of cells expressing SceI, such as 293SceI cells, results in cleavage by SceI endonuclease at the SceI site. The result would be inactivation of the DNA molecule with respect to DNA replication, since replication requires ITRs at each end of the molecule. However, by virtue of the insertion of an internal ITR to the right of the endonuclease recognition site, the helper virus is repaired by annealing of said internal ITR to an external ITR at the right end of the DNA, resulting in the formation of a functional ITR at the left end of the molecule. Thus a DNA molecule competent for viral DNA replication is efficiently generated. While the resulting molecule is capable of replicating, it lacks the packaging signal needed for production of virions. Therefore, as illustrated in FIG. 2, a helper adenovirus (e.g. AdSceIcut) containing an appropriate endonuclease recognition site, such as an SceI site serves as a useful helper virus for production of substantially helper-free helper dependent adenovirus vectors (HDVs).

Figure 3:
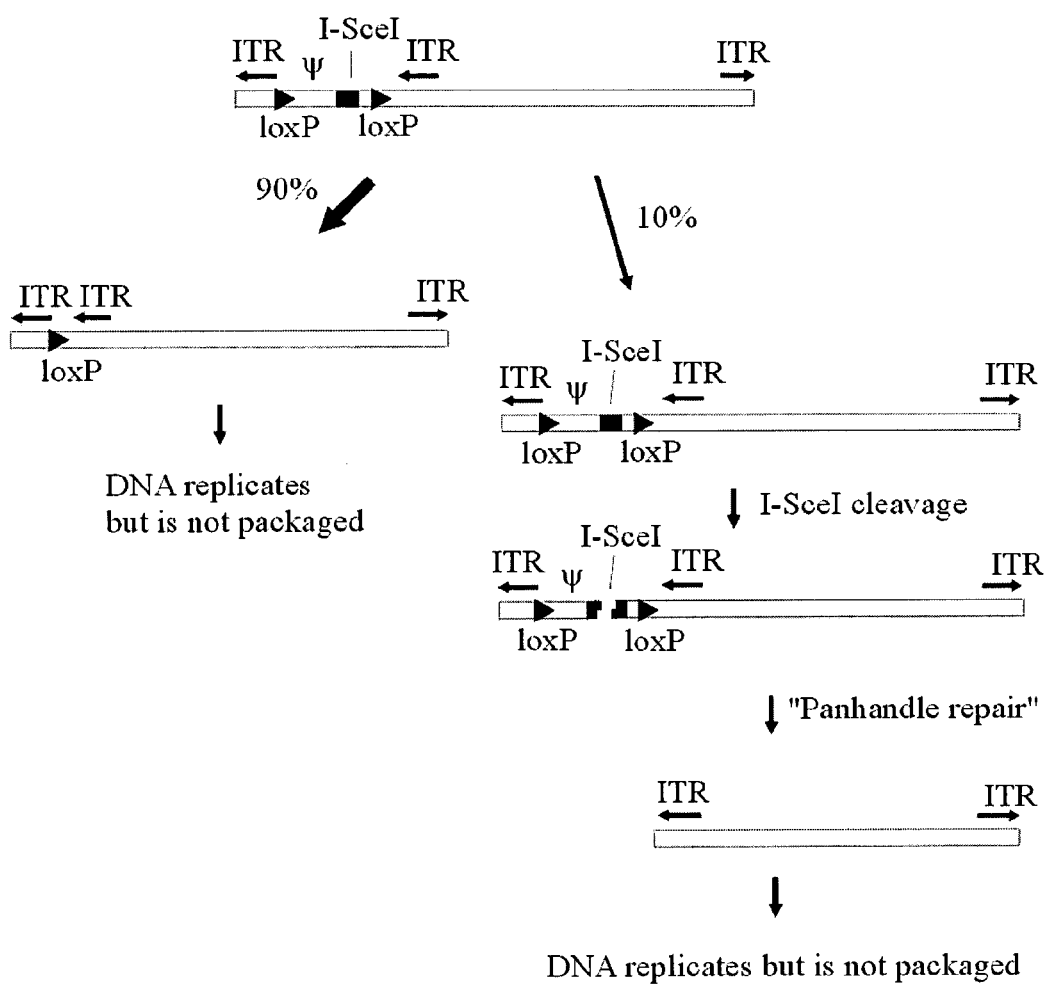
FIG. 3 illustrates a method for combining the Cre/lox system and the SceI system to produce a helper virus for improved production of helper free helper dependent vectors.

In a further embodiment of this invention, the endonuclease system described above is combined with the Cre/lox system disclosed according to U.S. Pat. No. 5,919,676, in order to further reduce the degree of helper virus contamination in HDV preparations. Cells expressing both Cre and an appropriate endonuclease, such as 293 cells that express both Cre and SceI, are preferably employed for this purpose. According to this embodiment of the invention, a helper virus is constructed wherein a lox site is positioned on either side of the packaging signal. An embedded ITR is placed to the right of the innermost lox site. An appropriate endonuclease recognition site is placed to the right of the packaging signal, either between the two lox sites, or to the right of the innermost lox site, but to the left of the embedded ITR. Alternatively, both the SceI site and adjacent internal ITR are placed between the packaging signal and the innermost loxP site. In this manner, if the Cre/lox system "leaks" and helper virus containing packaging signal would otherwise contaminate the HDV preparation, the presence of the endonuclease recognition site provides a "fail-safe" mechanism by which residual helper virus containing packaging signal is prevented from forming virions. An example of a suitable helper virus for use in such a combination is illustrated in FIG. 3. In this embodiment of the invention, an SceI site is located between the loxP sites which in turn flank the packaging signal. Helper virus genomes in which the packaging signal has not been excised through the action of Cre are susceptible to SceI cleavage as shown in the lower right of the illustration. Therefore the low number of helper virus genomes that escape Cre mediated excision of ψ is further reduced in number by SceI cleavage.

Because of the surprisingly high efficiency with which we have found DNA fragments generated by SceI cleavage can be joined in various ways, it will be appreciated by those skilled in the art, based on the present disclosure, that a number of possible uses for SceI cleavage become possible. First, it will be seen that since the viral DNA species formed by joining of fragments A and C in FIG. 26 is an abundant species, and since this molecule lacks a packaging signal, a helper virus containing a packaging signal flanked by SceI sites is a preferred embodiment of the invention. The helper virus may optionally carry an internal ITR so that in the absence of A/C joining, panhandle formation and repair illustrated on the right portion of FIG. 26, can generate a DNA molecule that is able to replicate. Second, it will be seen that any DNA fragment in a viral genome can be flanked by SceI sites and the process of SceI cleavage followed by double strand break repair resulting in rejoining of viral DNA fragments from the left and the right of the fragment that was flanked by SceI sites effectively results in excision of the flanked fragment. Consequently it is possible to create a molecular switch for regulation of gene expression that is operationally virtually identical to that based on Cre-lox recombination described by Anton and Graham (Anton, M. and Graham, F. L. Site-specific recombination mediated by an adenovirus vector expressing the Cre recombinase protein: a molecular switch for control of gene expression. J. Virol. 69:4600–4606, 1995.) and in U.S. application Ser. No. 08/486,549 Filed Jun. 7, 1995 (now U.S. Pat. No. 6,120,764), but which is dependent on SceI mediated rather than Cre-lox mediated excision. An example not meant to be limiting is illustrated in FIG. 28. In this example I-SceI mediated cleavage followed by rejoining of the left-most and right-most viral DNA fragments results in a viral genome containing a functional expression cassette for production of β-galactosidase. Such a cassette need not be located in the E1 region but could equally be engineered in E3 or elsewhere in the viral genome. Other viruses such as herpes viruses, papilloma viruses, pox viruses and the like could be similarly engineered.

Furthermore, an adenovirus or other virus or a plasmid DNA expressing I-SceI could be delivered to cells or to an animal whose genome contains SceI susceptible sites and expression of I-SceI will result in cleavage of said sites. Repair by joining of DNA ends can result in a chromosome with the structure illustrated in FIG. 29 wherein the SceI cleavage followed by double strand break repair effectively results in excision of a DNA fragment and, in the example shown, switches expression of a gene, such as β-galactosidase or any other gene, on or off. Because the double strand break repair mechanism is imperfect, the SceI cleavage site would only rarely be regenerated and consequently the reaction would be essentially irreversible.

It will be appreciated by those skilled in the art, based on the present disclosure, that wherever we use I-SceI endonuclease or SceI sites we could use any other site specific endonuclease that could be expressed in mammalian cells and that can be used to cut specific sequences in a DNA. Thus, the examples with I-SceI are not meant to be limiting. Similarly where we use Cre-lox we could equally use FLP-FRT or like site specific recombinase systems.

Having generally described this invention, the following examples are included herein to provide additional written description and enablement for specific embodiments of the disclosed invention. The invention, however, should not be interpreted as being limited to the specifics of these examples. Rather, the scope of this invention is to be determined from the complete disclosure and the claims appended hereto.

EXAMPLES

Example 1

Endonuclease Cleavage of Helper Virus

FIG. 1 shows an adenovirus containing an SceI site near the left end of the viral genome and positioned to the right of the packaging signal, ψ, illustrating the effects of SceI cleavage and ITR repair. Infection of 293SceI cells results in a double strand break in the DNA as a result of SceI endonuclease activity. Because the adjacent, embedded ITR is repaired by panhandle formation (annealing with the right ITR) a functional DNA molecule is formed that is capable of replicating but which lacks the packaging signal and consequently cannot be packaged into virions.

Example 2

Propagation of Helper Dependent Adenovirus Vector and Elimination of Helper Virus Contamination Via Endonuclease Cleavage FIG. 2 illustrates propagation of a helper dependent Ad vector from which all or most of the viral genes have been deleted and substituted with foreign DNA and "stuffer" DNA. The stuffer DNA is used to maintain an optimal size of the vector's genome to maximize efficiency of packaging. Coinfection of 293SceI cells with the vector and helper results in SceI mediated cleavage of the helper virus DNA as shown. The internal ITR positioned to the right of the SceI site is repaired, resulting in a DNA molecule that is replicated and amplified. However, due to the lack of a packaging signal, the helper viral DNA cannot be packaged into virions. The replicating but non-packageable helper virus DNA provides all of the trans-acting functions necessary for replication of the vector (which lacks all or most viral genes but retains those viral DNA sequences necessary in cis for DNA replication and packaging) and for formation of virion particles. Subsequent rounds of amplification of the vector in 293SceI cells coinfected with AdSceI helper virus result in production of large amounts of helper free helper dependent vector.

Example 3

Combined Cre/Lox Endonuclease System for Production of Helper Dependent Adenovirus Vectors FIG. 3 illustrates the use of a helper virus which includes the Cre/lox system in combination with an endonuclease, an endonuclease target sequence and an embedded ITR for production of helper free helper dependent vectors. To construct this virus an SceI or like endonuclease recognition site is placed between lox sites flanking the packaging signal and an internal ITR is inserted to the right of the second lox site. In a preferred embodiment, the SceI site is placed to the right of the packaging signal, but to the left of the second loxP site. Alternatively, the endonuclease recognition site is placed to the right of the internal lox site but to the left of the internal ITR, or both the SceI site and the embedded ITR are positioned between the packaging signal and the rightmost loxP site. Infection of 293Cre cells which results in efficient but incomplete excision of the packaging signal provides a small but significant number of helper viruses that "escape" Cre mediated excision. Use of 293 cells expressing both Cre and SceI minimizes the number of residual helper viruses that can be packaged through the action of the SceI endonuclease.

Example 4

Figure 4:
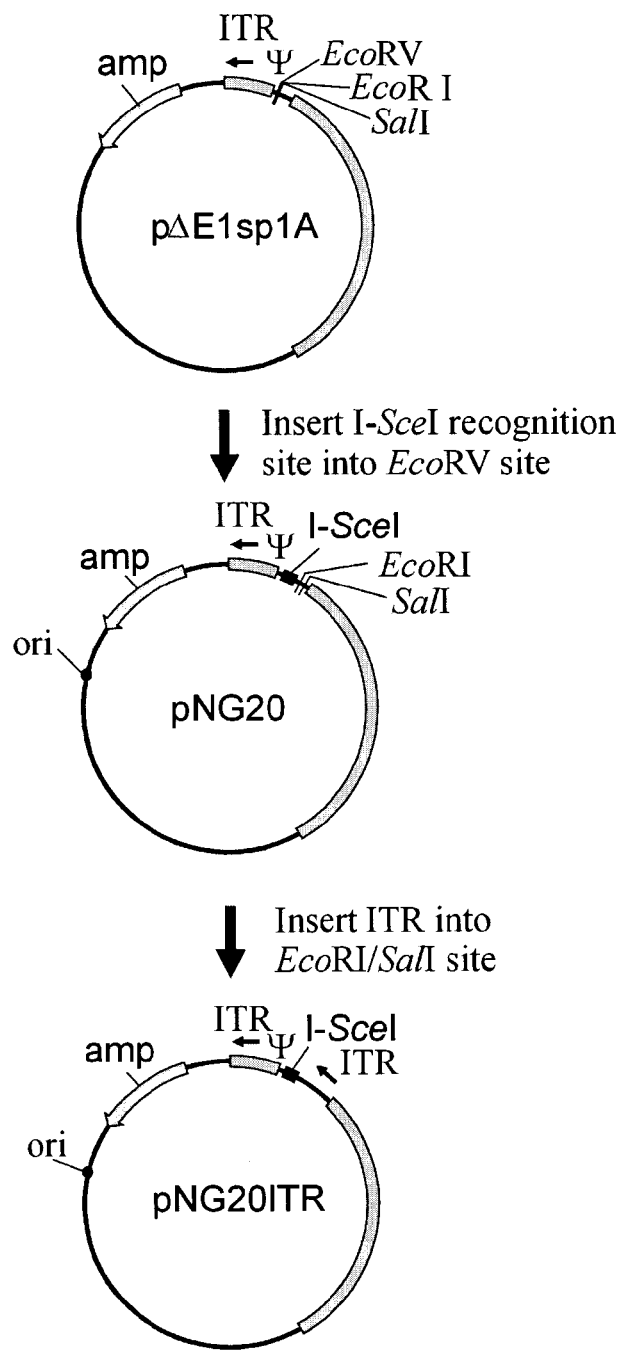
FIG. 4 illustrates the construction of a shuttle plasmid derived from pΔE1SP1A wherein an SceI recognition site is introduced adjacent to the packaging signal followed by insertion of an ITR sequence.

Construction of Shuttle Plasmids Containing Endonuclease Recognition Sites and Embedded ITR Sites FIG. 4 illustrates the construction of a shuttle plasmid derived from pΔE1SP1A wherein an SceI recognition site is introduced adjacent to the packaging signal followed by insertion of an ITR sequence. PΔE1SP1A (commercially available from Microbix Biosystems) is a shuttle plasmid that contains Ad sequences from the left end of the genome (approximately nts 1 to 354 including the left ITR and the packaging signal) a polycloning site including EcoRV, EcoRI and SalI sites, and additional Ad sequences from nts approximately 3540 to 5790 and is useful for rescue of genes or mutations into the left end of the Ad genome. A synthetic oligonucleotide containing an SceI recognition site (FIG. 4a) was inserted into the EcoRV site to generate pNG20, as illustrated. Subsequently pNG20ITR was constructed by inserting a PCR amplified ITR (FIG. 5) into the EcoRI/SalI site.

Example 5

Figure 9:
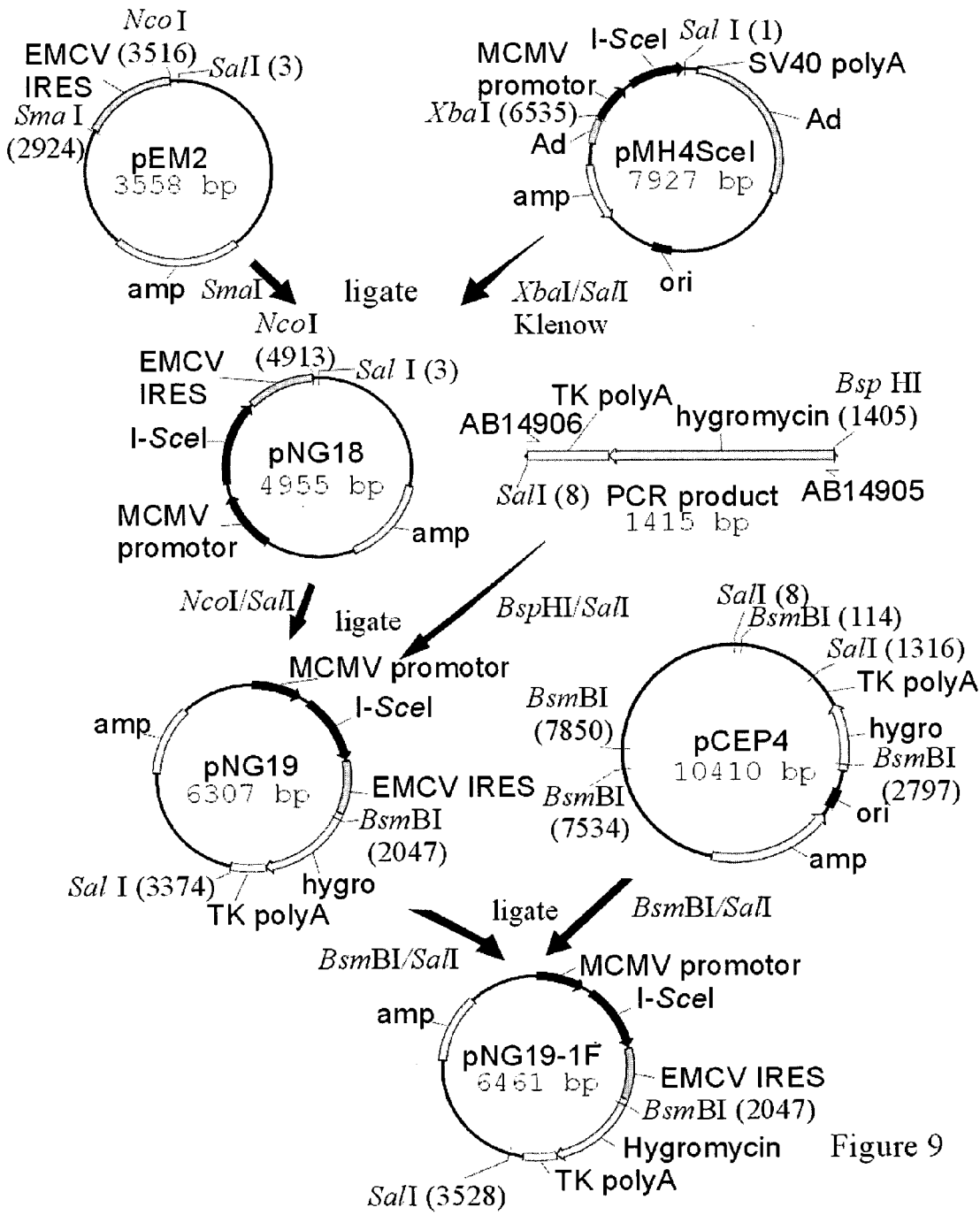
FIG. 9 illustrates construction of a plasmid expressing SceI and hygromycin resistance for transformation of cells.

Oligonucleotides Useful in Constructing Helper Viruses According to this Invention FIG. 4a illustrates the sequence of oligonucleotides used to generate the SceI recognition site in pNG15 (FIG. 6) and pNG20 (FIG. 4), the sequence of oligonucleotides used for PCR amplification of adenovirus ITRs (FIG. 5) and the sequence of oligonucleotides used for PCR amplification of a hygromycin resistance gene (FIG. 9). The oligonucleotides AB14265, SEQ ID NO. 1, and AB14270, SEQ ID NO. 2, were hybridized to create an SceI recognition site indicated in bold. An AflII site (5'CTTAAG3'), indicated in italics, was included to facilitate screening for recombinant plasmids bearing the SceI recognition site. Oligonucleotides AB15136, SEQ ID NO.3, and AB 15137, SEQ ID NO. 4, were used to produce an ITR (FIG. 5) for cloning into pNG20 (FIG. 4). Oligonucleotides AB15051, SEQ ID NO. 5, and AB 15052, SEQ ID NO. 6, were used to produce an ITR (FIG. 5) for cloning into pNG15 (FIG. 6). Oligonucleotides AB14905, SEQ ID NO. 7, and AB 14906, SEQ ID NO. 8, were used for PCR amplification of a hygromycin resistance gene (FIG. 9).

Example 6

PCR Production of ITR for Embedded Insertion into a Helper Adenovirus

Figure 5:
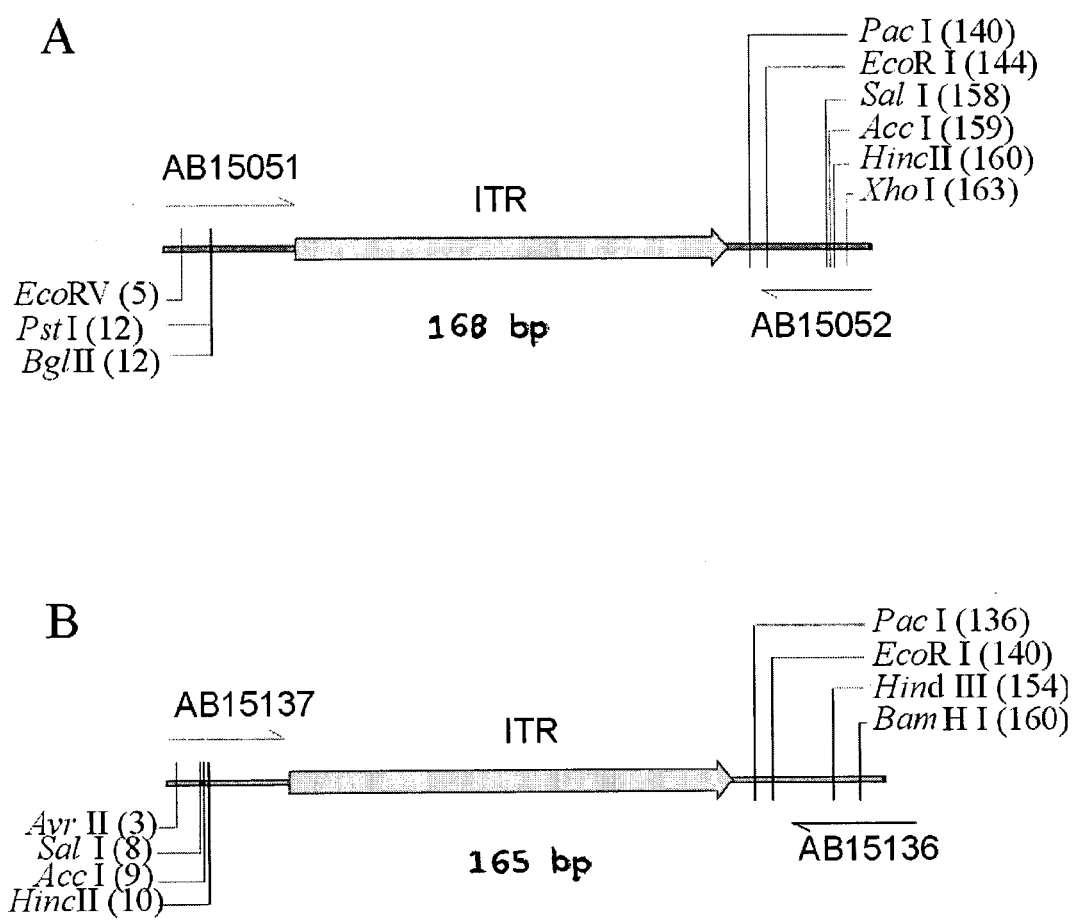
FIG. 5 illustrates the use of PCR to amplify adenovirus ITRs from the plasmid pAdHV1HelperpIX⁻.

FIG. 5 illustrates the use of PCR to amplify adenovirus ITRs from the plasmid pAdHV1HelperpIX⁻

(A) PCR was used to amplify a complete wild type ITR from the plasmid pAdHV1HelperpIX⁻ with primers AB15136 (5'-CGGATCCAAGCTTGCGAGATCGAATTC-3'), SEQ ID NO.3, and AB15137 (5'-GCCTAGGTCGA-CACTCCGCCCTAAAAC-3'), SEQ ID NO.4. The plasmid pAdHV1HelperpIX⁻ is an Ad genomic plasmid that is deleted of E1, pIX and E3 with ITRs that can be liberated by PacI digestion (constructed by Andy Bett, Merck Inc.). One skilled in the art will appreciate that any plasmid carrying a complete ITR could equally serve as a source of an ITR for PCR amplification or adenovirus DNA could equally be used. The 165 bp PCR product was digested with EcoRI and SalI and cloned into the EcoRI/SalI sites of the plasmid pNG20 to generate pNG20ITR (FIG. 4).

(B) Primers AB15051 (5'-GGATATCTGCAGATC-TACTCCGCCCTAAAAC-3'), SEQ ID NO. 5, and AB15052 (5'-CCTCGAGTCGACGCGAGATCGAATTC-3'), SEQ ID NO.6, were used to produce a 168 bp PCR product that was subsequently digested with PstI and HincII and cloned into the PstI/HincII sites of the plasmid pNG15 to generate pNG15ITR (FIG. 6).

Example 7

Construction of Helper Virus Containing a Floxed Packaging Signal, an Endonuclease Recognition Site and an Embedded ITR FIG. 6 illustrates the construction of a shuttle plasmid derived from pLC8 wherein an SceI recognition site is introduced adjacent to the floxed packaging signal followed by insertion of an ITR sequence to the right of the second lox site. (pLC8 is described in Parks, R. J., Chen, L., Anton, M., Sankar, U., Rudnicki, M. A. and Graham, F. L. A new helper-dependent adenovirus vector system: removal of helper virus by Cre-mediated excision of the viral packaging signal. Proc. Natl. Acad. Sci. U.S. 93:13565–13570, 1996, hereby incorporated by reference for this purpose). The SwaI fragment of pLC8 bearing the neo gene was replaced with an oligonucleotide containing the SceI recognition site by ligation of oligo AB14265/AB14270 (FIG. 4a), SEQ ID Nos. 1 and 2, into SwaI digested pLC8 to generate pNG15. The plasmid pNG15ITR was then obtained by inserting a PCR amplified ITR (FIG. 5) into the HincII/PstI site of pNG15.

Example 8

Figure 7:
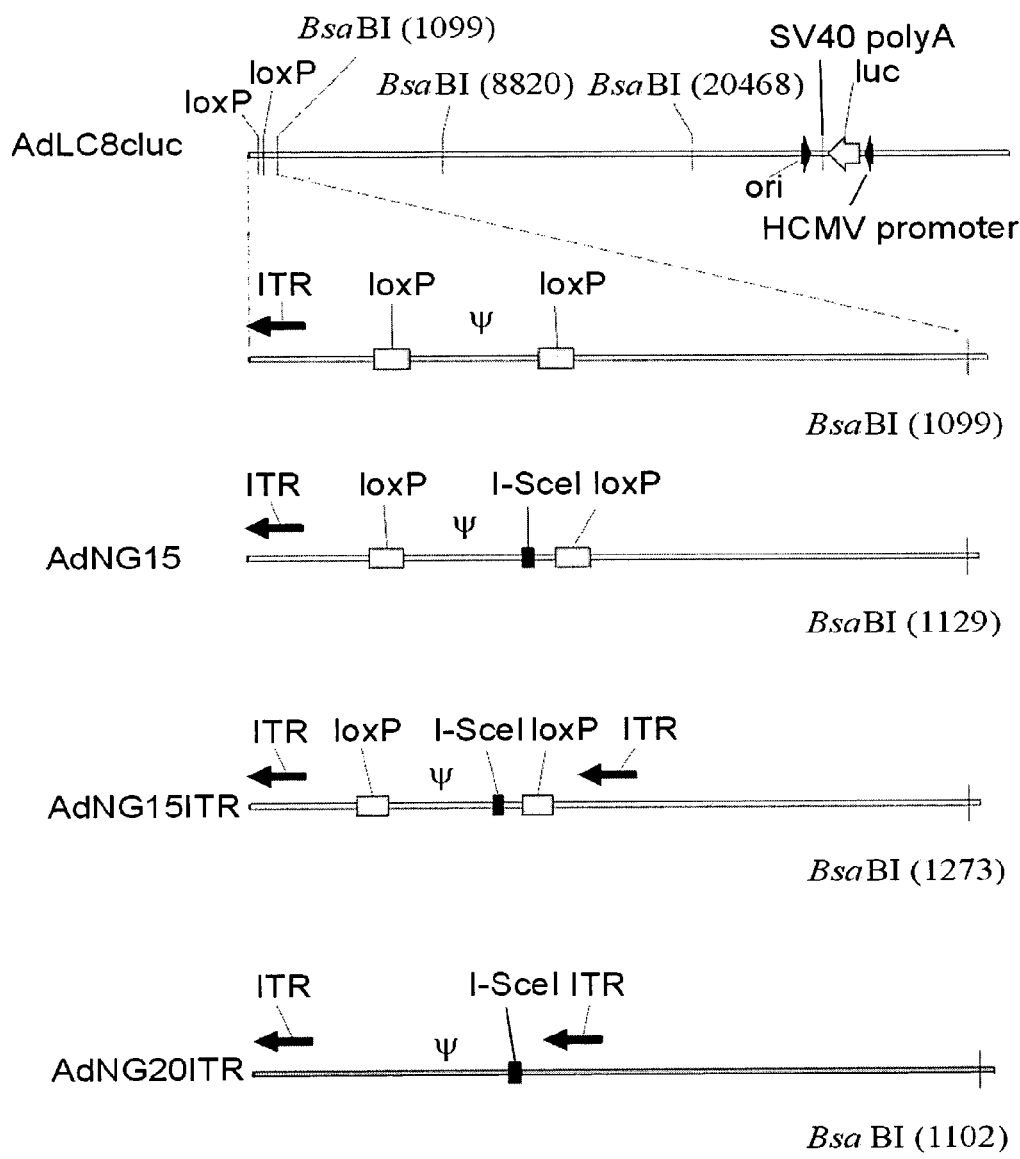
FIG. 7 illustrates the structure of new helper viruses derived by cotransfection of 293 cells with pBHG101uc and the shuttle plasmids of FIGS. 4 and 6.

Construction of Helper Virus using Shuttle Plasmids Containing Endonuclease Recognition Sites and Embedded ITR Sites FIG. 7 illustrates the structure of new helper viruses derived by cotransfection of 293 cells with pBHG10luc and the shuttle plasmids of FIGS. 4 and 6. The helper virus AdLC8cluc was generated by cotransfection of 293 cells with the shuttle plasmid pLC8c and the Ad genomic plasmid pBHG10luc and has been described in detail elsewhere (Parks et al., 1996). The packaging signal (ψ) in AdLC8cluc is flanked by loxP sites. The helper virus AdNG15 was generated by cotransfection of 293 cells with the shuttle plasmid pNG15 and pBHG10luc. The structure of AdNG15 is identical to AdLC8cluc except for the presence of an SceI recognition site immediately to the right of the packaging signal. The helper virus AdNG15ITR was generated by cotransfection of 293 cells with the shuttle plasmid pNG15ITR and pBHG10luc. The structure of AdNG15ITR is identical to AdNG15 except for the presence of an ITR immediately 3' of the rightward loxP site. The helper virus AdNG20ITR was generated by cotransfection of 293 cells with pNG20ITR and pBHG10luc. An I-SceI recognition site, followed by an ITR, reside immediately downstream of the packaging signal in AdNG20ITR.

Example 9

Demonstration that Endonuclease Recognition System is Operative

Figure 8:
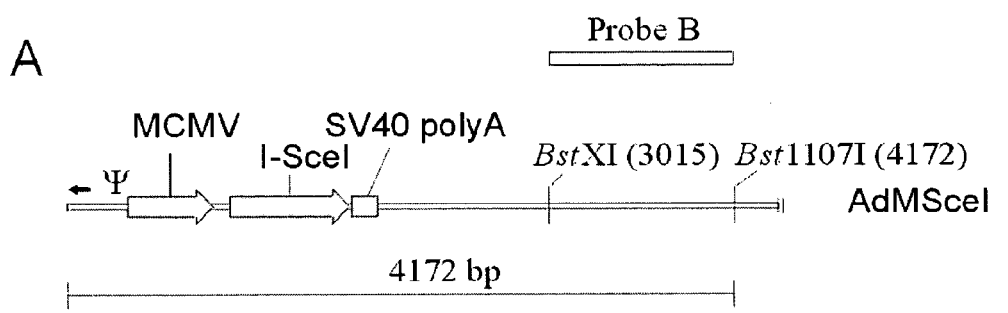
FIG. 8 shows a Southern blot hybridization analysis of cleavage products generated by coinfection of A549 cells with a virus containing an SceI site near the left end of the genome (AdNG15) and a second virus, AdMSceI, expressing the SceI endonuclease.
Figure 8:
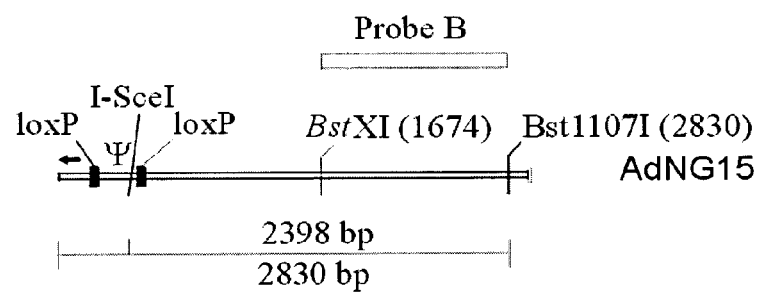
Figure 8:
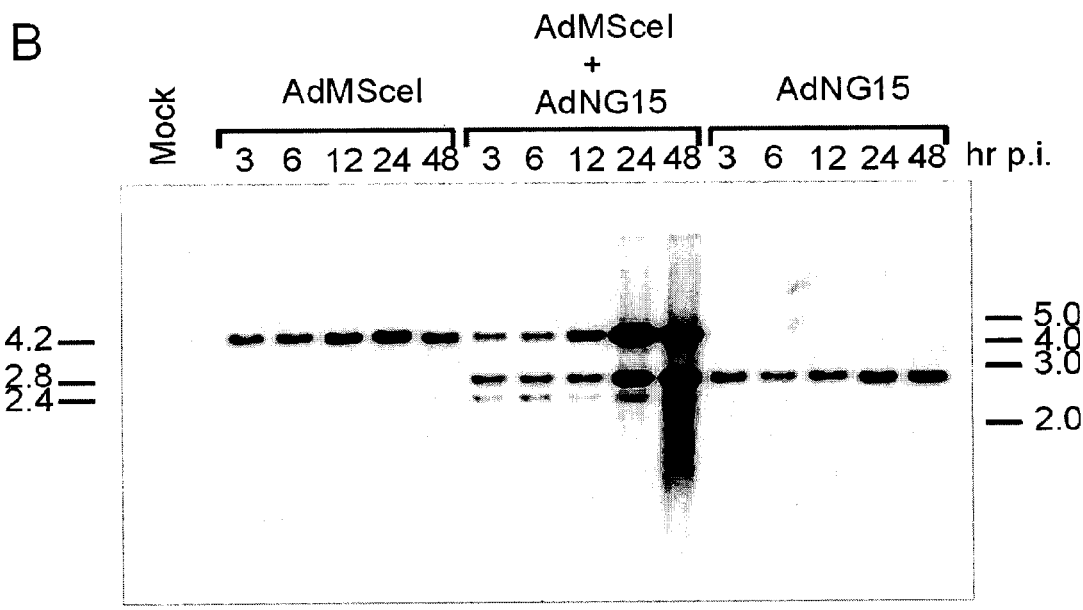

FIG. 8 Provides an Analysis of I-SceI cleavage of AdNG15 in A549 cells:

(A) AdMSceI is an Ad vector that expresses the endonuclease SceI. AdNG15 is a helper virus bearing an SceI recognition site adjacent to the packaging signal (ψ), both of which are flanked by loxP sites (FIG. 7). The left end of the AdMSceI genome is included in a 4172 bp Bst1107I fragment. The left end of the AdNG15 genome is included in a 2830 bp Bst1107I fragment which is easily separable from the corresponding left end fragment of AdMSceI by agarose gel electrophoresis.

(B) To determine whether the SceI recognition site in the AdNG15 genome was susceptible to cleavage by SceI in vivo, semiconfluent monolayers of A549 cells were infected with AdMSceI at an moi=10. Twenty four hours later (designated as 0 hr in FIG. 8), the monolayers were infected with AdNG15 at an moi=10. A549 cells were also infected with either AdMSceI or AdNG15 alone to serve as controls. At the indicated times post infection, viral DNA was extracted from the infected cells, digested with Bst1107I and analyzed by Southern blotting with probe fragment B (a 1157 bp BstXI/Bst1107I fragment from pXCJL1 (Microbix Biosystems)) to determine whether AdNG15 had been cleaved by SceI. Cleavage of AdNG15 by SceI, is expected to convert the 2.8 kb Bst1107I to a 2.4 kb I-SceI/Bst1107I fragment. The expected 2.4 kb fragment is clearly visible even at the earliest time after AdNG15 infection of cells previously infected with AdMSceI, but is not present in DNA from singly infected cells. Thus Sce I expressed by the virus AdMSceI is clearly capable of cleaving the Sce I site in AdNG15.

Example 10

Figure 9A:
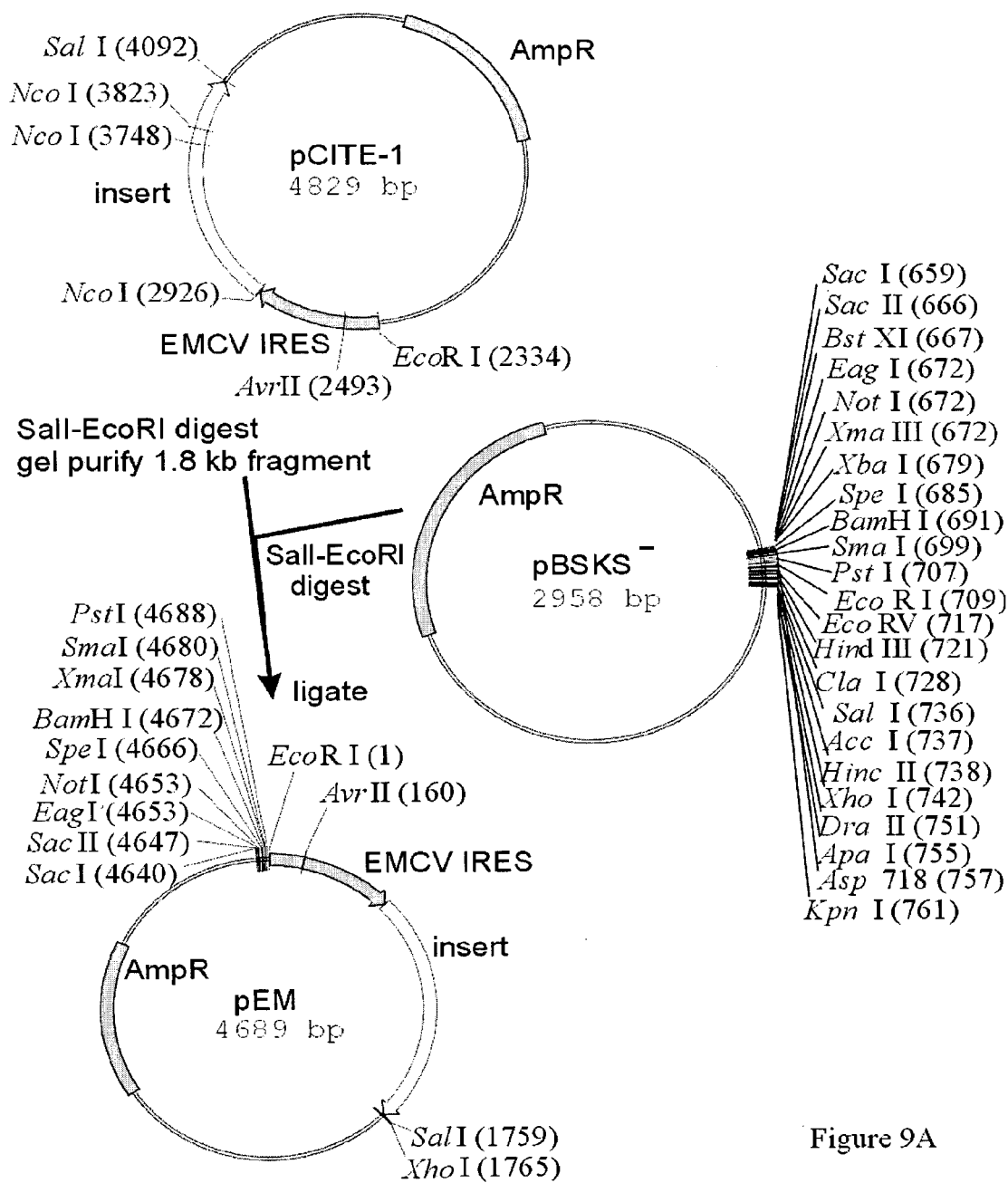
FIG. 9a and 9b illustrate construction of a plasmid containing an EMCV IRES sequence for use in construction of the plasmid of FIG. 9.
Figure 9B:
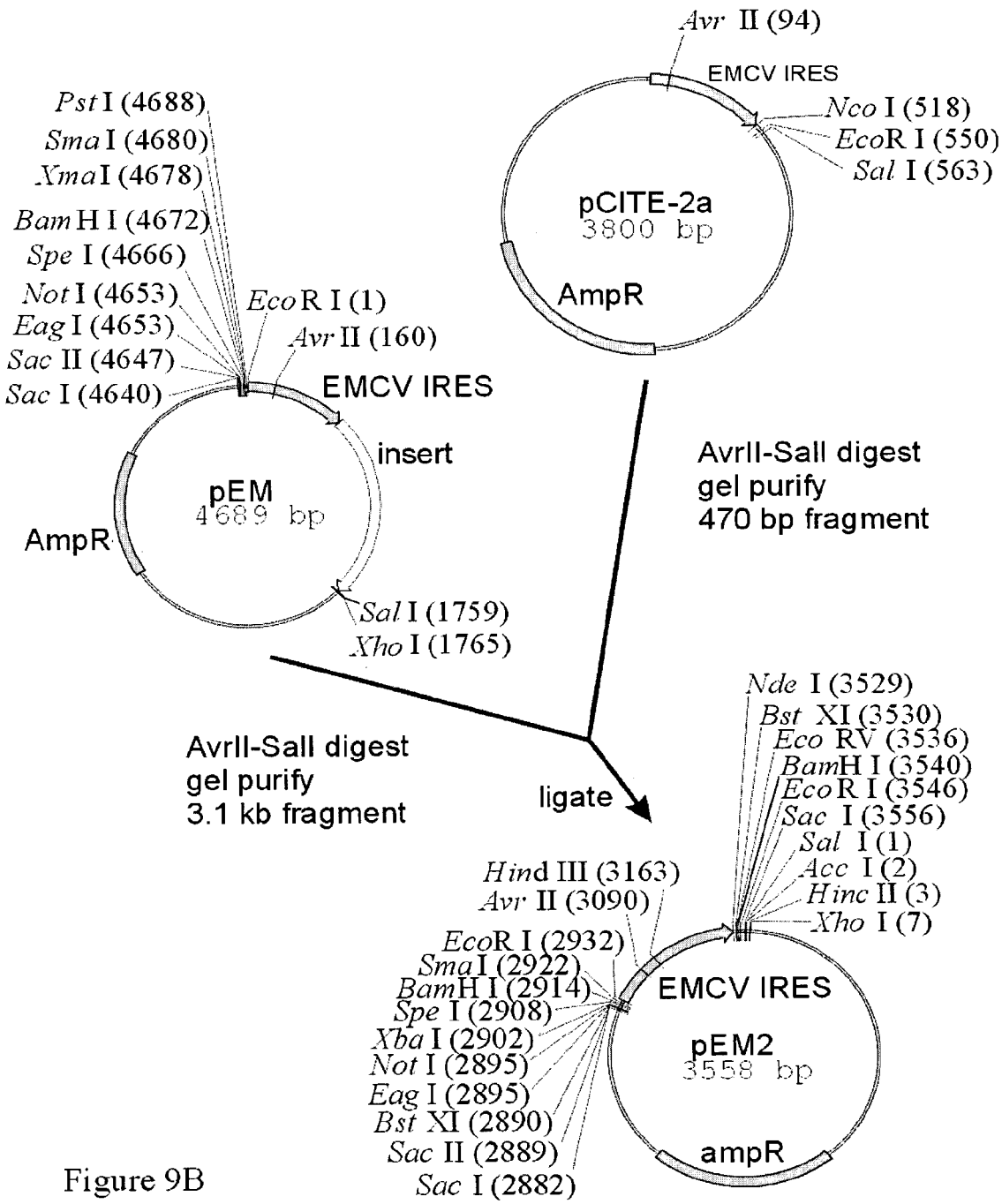

Construction of a Plasmid Expressing SceI Endonuclease and Hygromycin Resistance for Trasnformation of Cells As illustrated in FIG. 9, the plasmid pEM2 was constructed by cloning an EcoRI/SalI fragment containing the EMCV IRES into the EcoRI/SalI sites of pBluescript (Stratagene; see FIGS. 9a and 9b). The plasmid pMH4SceI was constructed by cloning the 853 bp EcoRI/SalI fragment containing the I-SceI gene from a plasmid containing the Sce I gene, pCMV-1-SceI (Rouet P, Smih F, Jasin M Expression of a site-specific endonuclease stimulates homologous recombination in mammalian cells. Proc Natl Acad Sci USA Jun. 21, 1994;91(13):6064–6068), into the EcoRI/SalI sites of pMH4 (available from Microbix Biosystems).) The plasmid pNG18 was constructed by cloning the Klenow treated 1393 bp XbaI/SalI fragment from pMH4SceI into the SmaI site of pEM2. The hygromycin coding sequence and TK polyA was amplified by PCR using the primers AB14905 (5'-GGGGGGTCATGAAAAAGC-CTGAACTC-3'), SEQ ID NO. 7, and AB14906 (5'-GGGGGGGTCGACCAGACCCCACGCAACG-3'), SEQ ID NO. 8, to obtain a 1415 bp product from pCEP4 (Invitrogen). The PCR product was cloned into the NcoI/SalI sites of pNG18 following digestion with BspHI/SalI to generate pNG19. The plasmid pNG19-1F was constructed by replacing the 1327 bp BsmBI/SalI fragment from pNG19 with the 1481 bp BsmBI/SalI fragment from pCEP4.

FIGS. 9a and 9b. Construction of an EMCV IRES cloning shuttle plasmid. PEM2 (used in the cloning illustrated in FIG. 9) was constructed from the Blue script plasmid pBSKS- (Statagene) and the EMCV IRES (Encephalomyocarditis Virus Internal Ribosome Entry Site) containing plasmids pCITE-1 and pCITE-2a (Novagen, U.S. Pat. No. 4,937,190) as shown.

Example 11

Figure 10:
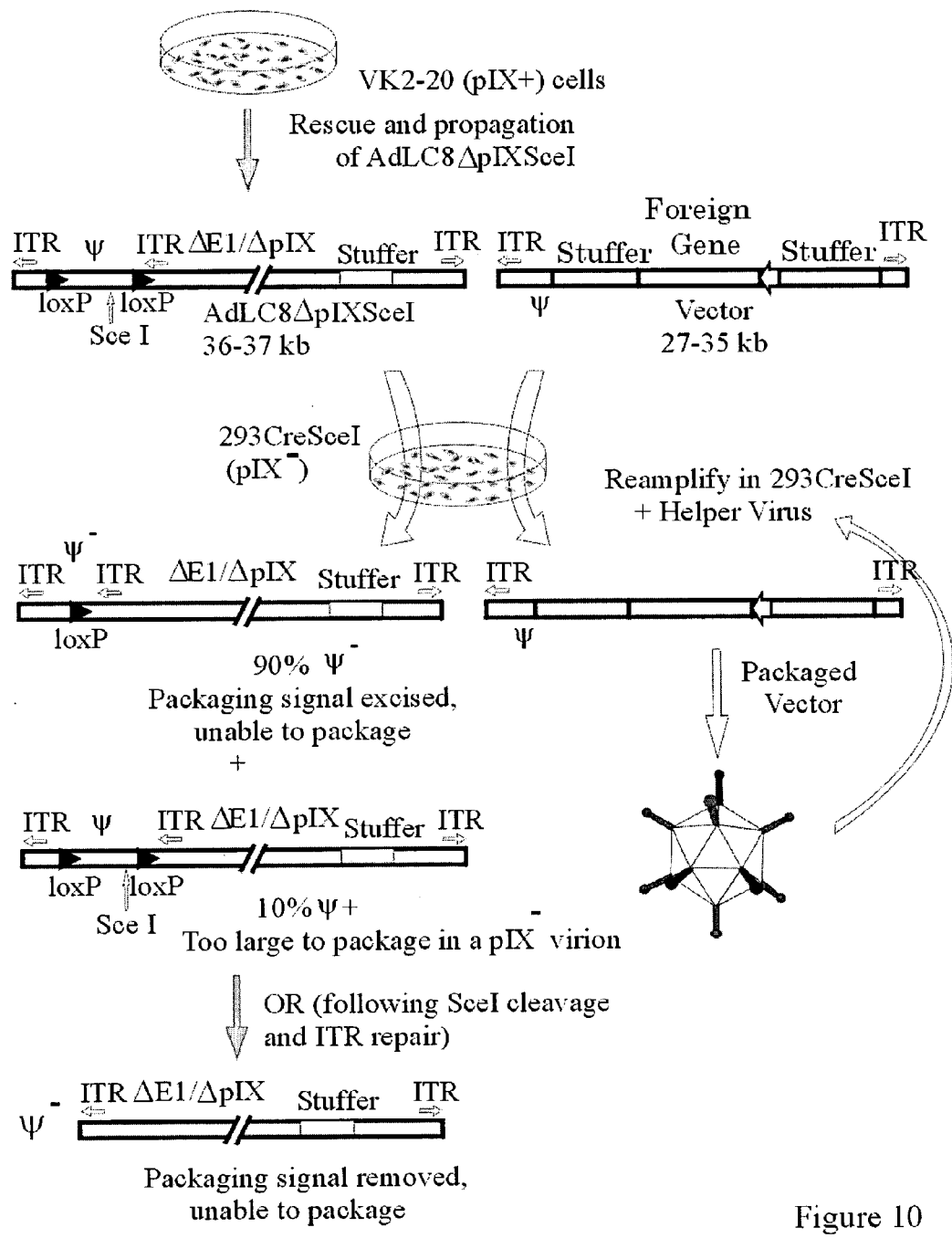
FIG. 10 illustrates a method for combining the Cre/loxP system of copending patent application Ser. No. 08/473,168 (hereby incorporated by reference, entitled "Adenoviral Vector System Comprising Cre-LoxP Recombination"), published as WO96/40955, the pIX system of copending patent application Ser. No. 08/719,217 (now U.S. Pat. No. 6,080,569), (hereby incorporated by reference, entitled "Improved Adenovirus Vectors Generated from Helper Viruses and Helper Dependent Vectors"), published as WO98/13510, and the endonuclease system of the present invention, for production of a helper dependent vector substantially free of helper virus.

Preparation of a Helper Dependent Adenovirus Vector Substantially Free of Helper Virus Contamination Due to Concurrent Limitation of Helper Virus Packaging by Three Mechanisms FIG. 10 illustrates a method for combining the Cre/loxP system of patent application Ser. No. 08/473,168 (now U.S. Pat. No. 5,919,676) (hereby incorporated by reference, entitled "Adenoviral Vector System Comprising Cre-LoxP Recombination"), published as WO96/40955, the pIX system of patent application Ser. No. 08/719,217 (now U.S. Pat. No. 6,080,569), (hereby incorporated by reference, entitled "Improved Adenovirus Vectors Generated from Helper Viruses and Helper Dependent Vectors"), published as WO98/13510, and the endonuclease system of the present invention, for production of a helper dependent vector substantially free of helper virus.

Further to the teachings of copending patent application serial number 08/719,217 (now U.S. Pat. No. 6,080,569)

helper viruses having genomes of a size greater than the upper limit for packaging in a pIX-defective virion are provided therein. One embodiment of copending patent application serial number 08/719,217 (now U.S. Pat. No. 6,080,569) is the construction of a helper virus from two vectors. Preferably, the first vector includes a circularized, modified human adenovirus type 5 (Ad5) genome that is deleted for, or contains mutations in, the DNA sequence encoding pIX. This first vector is combined with a second vector containing overlapping viral DNA sequences to generate infectious Ad5, known as a helper virus having a modified pIX, and a genome size greater than the is upper limit for packaging in a pIX-defective virion. Alternatively, the size of the helper virus can be increased by the insertion of additional DNA sequences into the adenoviral genome, known as "stuffer" DNA. Bacterial plasmids are preferred vectors for obtaining the helper virus. However, other vectors may be employed to construct the helper virus, such as, for example, yeast plasmids.

Although not able to produce adequate proteins, particularly pIX, to permit its own packaging, the helper virus, described in the paragraph above and in patent application Ser. No. 08/719,217 (now U.S. Pat. No. 6,080,569), is able to produce all of the functions required for the packaging of a helper-dependent viral vector having a genome of appropriately reduced size (i.e., less than about 35 kb) and lacking substantial portions of the viral genome so that the helper-dependent vector DNA can be packaged in pIX-defective virions. Such helper virus and helper-dependent vector DNA may replicate when coinfected into appropriate host cells, but only the helper-dependent vector DNA can be packaged. Optionally, certain regions of the vectors and resulting viruses may be deleted, such as sequences in the Ad E1 or E3 regions that can be omitted from the viral genome without preventing the viral genome from replicating in such cells as may be permissive for replication of said genome in the form of infectious virus.

As is further disclosed as an embodiment of the invention of patent application Ser. No. 08/719,217 (now U.S. Pat. No. 6,080,569), a helper virus is provided that contains a deletion or mutation of pIX coding sequences and has a genome of such a size that it cannot be packaged in the absence of pIX, but can be propagated under permissive conditions, and used to support replication of a second virus, i.e., the helper-dependent vector, from which substantial portions of the viral genome have been deleted and substituted with foreign DNA having an overall DNA size that can be packaged. Under nonpermissive conditions, i.e., in the absence of pIX, the helper virus DNA described herein is unable to be packaged into infectious virions but the helper-dependent vector DNA, being smaller than ~35 kb in size, is able to be packaged into a virion capsid lacking pIX.

According to this aspect of the invention, a helper virus, named AdLC8ΔpIXSceI, comprising a genome of greater than about 35 kb and less than about 37 kb is produced, (if need be by insertion of "stuffer" DNA as shown), including an SceI endonuclease recognition site, which is inserted 3' to the adenoviral packaging signal, as described in the foregoing examples and written description. On either side of said packaging signal and said endonuclease recognition site is inserted a loxP recognition site for the Cre recombinase, as described in the foregoing examples and in WO96/40955. As described above, an embedded ITR is inserted on the 3' side of the internal loxP site, to permit repair following excision of the packaging signal and left hand ITR. In addition, a deletion in the adenovirus gene encoding the pIX gene product is introduced into the helper adenoviral genome, as described in WO98/13510.

A cell which expresses pIX and E1 is produced, to complement the deficiency in the helper virus, such that a helper virus having a genome of greater than 35 kb may be efficiently packaged, in spite of the absence of a functional pIX gene in said adenovirus genome. 293 cells are known to complement E1 deficiencies in adenoviruses. In addition, cells such as the VK2-20(pIX+) cell line have been produced and shown to complement pIX deficiency. Such cells are used for the propagation and rescue of the helper adenovirus, constructed as described herein.

The AdLC8ΔpIXSceI helper virus is co-infected or transfected, in plasmid form, into 293CreSceI(pIX−) cells, along with a helper dependent adenovirus vector having a genome of between about 20–35 kb. Such cells are produced from 293 cells by transfection of a plasmid encoding the Cre recombinase, and drug resistance, followed by selection of drug resistant cells and screening for cells which stably express the Cre recombinase. An identical strategy is employed to develop a cell line which stably expresses the SceI endonuclease.

The co-infected or co-transfected or electroporated cells excise packaging sequence from the helper virus at an efficiency of about 90%, preventing that percentage of helper virus from being packaged into virions. The helper dependent vector is unaffected, due to the absence of loxP sites flanking its packaging signal.

Any helper virus which escapes Cre-mediated excision of the packaging signal is prevented from being packaged, due to the excessive size of the helper adenovirus genome, and the absence of available pIX gene product, either from the viral genome or from the cell.

Finally, any helper virus which escapes Cre-mediated excision and which might otherwise be packaged, such as through genomic deletions which produce a genome of less than about 35 kb in length, are subject to SceI cleavage of the packaging signal, and ITR repair for continued trans provision of functions necessary for replication and packaging of the helper dependent vector. Thus, the only virions that are produced, including through reamplification in the 293CreSceI cells, are helper dependent vector constructs.

Example 12

Production and use of Helper Adenovirus Having Transposed Packaging Signals

Following the procedures of Hearing, P., and Shenk, T., Cell 33:695–703, (1983), helper adenovirus is produced wherein the packaging signal, an endonuclease recognition signal as described herein, and any loxP, FRT, or like recognition sites for Cre, FLP, or like recombinases, respectively, are transposed to the right end or another location in the helper adenoviral genome. By maintaining the relative orientation of these elements, similar activity of the endonuclease, recombinase and pIX helper virus packaging control systems described herein is expected, based on the methods and helper adenoviral constructs disclosed herein. Accordingly, those skilled in the art of adenoviral vector preparation will appreciate that, based on the instant disclosure, various modifications in the precise location of the various elements that comprise the helper adenovirus may be made without adversely affecting the functionality of the methods taught herein for production of helper dependent adenoviral vector preparations, substantially free of packaged helper adenovirus.

Example 13

Production of Cells Expressing Endonuclease

Those skilled in the art will appreciate that a number of techniques are available for production of cells expressing appropriate endonucleases for use according to this invention. Such methods may depend on use of an antibiotic or other resistance marker. We have found that it may be desirable to use a mutated or attenuated resistance marker gene in order to drive up the copy number of the vector encoding, and therefore the level of expression of Scei. It should also be appreciated that cells used according to this invention are not limited to 293 cells. 293Cre cells, may be used, as may any other cell which complements, for example, E1. Cells known in the art that may be used according to this invention, upon introduction of expressible endonuclease coding sequences, include, but are not limited to PER-C6 cells (see Fallaux, et al., "New Helper Cells and Matched Early Region 1-Deleted Adenovirus Vectors Prevent Generation of Replication-Competent Adenoviruses," Hum. Gene Ther., Sep. 1, 1998; 9(13):1909–1917), and 911 cells, (Fallaux, et al., "Characterization of 911: A New Helper Cell Line for the Titration and Propagation of Early Region 1-Deleted Adenoviral Vectors," Hum. Gene Ther. 1996, January 20;7(2):215–222).

Example 14

Cell Lines Expressing I-SceI

Figure 11:
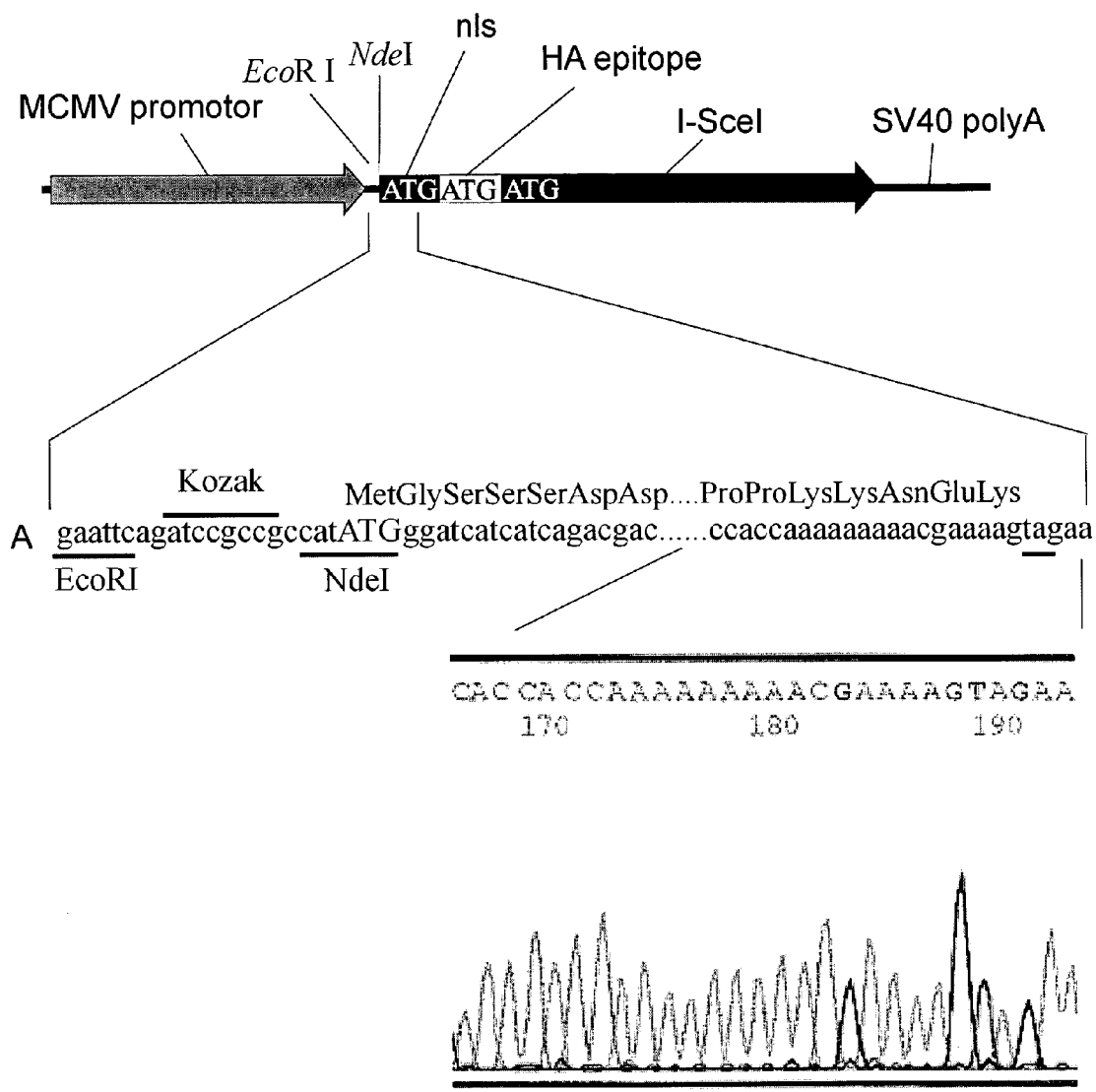
FIG. 11. Correction and optimization of the I-SceI gene. The plasmid pMH4SceI (a gift from M. Anglana and S. Bacchetti) was constructed by cloning the 853 bp EcoRI/SalI fragment containing the I-SceI gene from a plasmid containing the Sce I gene, pCMV-I-SceI (Rouet P, Smith F, Jasin M Expression of a site-specific endonuclease stimulates homologous recombination in mammalian cells. Proc Natl Acad Sci USA Jun. 21, 1994;91(13):6064–6068), into the EcoRI/SalI sites of pMH4 (available from Microbix Biosystems).) Sequence analysis (A) showed that the I-SceI gene in pMH4SceI contained a single base pair deletion (nine A's between nt 173 and 181 instead of ten) in the nuclear localization signal (see inset for sequence ladder, SEQ ID NO: 9 and SEQ ID NO: 10 for nucleic acids and SEQ ID NO:11 and SEQ ID NO:12 for peptide sequence) resulting in premature termination of translation at an immediately downstream TAG. The position of the Kozak consensus sequence relative to the start codon for I-SceI was also not optimal. Therefore, the sequence of the 5' end of the I-SceI coding sequence was corrected and optimized (new sequence shown in (B)). This modification was accomplished using synthetic oligonucleotides AB16751 and AB16752 (respectively, SEQ ID NO:13 and SEQ ID NO: 14 for the nucleic acids and SEQ ID NO: 15 and SEQ ID NO: 16 for the peptide sequences) as described in FIG. 12A.
Figure 13:
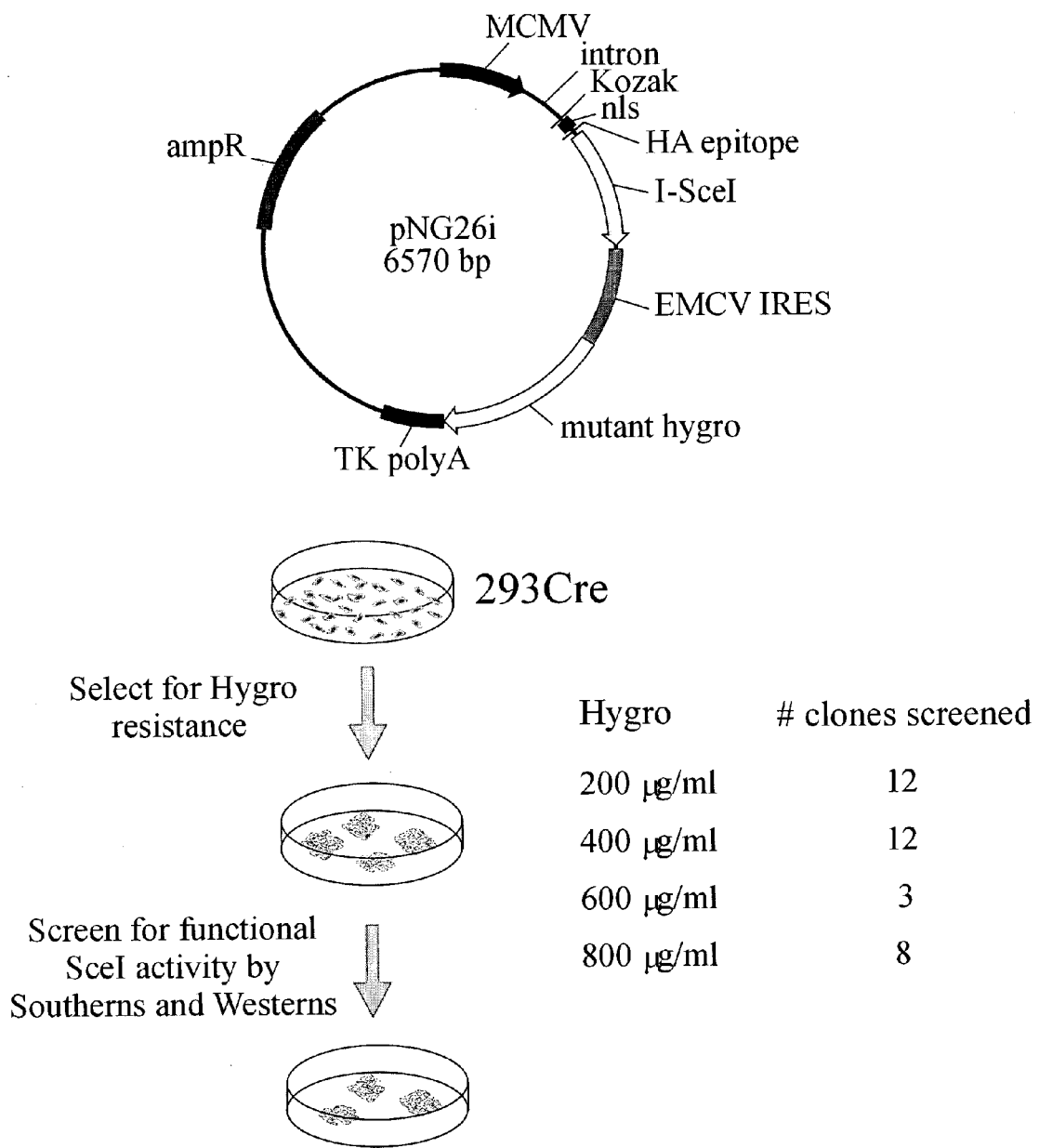
FIG. 13. Development of cell lines expressing I-SceI. 100 mm dishes of semiconfluent monolayers of 293Cre4 cells (Chen, L., Anton, M. and Graham, F. L. Production and characterization of human 293 cell lines expressing the site-specific recombinase Cre. Somat. Cell and Molec. Genet. 22: 477–488, 1996.) were transfected with 5 µg of pNG26i (FIG. 12B) by calcium phosphate coprecipitation (Graham, F. L. and van der Eb., A. J. A new technique for the assay of infectivity of human adenovirus 5 DNA. Virology 52, 456–467, 1973.). Three days post-transfection, hygromycin was added to the culture media at concentrations of 200, 400, 600 or 800 µg/ml. Following selection, individual hygromycin resistant colonies were isolated, expanded and analyzed for I-SceI expression by Southern (FIG. 14) and Western blot hybridization (FIG. 15).
Figure 14:
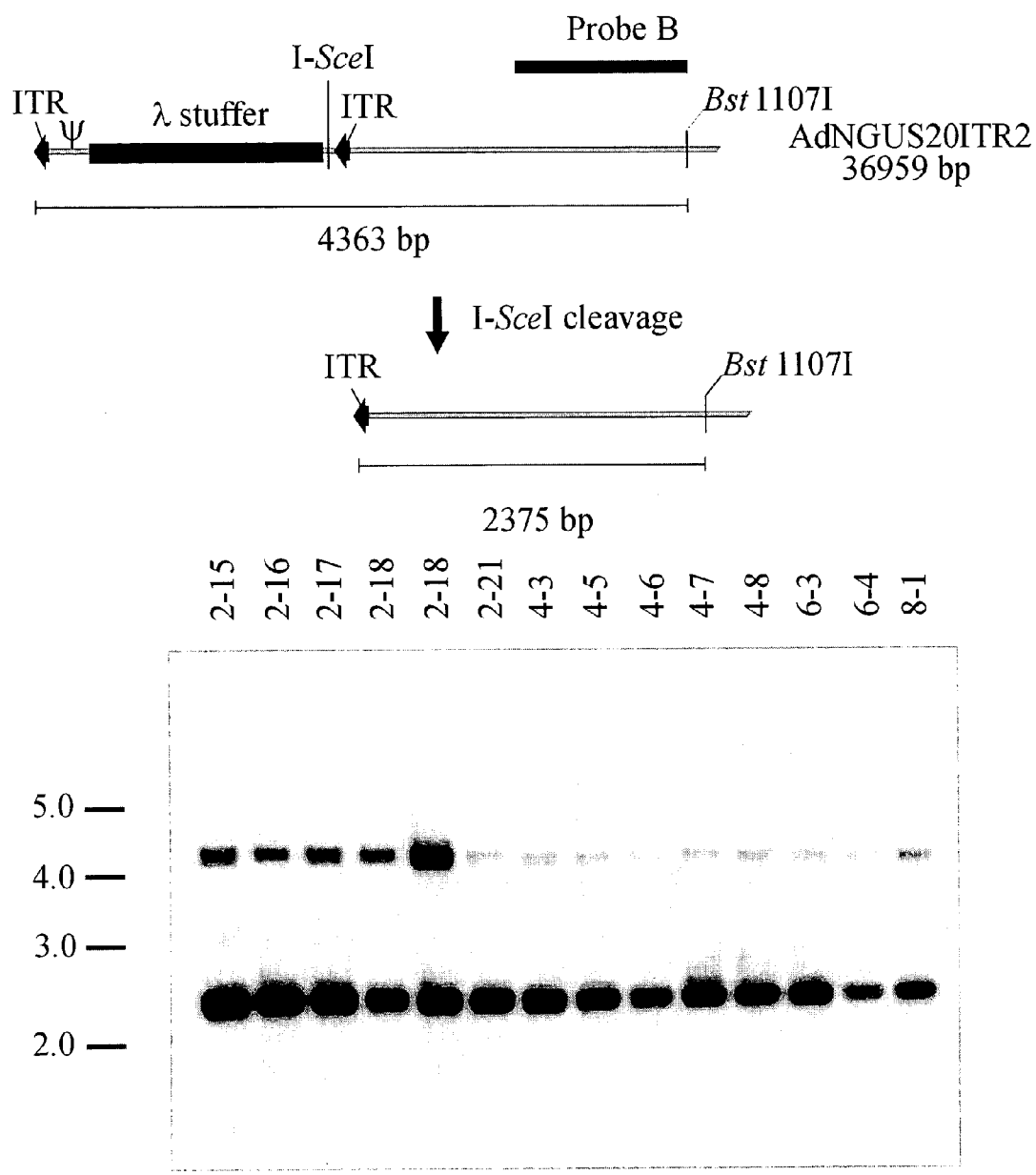
FIG. 14. Analysis of I-SceI activity in 293Cre4 cells transformed with pNG26i. 35 mm dishes of the indicated transformed cell line were infected with AdNGUS201TR2 (described in FIG. 21) at an moi of 1. 48 hrs post-infection, viral DNA was extracted and subjected to Southern blot hybridization with probe fragment B following digestion with Bst11071. In the presence of I-SceI cleavage, the 4.4 kb Bst11071 fragment of AdNGUS20ITR2 is expected to be converted to a 2.4 kb Bst11071 fragment.
Figure 15:
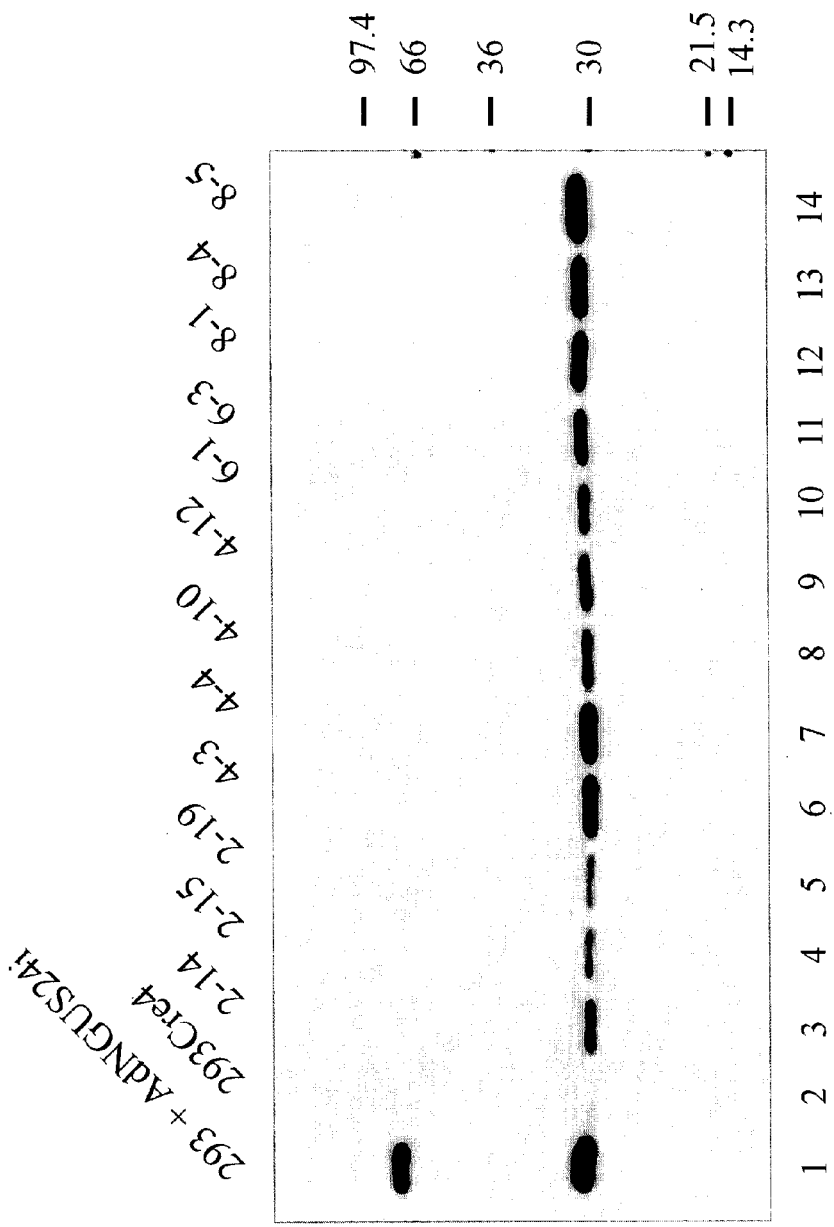
FIG. 15. I-SceI expression in 293Cre4 cells transformed with pNG26i determined by Western blot analysis. The Western shows I-SceI protein (31 kDa) in 293 cells 24 hrs after infection with AdNGUS24i at an moi of 5 for (lane 1) or in various 293Cre4 cells stably transformed with pNG26i (lanes 3 to 14). Lane 2 contains 293Cre4 cell extract as a negative control. Total protein was extracted by incubating cells with Radioimmunoprecipitation assay buffer for 30' on ice. Samples were centrifuged and total protein of the supernatant was determined using a quantitative colorimetric assay (Micro BCA assay reagent kit, Pierce). 2.5 µg of protein was fractionated on a 10% SDS-polyacrylamide gel and transferred to Immobilon P polyvinylidene difluoride membrane (Millipore) using a Transblot cell (Bio-Rad). The HA-tagged I-SceI protein is expected to be ~30.7 kDa and was detected using Anti-HA high affinity Rat monoclonal antibody [clone 3F10; 100 ng/ml in PBS-buffered skim milk (5%); Roche] and a peroxidase conjugated affinipure Donkey Anti-Rat IgG (H+L) [160 ng/ml in PBS-buffered skim milk (5%); Jackson Immuno Research Laboratories]. Chemiluminescence using an ECL Western Blotting Detection Kit (Amersham) and XAR5 film (Eastman Kodak Company) was used to monitor the peroxidase reaction. Molecular weights (kDa, Rainbow Marker; Amersham) are shown to the right. The band in lane 1 between 66 kDa and 97.4 kDa is specific to adenovirus infected cells and may represent a viral protein that binds to one of the Abs used in the hybridization.

After constructing pNG19-1F and using it to transform 293 and 293Cre cells and after establishing and characterizing a number of transformed cell lines, we discovered that I-SceI activity in said lines, though detectable, was low. To determine the reasons for this we sequenced the I-SceI expression cassette in pNG19-1F and its parent pMH4SceI (FIG. 9) and discovered that the I-SceI construct had a mutation in the 5' end that introduced a frame shift and a termination mutation that resulted in lower than desired I-SceI expression levels. The structure of the relevant portions of pMH4SceI and the sequence of the region in question are shown in FIG. 11. The plasmid pCMV-I-SceI obtained from M. Jasin, Sloane-Kettering, was found to contain the same frame shift mutation (a missing A in a string of 10 A's in the nuclear localization signal (nls) that Jasin and coworkers had engineered at the 5' end of the I-SceI coding sequences). That we obtained any activity at all was probably due to either reinitiation of translation at a downstream ATG or to ribosome slippage during translation through the string of A's in the nls. In any case, we concluded that we might be able to improve the levels of I-SceI activity in transformed cell lines if we corrected the mutation, and at the same time we decided to improve the Kozak sequence since that in the original Jasin construct was not an optimal Kozak sequence. The resulting plasmid, pNG26i (FIG. 12A), was used to transform 293Cre4 cells (U.S. Pat. No. 5,919,676 and Chen, L., Anton, M. and Graham, F. L. Production and characterization of human 293 cell lines expressing the site-specific recombinase Cre. Somat. Cell and Molec. Genet. 22: 477–488, 1996.), and hygromycin resistant cell lines were isolated (FIG. 13) and analyzed for I-SceI expression in a functional assay that measured I-SceI mediated cleavage of viral DNA containing an SceI site (FIG. 14) and directly for I-SceI protein production by Western blot hybridization (FIG. 15). Several transformed cell lines expressed satisfactory levels of I-SceI, and two of these, 2-16 and 4-7, were selected for further experiments. We also rescued the I-SceI gene with the corrected DNA sequence and the optimized Kozak sequence into an Ad expression vector (AdNG24i) by cotransfection of 293 cells with pNG24i (FIG. 12A) and pBHG10. Both the cell lines and the vector expressed much higher levels of functional I-SceI than did their counterparts that carried the frame shifted mutant I-SceI construct.

Example 15

Helper Viruses

Figure 16:
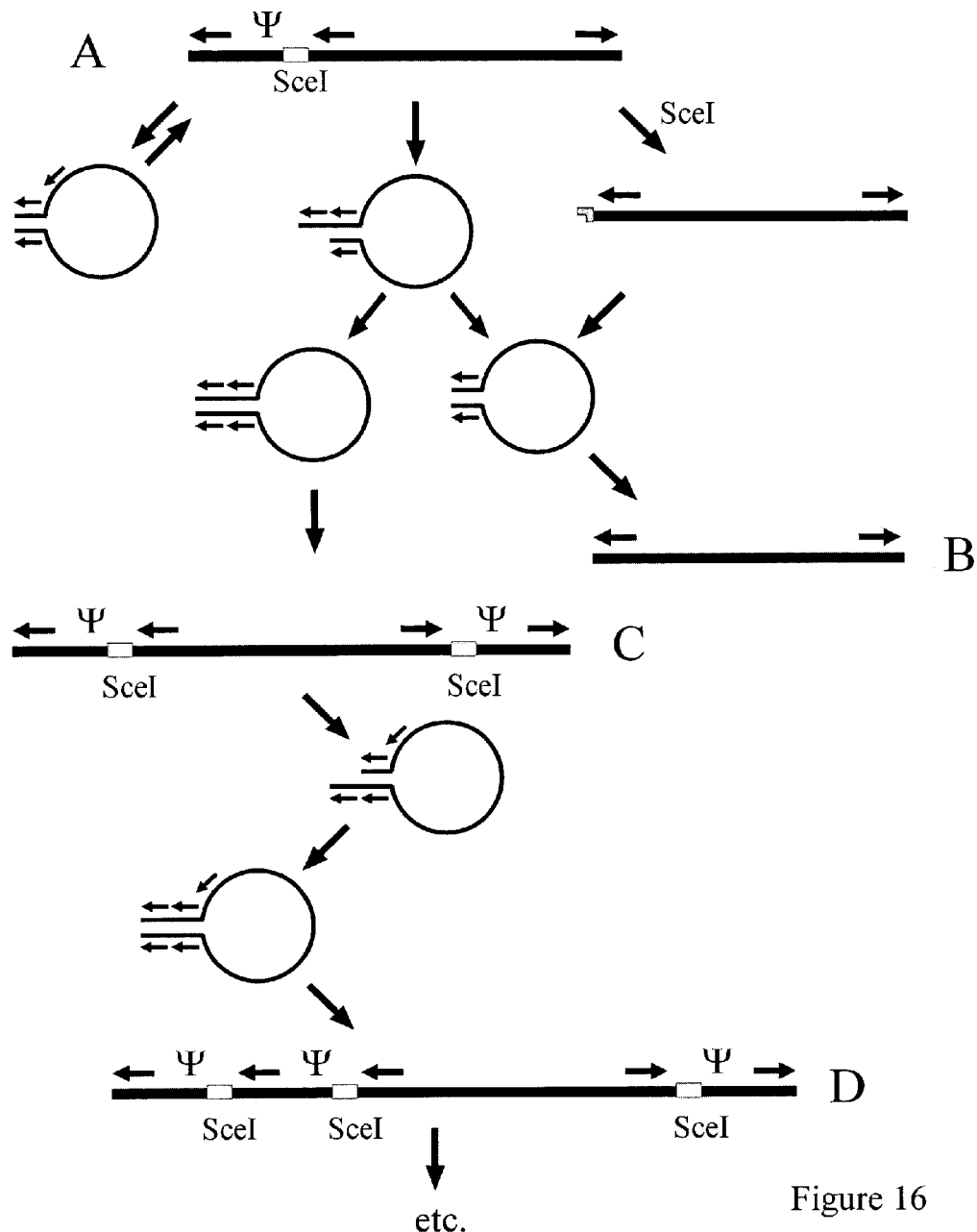
FIG. 16. Modifications to the ends of Ad DNA by panhandle formation and various repair modes. An intermediate step in adenoviral DNA replication occurs though pairing of the terminal ITRs of single stranded DNA to generate a panhandle structure. For viruses bearing an internal ITR as depicted in (A), two possible ITR pairings may occur: pairing between the two terminal ITRs or pairing of the internal ITR with the rightmost ITR. In the former case, DNA replication will result in a progeny molecule that is identical to the parental DNA. In the latter case, two possible progenies, both different from the parental molecule may result: one bearing four ITRs and one bearing two ITRs. The molecule bearing two ITRs (B) can replicate but cannot be packaged into virions owing to the loss of the packaging signal (ψ) thus representing an ideal helper genome. If the viral DNA bears a Sce-I site between the leftmost ITR and the internal ITR, as depicted in (A), then this species can also be generated by I-SceI cleavage followed by panhandle formation and repair. In contrast, the species bearing four ITRs (C) can replicate as well as be packaged. This species can undergo further rearrangements through panhandle formation of any two ITRs during replication to generate a plethora of different species. Propagation of these variants is limited only by their size.
Figure 17:
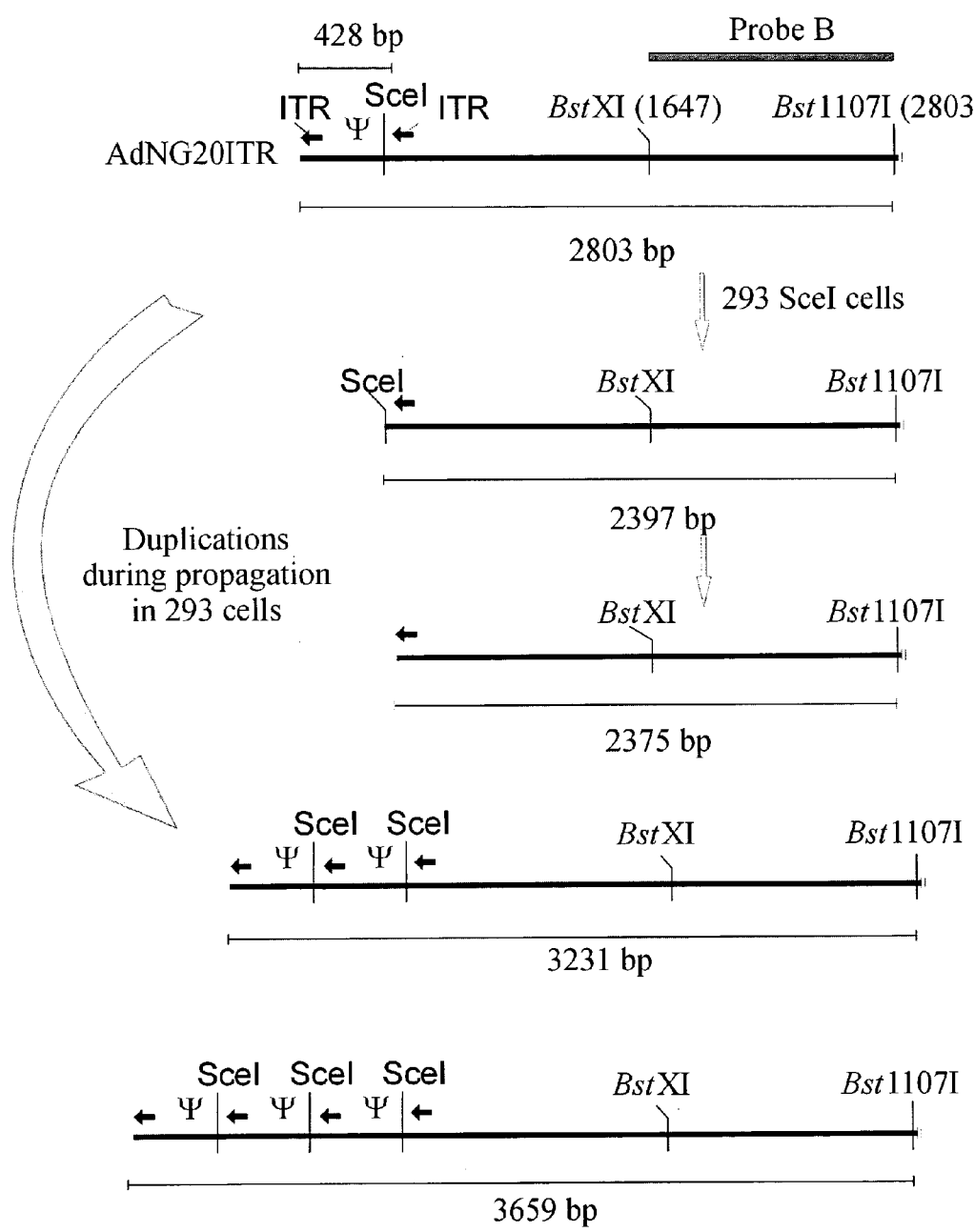
FIG. 17. Left end structures after duplication of DNA segments by panhandle formation. The left end of AdNG20ITR is present on a 2.8 kb Bst1107I fragment. Cleavage by I-SceI followed by repair using the internal ITR results in a 2.4 kb fragment. In the absence of I-SceI cleavage, the genome of AdNG20ITR may undergo rearrangements mediated by the internal ITR as depicted in FIG. 16. These rearrangements can extend the left end of the genome by multiples of 428 bp resulting in Bst1107I fragments of 3.2 kb, 3.7 kb, etc. Similarly, the right end of the genome can also be extended (not shown).
Figure 18:
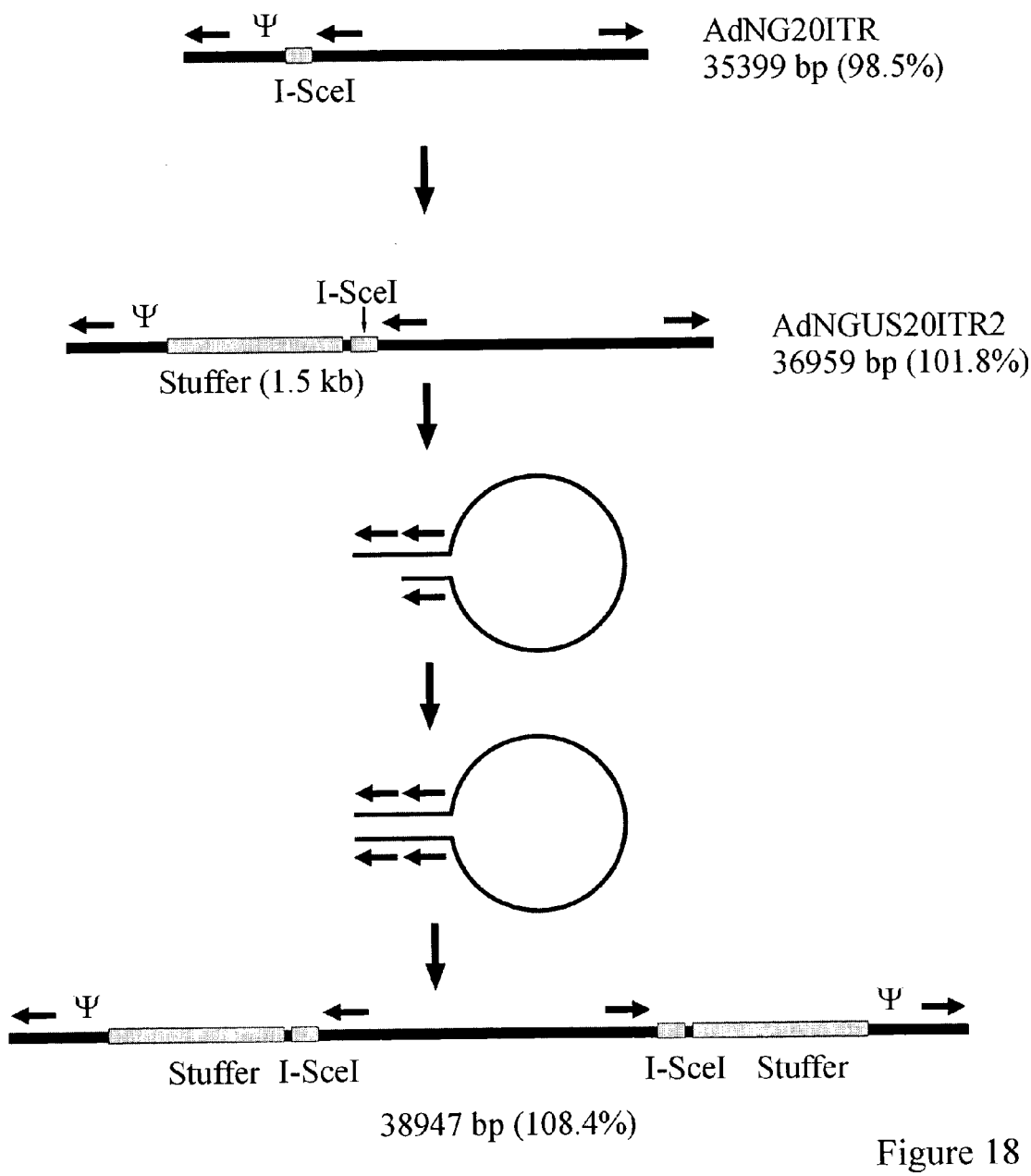
FIG. 18. Strategy to block propagation of rearranged viruses bearing an internal ITR. A simple strategy to block propagation of rearranged virus due to the presence of the internal ITR is to render the rearranged products too large to be packageable. To this end, a stuffer segment can be introduced into the viral genome between the leftmost and internal ITR as depicted. While this modification will not prevent rearrangement, it will prevent the rearranged products from being propagated since the genomes of these viral variants will exceed the upper packaging limit.
Figure 19:
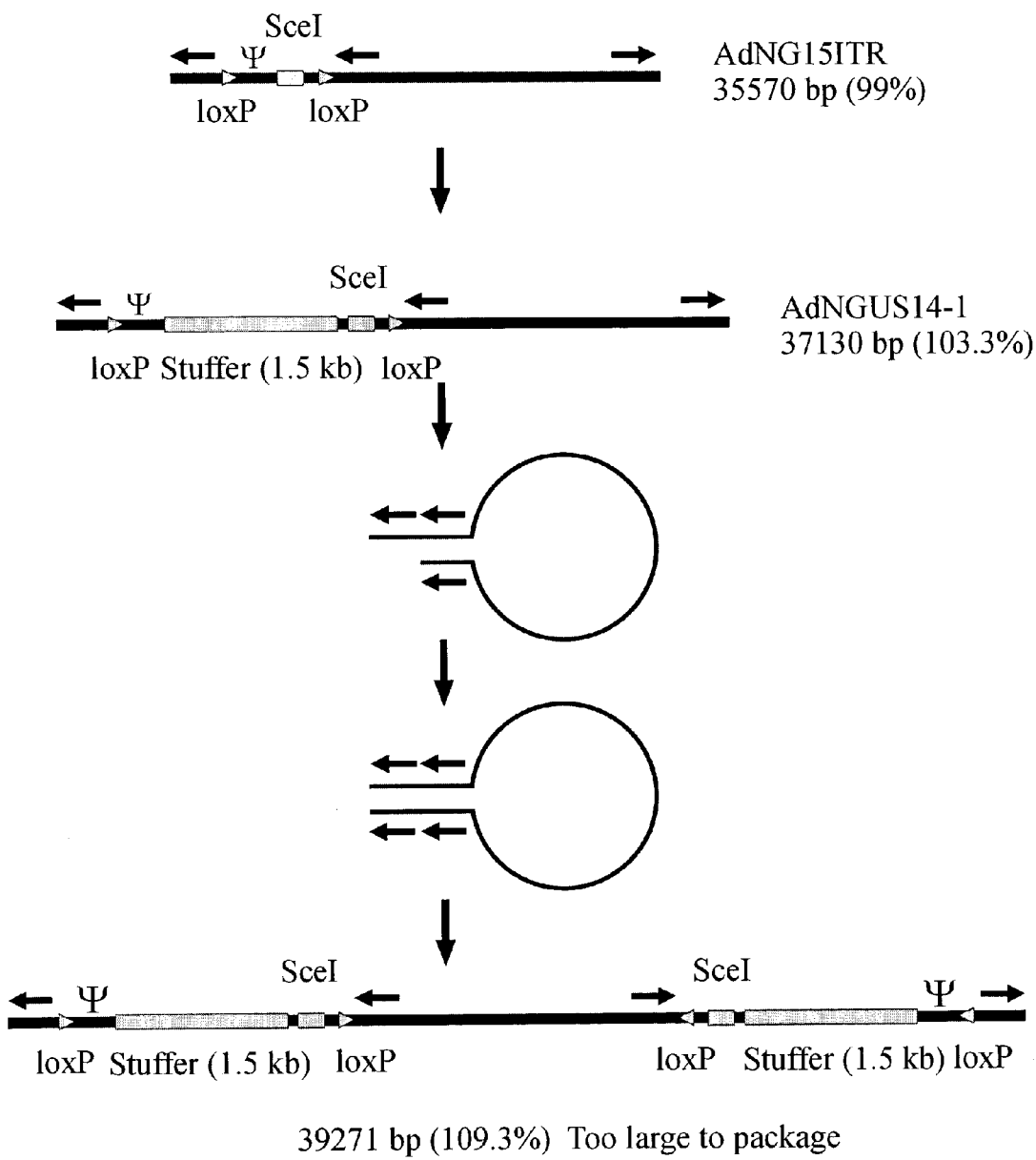
FIG. 19. Strategy to block propagation of rearranged viruses bearing an internal ITR. As in FIG. 18 except for the presence of loxP sites in the viral genome as depicted.
Figure 20:
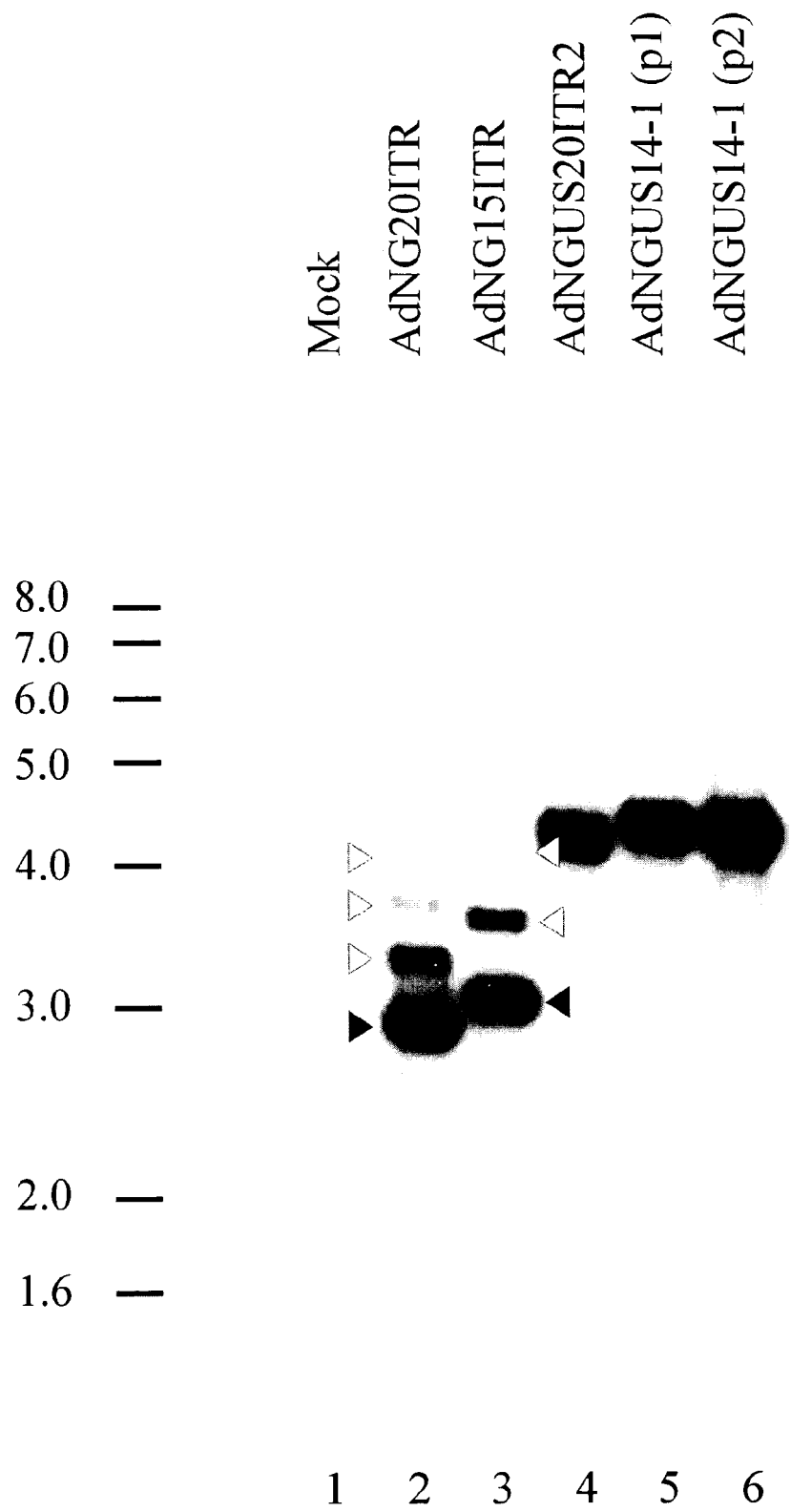
FIG. 20. Effectiveness of stuffer in eliminating propagation of internal ITR-mediated rearranged genomes. 35 mm dishes of 293 cells were infected with the indicated virus at an moi of 1. At 48 hrs post-infection, viral DNA was extracted and analyzed by Southern blot hybridization with probe fragment B following digestion with Bst1107I. As shown, a 2.8 kb Bst1107I fragment (black triangle in lane 2) is expected from the unrearranged genome of AdNG20ITR depicted in FIG. 17. However, additional bands at higher molecular sizes (white triangles in lane 2) are also observed. These correspond to the internal ITR-mediated rearrangement products depicted in FIG. 17. The intensity of these bands suggests that the rearranged species can propagate and may be expected to contribute to further rearrangements. Lane 3 shows the results of similar analysis for a second helper virus, AdNG15ITR indicating that formation of variant viruses is a general phenomenon for viruses with internal ITRs. Propagation of such rearranged viruses is virtually eliminated by inclusion of a stuffer segment as in the case of AdNGUS20ITR2 (lane 4) as only the expected 4.4 kb Bst1107I fragment from the parental virus is observed. Similarly, propagation of the rearrangement products of AdNG15ITR was observed (white triangles in lane 3), but virtually eliminated by inclusion of a stuffer as shown for AdNGUS14-1 in lanes 5 and 6.

FIG. 7 herein illustrates the structure of several helper virus genomes containing SceI sites at the left end. These were shown to be susceptible to I-SceI cleavage and the internal ITR's of AdNG15ITR and AdNG20ITR were shown to produce functional ends after I-SceI cleavage by panhandle formation (ITR annealing) and ITR repair (FIG. 1). However, during propagation of these helpers in 293 cells we found that the internal ITR also resulted in rearrangements that resulted in tandem amplification of the DNA segment between the extreme end of the parental genome and the internal ITR. This could occur via mechanisms illustrated in FIG. 16 resulting in variant viral genomes of the kind illustrated in FIG. 17 wherein the helper virus AdNG20ITR is propagated in 293 cells and successive rounds of panhandle formation and extension of the sort illustrated in FIG. 16 results in viruses with various tandem repetitions of the DNA segment containing an ITR, a packaging signal, and an SceI site. Similar repeats are present at the right end of the genome but are not illustrated in the Figure. Formation of variant viruses with multiple copies of the packaging signal and I-SceI site and internal ITR was deemed undesirable because it would result in a requirement for increased levels of I-SceI enzyme to ensure complete digestion of helper virus DNA. Therefore, we redesigned the helper viruses to prevent duplication of terminal DNA segments. This was accomplished by introduction of "stuffer" DNA sequences between ψ and the internal ITR such that duplication of the resulting DNA segment would result in a viral genome which is too large to be packaged into virions (examples not meant to be limiting are illustrated in FIGS. 18 and 19). The experiment illustrated in FIG. 20 provides evidence for the tandem repetitions diagramed in FIG. 17 and provides evidence that the use of a stuffer sequence is a successful strategy, as the helper viruses AdNGUS20ITR2 and AdNGUS14-1 did not produce variant progeny. Therefore, helper viruses with stuffer sequences between the leftmost ITR and the internal ITR are a preferred embodiment of the invention as they tend not to undergo rearrangement of the kind illustrated in FIGS. 16 and 17 during propagation in 293 cells or more accurately, any viral DNA molecules that have undergone such rearrangements are not packaged and hence are not propagated.

Various helper viruses used in these and subsequent experiments are illustrated in FIG. 21 and methods for their construction are diagramed in FIG. 22. We examined the effect of placing the SceI recognition site at a number of different locations: between the X DNA stuffer and the internal ITR (AdNGUS20ITR2), flanking ψ and the λ DNA stuffer with 2 SceI sites, or placing the SceI site between the external ITR and the packaging signal. These examples are not meant to be limiting as one could readily make other constructs, for example, by placing the SceI site between ψ and the stuffer or by flanking only the packaging signal with SceI sites. The shuttle plasmids containing the modified left ends illustrated in FIG. 21 were constructed by standard methods as illustrated in FIGS. 22 and 23 and rescued into virus by cotransfection with an Ad genomic plasmid (Bett, A. J., Haddara, W., Prevec, L. and Graham, F. L. An efficient and flexible system for construction of adenovirus vectors with insertions or deletions in early regions 1 and 3. Proc. Natl. Acad. Sci. US 91: 8802–8806, 1994., Parks, R. J., Chen, L., Anton, M., Sankar, U., Rudnicki, M. A. and Graham, F. L. A new helper-dependent adenovirus vector system: removal of helper virus by Cre-mediated excision of the viral packaging signal. Proc. Natl. Acad. Sci. U.S. 93: 13565–13570, 1996.)

Example 16

I-SceI Mediated Cleavage of Helper Virus DNA

To test the effectiveness of I-SceI constitutively expressed by transformed 293Cre4 cell lines 2-16 and 4-7 in cleaving SceI sites in helper virus DNA, we infected these cells and parental 293Cre4 cells with helper viruses AdNGUS20ITR2, AdNGUS41 and AdNGUS43 and analyzed the left end DNA structures by Southern blot hybridization analysis using a probe that hybridized to Ad DNA sequences between the internal ITR and a Bst11071I site, as shown in FIG. 21. The results are presented in FIG. 24. Parental viruses contain a left end Bst11071I fragment of about 4.4–4.5 kb and this is readily seen in lanes 1, 4, and 7 containing DNA from infected 293Cre4 cells. In contrast SceI cleavage followed by panhandle formation and ITR repair would be expected to produce smaller fragments of about 2.4 kb as diagramed for AdNGUS20ITR2 in FIG. 25. Fragments of the expected size are indeed generated at high efficiency in infected 2-16 and 4-7 cells that express I-SceI and there is a concomitant reduction in the amount of the parental 4.4 kb fragment. However, two additional fragments of approximately 2.7 kb and 8.6 kb are seen in lanes 5 and 6 that were not expected and an additional fragment of about 8.4 kb was present in lanes 8 and 9. FIGS. 26 and 27 illustrate the mechanisms that generate these novel fragments in helper virus infected cells that express I-SceI. It can be seen that joining of viral DNA ends (a form of double strand break repair that is known to be highly efficient in vertebrate cells) after SceI cleavage results in structures that can give rise to the observed fragments. In FIG. 26 it can be seen that joining of fragments A and C results in a virus DNA with a deleted packaging signal and a left end Bst11071I fragment of 2.7 kb. From the Southern blot hybridization results of FIG. 24 it can be seen from the intensity of this band in lanes 5 and 6 that this rejoining reaction is highly efficient. Since there is little parental DNA visible in these lanes, i.e. little or no 4.5 kb fragment, it will be appreciated by those skilled in the art, based on the present disclosure, that flanking the packaging signal with SceI sites and infecting I-SceI expressing host cells is an effective method for eliminating packageable helper virus DNA while retaining ability of the helper virus genome to replicate. The large fragments of 8.4–8.6 kb seen in lanes 5 and 6 and 8 and 9 of FIG. 24 also represent unpackageable viral DNA since in the species that give rise to these bands, illustrated at the bottom of FIGS. 26 and 27, the packaging signal is internal and consequently nonfunctional. Also the viral genomes formed by this head to tail joining are too large to be packaged even were they to contain functional packaging signals.

The breakage rejoining reaction illustrated in FIG. 26 that results in deletion of the DNA segment comprising the packaging signal and λ DNA stuffer is operationally very similar to the result of infecting a 293Cre cell line with a virus in which a comparable DNA segment is flanked by lox sites, as described in U.S. Pat. No. 5,919,676, and in Parks, R. J., Chen, L., Anton, M., Sankar, U., Rudnicki, M. A. and Graham, F. L. A new helper-dependent adenovirus vector system: removal of helper virus by Cre-mediated excision of the viral packaging signal. Proc. Natl. Acad. Sci. U.S. 93: 13565–13570, 1996. One major difference is that the breakage rejoining reaction is effectively irreversible, whereas excision mediated by Cre recombinase is, in principle, a reversible reaction. The reason the SceI-double strand break repair pathway is effectively unidirectional is that double strand break repair is error prone and results in small deletions at the site of rejoining. Furthermore, although this is not necessarily essential, the SceI sites in AdNGUS41 are oriented in opposite orientation (the SceI recognition sequence is nonpalindromic), so that rejoining of the sites is not through a simple sticky end ligation reaction, but rather requires classic double strand break repair which inevitably will result in a junction that does not contain an SceI recognition site.

A further illustration of the effectiveness of I-SceI mediated cleavage in elimination of helper virus from cells infected with helper viruses of the sort illustrated in FIG. 21 is provided by the results shown in Table I wherein cells expressing I-SceI were used to titrate viruses in a plaque forming assay. The reduction in titre on I-SceI expressing cells relative to 293 cells is illustrative of the effectiveness by which helper virus DNA is prevented from being packaged into virions. Interestingly, the reduction in titre (over 800 fold) was greatest for the AdNGUS41 virus that contains a packaging signal flanked by two SceI sites, consistent with the results of the Southern blot hybridization analysis presented in FIG. 24 wherein little or no detectable parental helper virus DNA was evident. Importantly, the SceI expressing cell lines 2-14, 4-3, 4-4, 6-3 and 8-4 that were derived from 293Cre4 cells still express Cre recombinase, as indicated by the reduction in titre of AdLC8luc virus which contains a floxed packaging signal. Furthermore it can be seen that the reduction of titre for helper viruses containing SceI sites is as great as or greater than the reduction due to action of Cre on AdLC8cluc virus in 293Cre4 cells relative to 293 cells, indicating that this new system for prevention of packaging of helper viruses is at least as effective as the Cre-lox system of U.S. Pat. No. 5,919,676. From the fact that the new cell lines disclosed herein containing and expressing I-SceI also continue to express Cre, it will be appreciated by those skilled in the art that one can readily combine the use of Cre-lox with the new SceI system to maximally reduce the levels of helper virus contamination in helper dependent vector preparations. Examples of helper viruses that contain both lox sites and SceI sites, not meant to be limiting, are illustrated in FIG. 7 and in FIG. 19. An illustration of the effectiveness of a helper virus containing an SceI site and embedded ITR (AdNGUS20ITR2) in amplification of a helper dependent vector is provided in FIG. 31. It can be seen that the amplification efficiency is comparable to that obtained with the Cre-lox system.

Example 17

Use of the DNA Cleavage-Rejoining Process in Multiple Applications

The surprisingly high efficiency of joining of viral DNA fragments generated by I-SceI mediated cleavage disclosed herein and the operational similarities of this process to Cre-lox mediated excision suggest a number of applications besides the use of SceI to eliminate helper virus in a helper dependent vector system. For example, as illustrated in FIG. 28, based on the present disclosure, one skilled in the art could readily construct a vector containing an expression cassette in which expression of a cDNA is regulated by an SceI dependent molecular switch wherein SceI cleavage and DNA rejoining results in excision of a DNA fragment (a "spacer") that otherwise inhibits expression of the cDNA. This example is not meant to be limiting as one skilled in the art would appreciate that one could design and construct a switch such that expression is turned off in the presence of I-SceI by, for example, flanking the promoter of an expression cassette with SceI sites or by flanking the cDNA with SceI sites. Furthermore the use of I-SceI mediated cleavage in combination with efficient DNA fragment rejoining would not be limited to Adenovirus vectors but could equally be employed with other viral vectors or with any system for delivery of DNA to mammalian cells such as transfection with plasmid DNA.

The enzyme I-SceI need not be constitutively expressed by the host cell described hereinabove. A vector such as AdMH4SceI and AdNG24i, can be used to deliver an I-SceI expression cassette to mammalian cells for expression of the enzyme therein. The enzyme could also be expressed from plasmid DNA that can be delivered to mammalian cells by a variety of means or could be expressed from other viral vectors. It should also be noted that the examples provided herein are not limited to mammalian cells as the double strand break repair process is highly efficient in other vertebrate cells.

The expression cassette illustrated in FIG. 28 need not be located on a viral genome for the SceI dependent molecular switch to be operational. Such a cassette or a variety of appropriately designed cassettes could be introduced into the genome of mammalian cells and I-SceI expression in said cells could be induced by delivery of the I-SceI gene through transfection with plasmid DNA or through infection with a viral vector carrying an expression cassette with an I-SceI gene or the I-SceI gene could be integrated into the cellular chromosome, but its expression could be regulated so that I-SceI production is induced when and as desired to initiate the excision and double strand break repair process and its consequent up or down regulation of an SceI dependent expression cassette. An example, not meant to be limiting, is illustrated in FIG. 29 wherein a transgenic animal with a genome containing a gene under the control of an SceI susceptible molecular switch is infected with a vector expressing I-SceI. Expression of I-SceI and subsequent double strand break repair leads to excision of DNA and, following double strand break repair, in the illustrative example, results in expression of β-galactosidase. Use of a transgenic animal in this example is not meant to be limiting as one skilled in the art will appreciate that one could establish cells in culture containing similar expression cassettes regulated by cleavage rejoining reactions.

Use of SceI cleavage and double stand break repair readily lends itself to other applications one of which is illustrated in FIG. 30 wherein excision of the pIX coding sequences abolishes expression of pIX and leads to a method for production of helper dependent vectors that are free of helper virus.

An example illustrative of SceI cleavage at an SceI site in chromosomal DNA is provided in FIG. 32 in which a cell line transformed with a DNA containing an SceI site (such as 293.1 cells) is infected with an Ad vector (AdMSceI) expressing SceI resulting in DNA cleavage at said SceI site.

All patents, patent applications, publications, texts and references discussed or cited herein are incorporated by reference to the same extent as if each individual publication or patent application was specifically and individually set forth in its entirety. Nothing herein is to be construed as an admission that the invention is not entitled to antedate such disclosures by virtue of prior invention. In addition, all terms not specifically defined are first taken to have the meaning given through usage in this disclosure, and if no such meaning is inferable, their normal meaning. Where a limitation is described but not given a specific term, a term corresponding to such limitation may be taken from any references, patents, applications, and other documents cited herein, or, for an application claiming priority to this application, additionally from an Invention Disclosure Statement, Examiner's Summary of Cited References, or a paper otherwise entered into the file history of this application.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Thus, for the above variations and in other regards, it should be understood that the examples and embodiments described herein are for illustrative purposes only and that various modifications or changes in light thereof will be suggested to persons skilled in the art and are to be included within the spirit and purview of this application and the scope of the appended claims.

Also, although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included in the scope of this invention as defined in the following claims. In the claims, means-plus-function clauses and step-plus-function clauses are intended to cover the structures described herein as effectuating or performing the recited function and to cover not only structural equivalents, but also to cover equivalent structures as one of ordinary skill in the art would understand equivalence with regard to a any means or any step that will achieve a stated function in an equivalent manner. For instance, a "means to propagate said helper dependant virus" should be taken to include methods now or later known to those of skill in the art regardless of differences in the exact steps and reagents required to achieve this function.

TABLE 1

Titrations of Ad viruses containing SceI sites on various cell lines[a].

| | Cell lines | | | | | | |
|---|---|---|---|---|---|---|---|
| Viruses | 293 | 293Cre4 | 2-14 | 4-3 | 4-4 | 6-3 | 8-4 |
| AdNGUS20ITR2[b] | $5.15 \times 10^9$ | $6 \times 10^9$ | $5.4 \times 10^7$ | $5.35 \times 10^7$ | $4.4 \times 10^7$ | $6.15 \times 10^7$ | $6.4 \times 10^7$ |
| average | $5.6 \times 10^9$ | | | | $5.5 \times 10^7$ (↓ 102 fold) | | |
| AdNGUS41[c] | $4.6 \times 10^{10}$ | $6 \times 10^{10}$ | $1.25 \times 10^8$ | $4 \times 10^7$ | $3.5 \times 10^7$ | $6.5 \times 10^7$ | $6.5 \times 10^7$ |
| average | $5.3 \times 10^{10}$ | | | | $6.6 \times 10^7$ (↓ 803 fold) | | |
| AdNGUS43[d] | $1.15 \times 10^{11}$ | $4.25 \times 10^{10}$ | $5 \times 10^8$ | $7.5 \times 10^8$ | $9 \times 10^8$ | $8.5 \times 10^8$ | $1.25 \times 10^9$ |
| average | $7.9 \times 10^{10}$ | | | | $8.5 \times 10^8$ (↓ 93 fold) | | |
| AdLC8cluc[e] | $4.3 \times 10^9$ | $4.85 \times 10^7$ | $3.5 \times 10^7$ | $2.1 \times 10^7$ | $3.25 \times 10^7$ | $2.1 \times 10^7$ | $3.4 \times 10^7$ |
| average | | (↓ 89 fold) | | | $2.89 \times 10^7$ (↓ 149 fold) | | |
| AdCAMCIL-2[f] | $5.2 \times 10^{10}$ | $5.5 \times 10^{10}$ | $2.5 \times 10^{10}$ | $3.3 \times 10^{10}$ | $3.1 \times 10^{10}$ | $3.95 \times 10^{10}$ | $4.15 \times 10^{10}$ |

[a]The indicated viruses were titrated on 293, 293Cre4 and the 293Cre4 derived I-SceI expressing cells lines 2-14, 4-3, 4-4, 6-3 and 8-4.
[b]An average of 102-fold reduction in titre was observed on I-SceI expressing cells compared to 293 and 293Cre4 cells.
[c]An average of 803-fold reduction in titre was observed on I-SceI expressing cells compared to 293 and 293Cre4 cells.
[d]An average of 93-fold reduction in titre was observed on I-SceI expressing cells compared to 293 and 293Cre4 cells.
[e]An 89-fold reduction in titre was observed on 293Cre4 cells compared to 293 cells. An average of 149-fold reduction in titre was observed on the 293Cre4 derived I-SceI expressing cells compared to 293.
[f]Control virus used to compare the plaguing efficiencies of the various cell lines (unaffected by Cre or I-SceI).

What is claimed is:

1. A helper adenovirus nucleic acid sequence comprising a packaging signal, an inserted endonuclease recognition site, a first adenoviral inverted terminal repeat (ITR) located at one end of, and a second adenoviral ITR located at the other end of, the nucleic acid sequence, and a third adenoviral ITR located between the first and second adenoviral ITRs, wherein: (a) said endonuclease recognition site is for an endonuclease that does not cleave anywhere else in said helper adenovirus nucleic acid sequence, and wherein said endonuclease recognition site is disposed at a location in said helper adenovirus nucleic acid sequence 3' to said packaging signal; and (b) wherein said third adenoviral ITR is disposed at a location in said helper adenovirus nucleic acid sequence 3' to said endonuclease recognition site.

2. A helper adenovirus nucleic acid sequence comprising a packaging signal, an endonuclease recognition site, a first ITR located at one end of, and a second ITR located at the other end of, the nucleic acid sequence, and third ITR located between the first and second ITRs, wherein: (a) said endonuclease recognition site is for an endonuclease that does not cleave anywhere else in the helper adenovirus nucleic acid sequence, and wherein said endonuclease recognition site is disposed at a location in said helper adenovirus nucleic acid sequence 3' to said packaging signal; (b) said third ITR is disposed at a location in said adenovirus 3' to said endonuclease recognition site; and (c) said packaging signal is flanked on either side thereof by recognition sites for a recombinase, such that upon contact of said helper adenovirus nucleic acid sequence with said recombinase, said packaging signal is excised.

3. The helper adenovirus nucleic acid sequence according to claim 2 wherein said recognition site for a recombinase is a loxP site, and said recombinase is Cre, or wherein said recognition site for a recombinase is a FRT site, and said recombinase is FLP.

4. The helper adenovirus nucleic acid sequence according to claim 2 wherein said endonuclease recognition site is flanked on either side thereof by recognition sites for a recombinase, such that upon contact of said helper adenovirus nucleic acid sequence with said recombinase, said endonuclease recognition site is excised.

5. The helper adenovirus nucleic acid sequence according to claim 4 wherein said recognition sites for a recombinase are loxP sites, and said recombinase is Cre, or wherein said recognition sites for a recombinase are FRT sites, and said recombinase is FLP.

6. The adenovirus according to claim 2 wherein said packaging signal and said endonuclease recognition site are flanked by recognition sites for a recombinase, such that upon contact of said helper adenovirus nucleic acid sequence with said recombinase, said packaging signal and said endonuclease recognition site are excised.

7. The helper adenovirus nucleic acid sequence according to claim 6 wherein said recombinase recognition sites are loxP recognition sites, and said recombinase is Cre, or wherein said recognition sites for a recombinase are FRT sites, and said recombinase is FLP.

8. The helper adenovirus nucleic acid sequence according to claim 2 wherein said endonuclease recognition site is for the endonuclease SceI.

9. The helper adenovirus nucleic acid sequence according to claim 2 further comprising a deletion or modification in a nucleic acid sequence encoding an adenovirus pIX gene product, wherein the helper adenovirus nucleic acid sequence is not able to produce pIX proteins for its own packaging into an infectious adenoviral virion.

10. A system for producing a helper dependent adenovirus vector comprising: (a) a helper adenovirus nucleic acid sequence comprising a packaging signal, an inserted endonuclease recognition site, a first ITR located at one end of, and a second ITR located at the other end of, the nucleic acid sequence, and a third ITR located between the first and second ITRs, wherein: (i) said endonuclease recognition site is for an endonuclease that does not cleave anywhere else in the helper adenovirus genome, and wherein said endonuclease recognition she is disposed at a location in said helper adenovirus nucleic acid sequence 3' to said packaging signal; and (ii) said third ITR is disposed at a location in said helper adenovirus nucleic acid sequence 3' to said endonuclease recognition site; and (b) a helper dependent adenovirus vector comprising a left adenoviral ITR, a right adenoviral ITR, an adenoviral packaging signal and additional nucleic acid sequences, such that upon co-introduction of said helper dependent adenovirus vector into a cell with said helper adenovirus nucleic acid sequence, said helper dependent adenovirus vector is packaged.

11. The system according to claim 10 wherein said packaging signal of said helper adenovirus nucleic acid sequence is flanked on either side by a recombinase recognition site.

12. The system according to claim 11 wherein said recombinase recognition sites are loxP recognition sites, and said recombinase is Cre, or wherein said recognition site for a recombinase is a FRT site, and said recombinase is FLP.

13. The system according to claim 11 further comprising a cell which expresses said endonuclease which cleaves said endonuclease recognition site.

14. The system according to claim 12 further comprising a cell which expresses said Cre and said endonuclease which cleaves said endonuclease recognition site.

15. The system according to claim 11 further comprising a cell which expresses one or more adenoviral gene products encoded by adenoviral E1.

16. The system according to claim 11 wherein said helper adenovirus nucleic acid sequence comprises a deletion or mutation in a sequence encoding an adenovirus pIX gene product, rendering the nucleic acid sequence unable to produce the pIX gene product in a functional form, thereby inhibiting packaging adenoviral DNA larger than approximately 35 Kb.

17. The system according to claim 16 further comprising a cell which expresses said adenovirus pIX gene product.

18. A method for making a helper dependent adenovirus vector preparation which comprises: (A) making a helper adenovirus having a nucleic acid sequence comprising an endonuclease recognition site inserted 3' to an adenoviral packaging signal, a first ITR located at one end of, and a second ITR located at the other end of, the helper adenovirus nucleic acid sequence, and a third ITR located between the first and second ITRs and disposed 3' to said endonuclease recognition site; and (B) propagating said helper dependent adenovirus vector in the presence of said helper adenovirus of (A) in a cell permissive for replication of said helper dependent adenovirus vector, wherein during said propagating said helper adenovirus nucleic acid sequence is rendered incapable of being packaged into an infectious adenoviral virion due to deletion of the adenoviral packaging signal by endonuclease-mediated cleavage, alone or in combination with: (a) site-directed recombinatorial excision of said packaging signal: or (b) a deletion or mutation of adenoviral pIX encoding sequences, whereby a size restricted limitation of genome packaging prevents packaging of a genome which exceeds approximately 35 kb; or both (a) and (b).

19. The method according to claim 18 wherein said step for making said helper dependent adenovirus vector comprises co-introducing said helper dependent adenoviral vector and said helper adenovirus into a cell, wherein said cell expresses an endonuclease which induces endonuclease-mediated cleavage of the adenoviral packaging signal from said helper adenovirus.

20. The method according to claim 19 wherein said cell further expresses a recombinase which induces site-directed recombinatorial excision of said packaging signal.

21. The method according to claim 18 additionally comprising propagating said helper adenovirus, said helper adenovirus nucleic acid sequence comprising a deletion or mutation in a pIX encoding nucleic acid sequence rendering the helper adenovirus nucleic acid sequence unable to produce a functional pIX gene product, such that reduced functional pIX protein levels are produced by said helper adenovirus in cells expressing adenoviral pIX.

22. The method according to claim 18 further comprising co-introducing said helper dependent adenoviral vector and said helper virus into a cell which does not express adenoviral pIX.

* * * * *

SEQUENCE LISTING

<160> NUMBER OF SEQ ID NOS: 20

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide sequence for cloning, sequencing, PCR,
      hybridization, primer extension

<400> SEQUENCE: 1
acttaagcta gggataacag ggtaatatag                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide sequence for cloning, sequencing, PCR,
      hybridization, primer extension

<400> SEQUENCE: 2
tgaattcgat ccctattgtc ccattatatc                                    30

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide sequence for cloning, sequencing, PCR,
      hybridization, primer extension

<400> SEQUENCE: 3
cggatccaag cttgcgagat cgaattc                                       27

<210> SEQ ID NO 4
<211> LENGTH: 27
<212> TYPE: DNA
<213> ORGANISM: Artificial Sequence

```
<220> FEATURE:
<223> OTHER INFORMATION: Description of Artificial Sequence:
      Oligonucleotide sequence for cloning, sequencing, PCR,
      hybridization, primer extension

<400> SEQUENCE: 4
gcctaggtcg acactccgcc ctaaaac                                       27

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide sequence for cloning, sequencing, PCR,
      hybridization, primer extension

<400> SEQUENCE: 5
ggatatctgc agatctactc cgccctaaaa c                                  31

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide sequence for cloning, sequencing, PCR,
      hybridization, primer extension

<400> SEQUENCE: 6
cctcgagtcg acgcgagatc gaattc                                        26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide sequence for cloning, sequencing, PCR,
      hybridization, primer extension

<400> SEQUENCE: 7 gggggggtcat gaaaaagcct gaactc                                       26

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide sequence for cloning, sequencing, PCR,
      hybridization, primer extension

<400> SEQUENCE: 8 ggggggggtcg accagacccc acgcaacg                                     28

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence:cDNA

<400> SEQUENCE: 9
gaattcagat ccgccgccat atgggatcat catcagacga c                       41

<210> SEQ ID NO 10
```

```
<211> LENGTH: 26
<212> TYPE: DNA
<213> ORGANISM: Artificial Sequence
<220> FEATURE:
<223> OTHER INFORMATION: Description of Artificial Sequence:cDNA

<400> SEQUENCE: 10
ccaccaaaaa aaaacgaaaa gtagaa                                         26

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 11

Met Gly Ser Ser Asp Asp
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 12

Pro Pro Lys Lys Asn Glu Lys
  1               5

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:cDNA

<400> SEQUENCE: 13
gaattcgccg ccgctatggg atcatcatca gacgac                              36

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:cDNA

<400> SEQUENCE: 14
ccaccaaaaa aaaaacgaaa agtagaa                                        27

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 15

Met Gly Ser Ser Ser Asp Asp
  1               5

<210> SEQ ID NO 16
<211> LENGTH: 9
```

-continued

```
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 16

Pro Pro Lys Lys Lys Arg Lys Val Glu
  1               5

<210> SEQ ID NO 17
<211> LENGTH: 136
<212> TYPE: DNA
<213> ORGANISM: Artificial Sequence
<220> FEATURE:
<223> OTHER INFORMATION: Description of Artificial Sequence:cDNA

<400> SEQUENCE: 17
aattcgccgc cgccatggga tcatcatcag acgacgaagc aacagcagac gcacaacacg      60
cagcaccacc aaaaaaaaaa cgaaaagtag aagacccacg atttatgtac ccatacgatg     120
ttcctgacta tgcggg                                                    136

<210> SEQ ID NO 18
<211> LENGTH: 134
<212> TYPE: DNA
<213> ORGANISM: Artificial Sequence
<220> FEATURE:
<223> OTHER INFORMATION: Description of Artificial Sequence:cDNA

<400> SEQUENCE: 18
tacccgcata gtcaggaaca tcgtatgggt acataaatcg tgggtcttct acttttcgtt      60
ttttttttgg tggtgctgcg tgttgtgcgt ctgctgttgc ttcgtcgtct gatgatgatc     120
ccatggcggc ggcg                                                      134

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:cDNA

<400> SEQUENCE: 19
acttaagcta gggataacag ggtaatatag                                       30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:cDNA

<400> SEQUENCE: 20
ctatattacc ctgttatccc tagcttaagt                                       30
```